(12) United States Patent
Garneau-Tsodikova et al.

(10) Patent No.: US 10,253,035 B2
(45) Date of Patent: Apr. 9, 2019

(54) EIS INHIBITORS

(71) Applicant: University of Kentucky Research Foundation, Lexington, KY (US)

(72) Inventors: Sylvie Garneau-Tsodikova, Lexington, KY (US); Oleg V. Tsodikov, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 15/836,666

(22) Filed: Dec. 8, 2017

(65) Prior Publication Data

US 2018/0162867 A1 Jun. 14, 2018

Related U.S. Application Data

(60) Provisional application No. 62/595,947, filed on Dec. 7, 2017, provisional application No. 62/431,744, filed on Dec. 8, 2016.

(51) Int. Cl.

| | | |
|---|---|---|
| *C07D 491/048* | (2006.01) |
| *A61P 11/00* | (2006.01) |
| *C07D 491/113* | (2006.01) |
| *C07D 487/04* | (2006.01) |
| *C07D 241/44* | (2006.01) |
| *C07D 333/80* | (2006.01) |
| *C07D 209/38* | (2006.01) |
| *C07C 217/58* | (2006.01) |
| *C07C 47/575* | (2006.01) |
| *C07D 211/52* | (2006.01) |
| *C07D 275/03* | (2006.01) |
| *C07D 491/10* | (2006.01) |

(52) U.S. Cl.
CPC .......... *C07D 491/048* (2013.01); *A61P 11/00* (2018.01); *C07C 47/575* (2013.01); *C07C 217/58* (2013.01); *C07D 209/38* (2013.01); *C07D 211/52* (2013.01); *C07D 241/44* (2013.01); *C07D 275/03* (2013.01); *C07D 333/80* (2013.01); *C07D 487/04* (2013.01); *C07D 491/10* (2013.01); *C07D 491/113* (2013.01)

(58) Field of Classification Search
CPC .................... C07D 491/048; A61P 11/00
See application file for complete search history.

(56) References Cited

PUBLICATIONS

Garzan, et al., Discovery and optimization of two Eis inhibitor families as kanamycin adjuvants against drug-resistant M. tuberculosis. ACS Med. Chem. Lett. Jul. 2016, pp. 1219-1221.
Green, et al., Identification and characterization of inhibitors of the aminoglycoside resistance acetyltransferase Eis from Mycobacterium tuberculosis. ChemMedChem Jul. 2012, 73-77.
Willby, et al., Potent inhibitors of acetyltransferase Eis overcome kanamycin resistance in Mycobacterium tuberculosis. ACS Chem. Biol. Nov. 2016, 1639-1646.
Garzan, et al., Combating Enhanced Intracellular Survival (Eis)-Mediated Kanamycin Resistance of Mycobacterium tuberculosis by Novel Pyrrolo[1,5-a]pyrazine-Based Eis Inhibitors, ACS Infect. Dis. Mar. 2017, pp. 302-309.
Garzan, et al., Supporting Information for Combating Enhanced Intracellular Survival (Eis)-Mediated Kanamycin Resistance of Mycobacterium tuberculosis by Novel Pyrrolo[1,5-a]pyrazine-Based Eis Inhibitors, ACS Infect. Dis. Mar. 2017, pp. S1-S126.
Green, et al., Supporting Information for Identification and characterization of inhibitors of the resistance acetyltransferase Eis from Mycobacterium tuberculosis. 2012, pp. S1-S3.
Ngo, et al., Potent 1,2,4-Triazino[5,6b]indole-3-thioether Inhibitors of the 2 Kanamycin Resistance Enzyme Eis from Mycobacterium tuberculosis, ACS Infect. Dis., Mar. 21, 2018, pp. 1-11.
Garzen, et al., Sulfonamide-Based Inhibitors of Aminoglycoside Acetyltransferase Eis Abolish Resistance to Kanamycin in Mycobacterium tuberculosis, J. Med. Chem. 2016, 59, 10619-10628.

*Primary Examiner* — Golam M Shameem
(74) *Attorney, Agent, or Firm* — Stites & Harbison PLLC; Mandy Wilson Decker

(57) ABSTRACT

Compounds and compositions are disclosed, which are useful as inhibitors of acetyltransferase Eis, a mediator of kanamycin resistance in *Mycobacterium tuberculosis*.

8 Claims, 24 Drawing Sheets

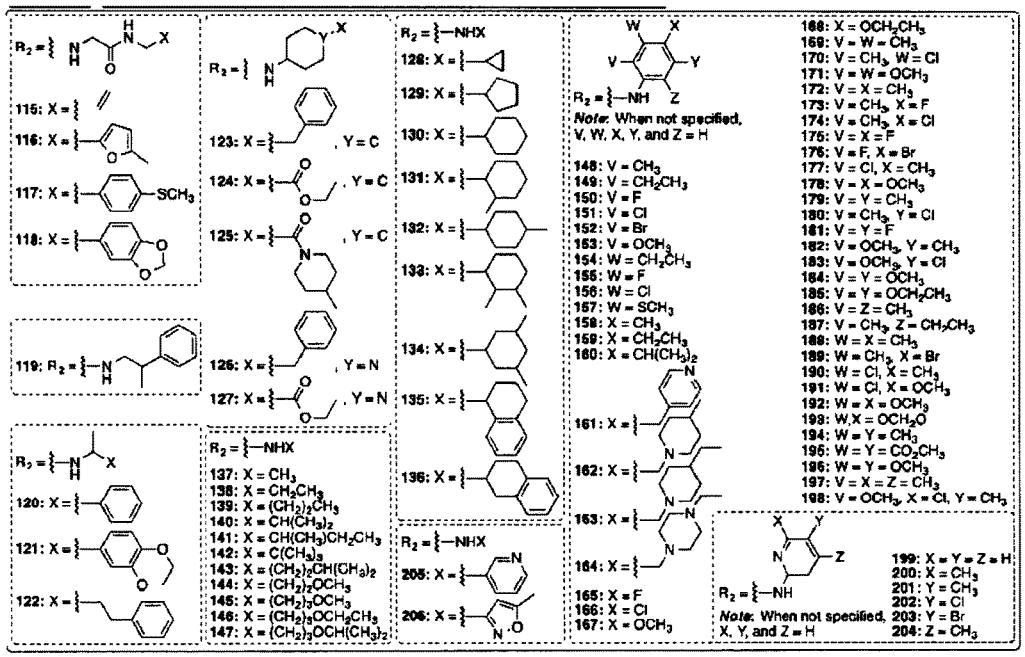
FIG. 17 con't

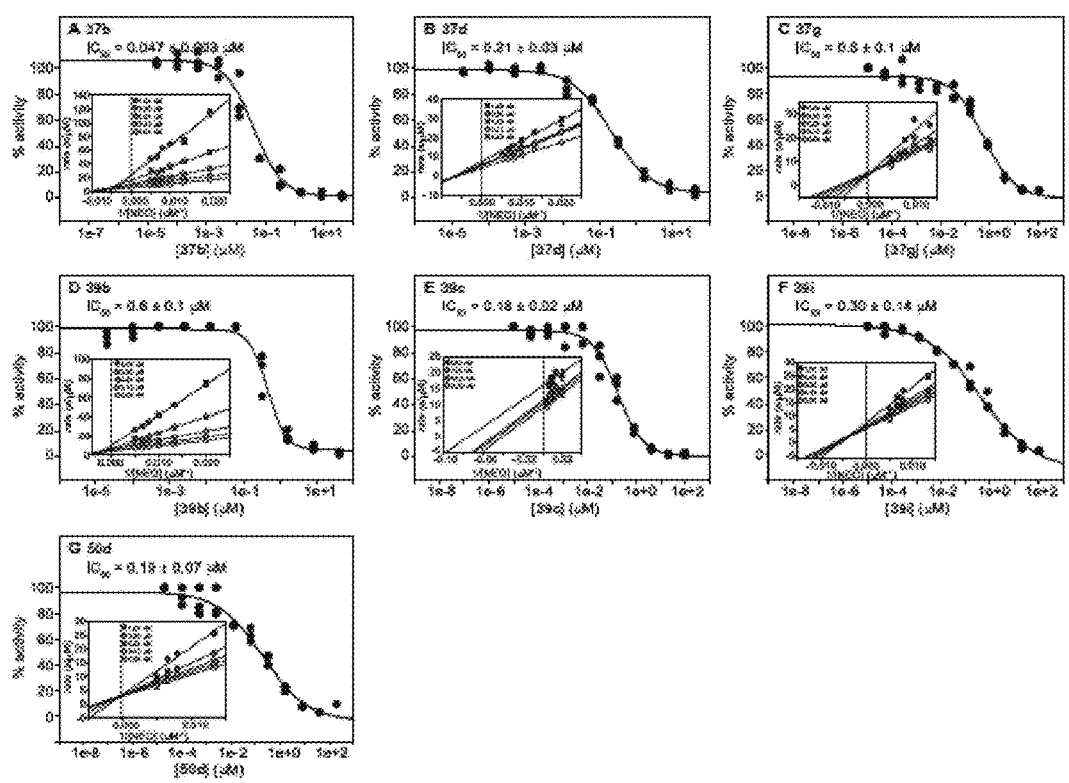
FIG. 21, cont'd

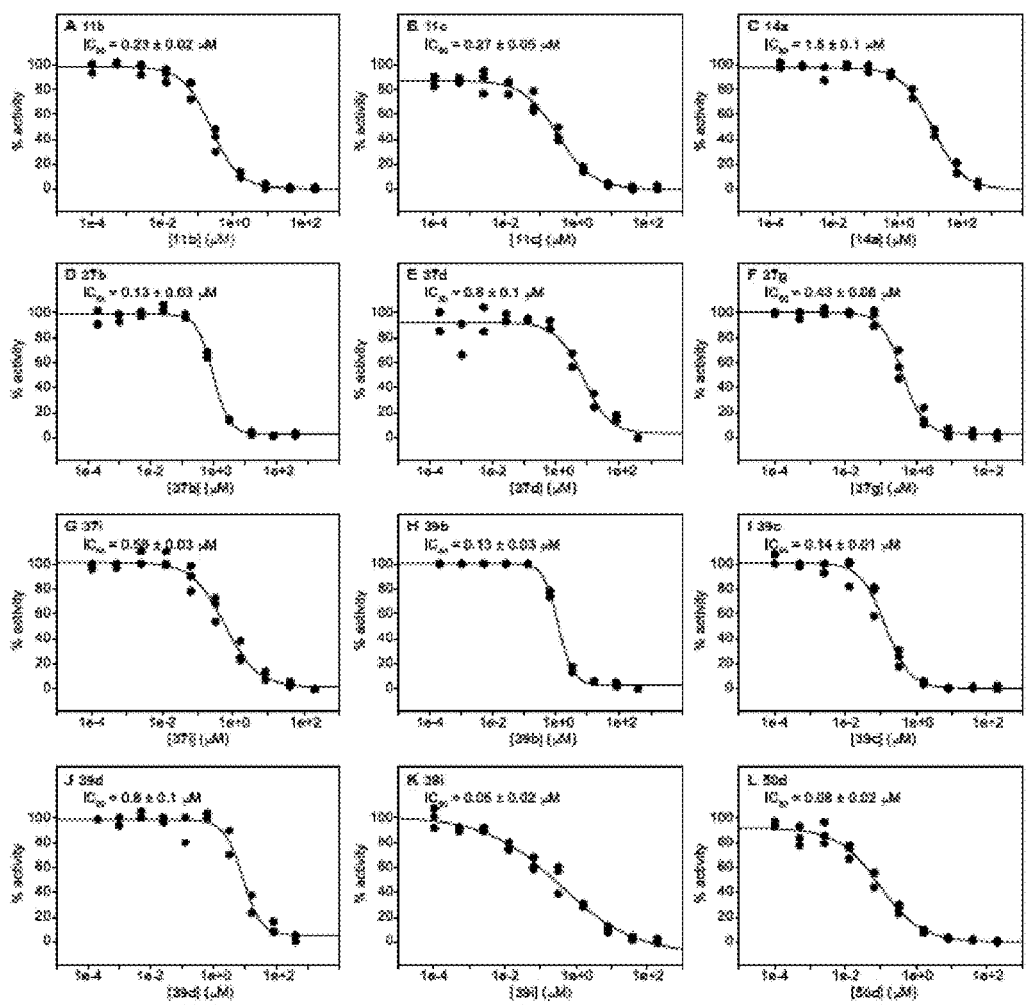
FIG. 21, cont'd

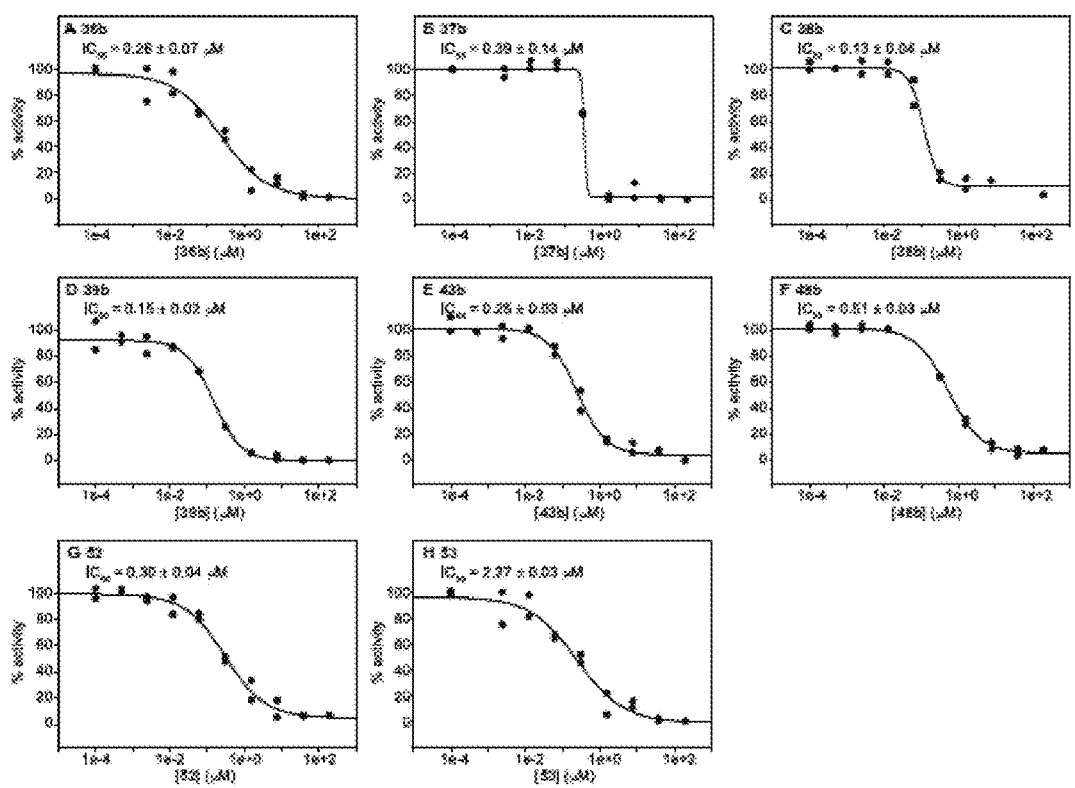
FIG. 21, cont'd

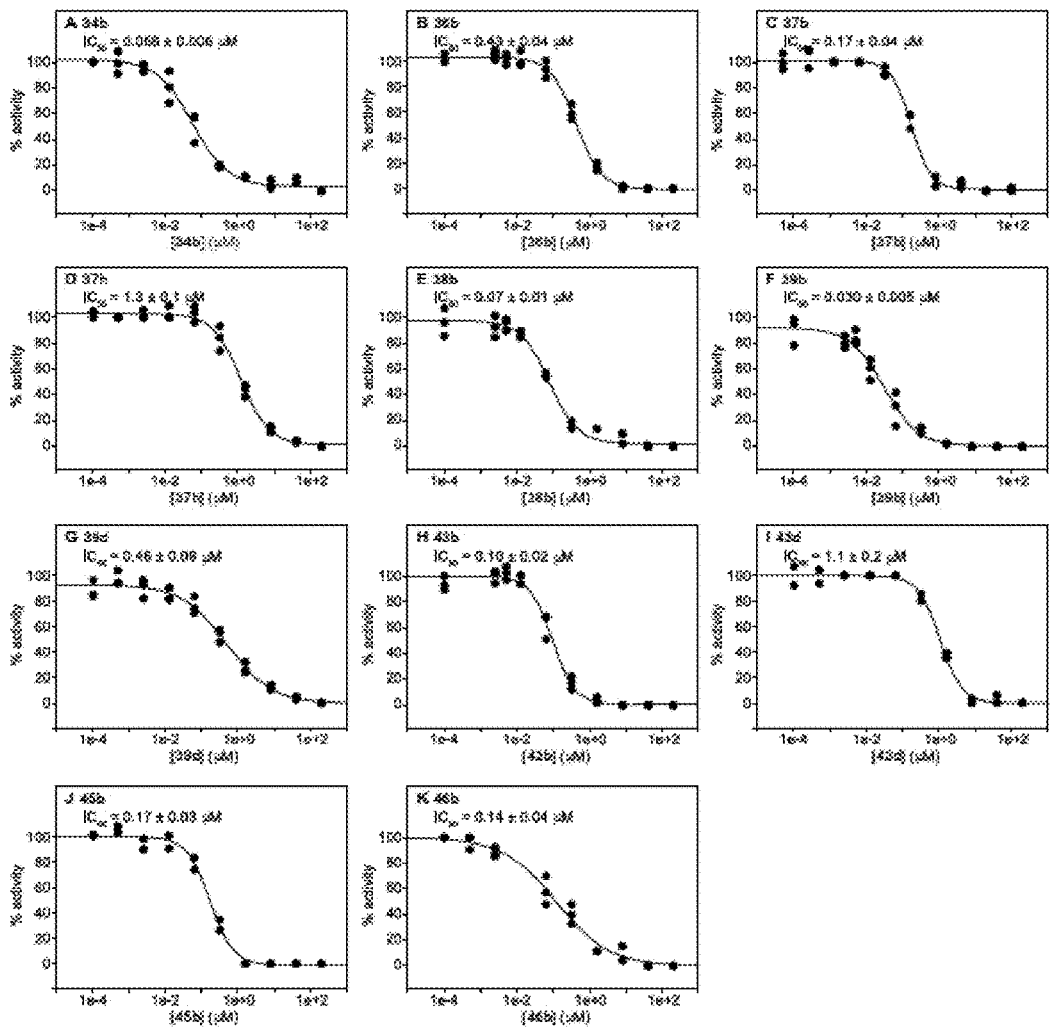
FIG. 21, cont'd

FIG. 21, cont'd

EIS INHIBITORS

RELATED APPLICATIONS

This application claims priority from U.S. Provisional Application Ser. Nos. 62/595,947 filed Dec. 7, 2017, and 62/431,744 filed Dec. 8, 2016, the entire disclosures of which are incorporated herein by this reference.

GOVERNMENT INTEREST

This invention was made with government support under National Institutes of Health (NIH) Grant AI090048. The government has certain rights in the invention.

TECHNICAL FIELD

The presently-disclosed subject matter relates to compositions useful as inhibitors of acetyltransferase Eis, a mediator of kanamycin resistance in *Mycobacterium tuberculosis*, and their methods of use. In particular, the compositions are sulfonamide-based and sulfonyl isothiazole-based small molecules.

INTRODUCTION

A major cause of tuberculosis (TB) resistance to the aminoglycoside kanamycin (KAN) is the *Mycobacterium tuberculosis* (Mtb) acetyltransferase Eis. Eis is a super-acetyltransferase from *M. tuberculosis* that inactivates all clinically used aminoglycosides. Upregulation of Eis is a frequent cause of clinical resistance to the aminoglycoside kanamycin (KAN) in TB. Upregulation of this enzyme is responsible for inactivation of KAN through acetylation of its amino groups.

Tuberculosis (TB) is an infectious disease caused by *Mycobacterium tuberculosis* (Mtb), and a major global health threat. In 2013, approximately 9.0 million people developed TB, and nearly 1.5 million died from the disease. Due to the spread of multidrug-resistant TB (MDR TB), defined as TB with resistance to at least isoniazid and rifampin (·10% of new TB cases in 2013) and extensively drug-resistant TB (XDR TB), defined as MDR TB with added resistance to at least a fluoroquinolone and an injectable drug (i.e., kanamycin (KAN), capreomycin, or amikacin), the need for novel strategies to combat drug resistant TB is urgent.

The aminoglycosides (AGs) kanamycin A (KAN) and amikacin (AMK) are used to treat MDR- and XDR-TB, but resistance to these agents occurs as well. Among mechanisms of clinically important transmissible drug resistance is the recently identified inactivation of an MDR-TB therapeutic, the aminoglycoside kanamycin, through its acetylation by an upregulated acetyltransferase, the Eis (enhanced intracellular survival) enzyme. We previously demonstrated that the Mtb Eis protein (Eis_Mtb) is an acetyltransferase capable of multiacetylating a variety of AGs, including the TB therapeutics KAN and AMK, via a random sequential mechanism, thereby abolishing the antibiotic activity of these drugs. The ability of acetylating an AG molecule at multiple amine positions due to its unique structure distinguishes Eis from other AG acetyltransferases (AACs), which are known to be exquisitely regiospecific. A crystal structure of Eis_Mtb in complex with coenzyme A and tobramycin demonstrated how tobramycin could interact with the Eis active site in two binding modes for the observed diacetylation of the 6'- and 3"-amines of this AG.

Multiacetylation by Eis has a defined pattern for each AG: the number of acetylations and the positions of the amino groups that get acetylated depend on the structure of the AG. Furthermore, Eis homologues from *Mycobacterium smegmatis*, *Mycobacterium abscessus*, *Anabaena variabilis*, *Bacillus anthracis*, *Gordonia bronchialis*, *Kocuria rhizophila* (9), and *Tsukamurella paurometabola* are also functional AACs, which exhibit differences in regiospecificity and can be inhibited by chlorhexidine, a non-clinically relevant Eis_Mtb inhibitor. In addition to AG substrate versatility, Eis enzymes display some acyl-CoA co-substrate promiscuity and can acetylate non-AG molecules containing lysine residues, such as capreomycin and the JNK-specific dual-specificity protein phosphatase 16 (DUSP16)/mitogen-activated protein kinase phosphatase-7 (MKP-7) pair. These observations underscore the uniqueness and versatility of Eis AG modifying activity and its high capacity for inactivation of diverse AG drugs.

The development of AGs that cannot be modified by Eis or a novel therapy that would involve an Eis inhibitor used in combination with KAN are two possible approaches to resolve the need in the field of drug resistant tuberculosis. The former route is complicated by the ability of Eis to accept structurally diverse AGs as substrates, whereas the latter route is potentially more suitable. The latter approach to combat drug resistance arising as a result of drug-modifying enzymes, then, is to use a combination therapy that includes an antibiotic along with an inhibitor of its associated resistance enzyme. In Mtb, including MDR TB, the combination of the β-lactamase inhibitor clavulanate and the β-lactam meropenem was demonstrated to overcome resistance to β-lactam antibiotics. With this strategy in mind, efforts have also been made towards identifying inhibitors of aminoglycoside acetyltransferases (AACs) present in non-mycobacteria, with limited pre-clinical progress, but these are not applicable for the mechanistically and structurally distinct Mtb Eis acetyltransferase. For example, aminoglycoside-acetyl coenzyme A bi-substrate inhibitors were found to potently inhibit AAC(6') enzymes in vitro, but were not effective in cell-based assays. Numerous cationic peptides that inhibit AAC(6') enzymes in vitro were identified, but these also displayed no antibacterial effects against resistant bacterial strains due to membrane permeability issues. Finally, the natural product aranorosin was found to be an inhibitor of the bifunctional AAC(6')-Ie/APH(2")-Ia enzyme, and its combination with the aminoglycoside arbekacin was shown to stop the growth of a methicillin-resistant *Staphylococcus aureus* strain.

We previously reported that some Eis inhibitors displayed AG-competitive and mixed modes of action, establishing a proof of principle for inhibition of Eis in vitro.

A two-drug combination therapy where one drug targets an offending cell and the other targets a resistance mechanism to the first drug is a time-tested, yet underexploited approach to combat or prevent drug resistance in an infectious disease. Furthermore, there remains a need for approaches to combat drug resistant TB.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compounds, compositions, and methods involving inhibition of Eis. In some embodiments, the compound has a scaffolds selected from the following:

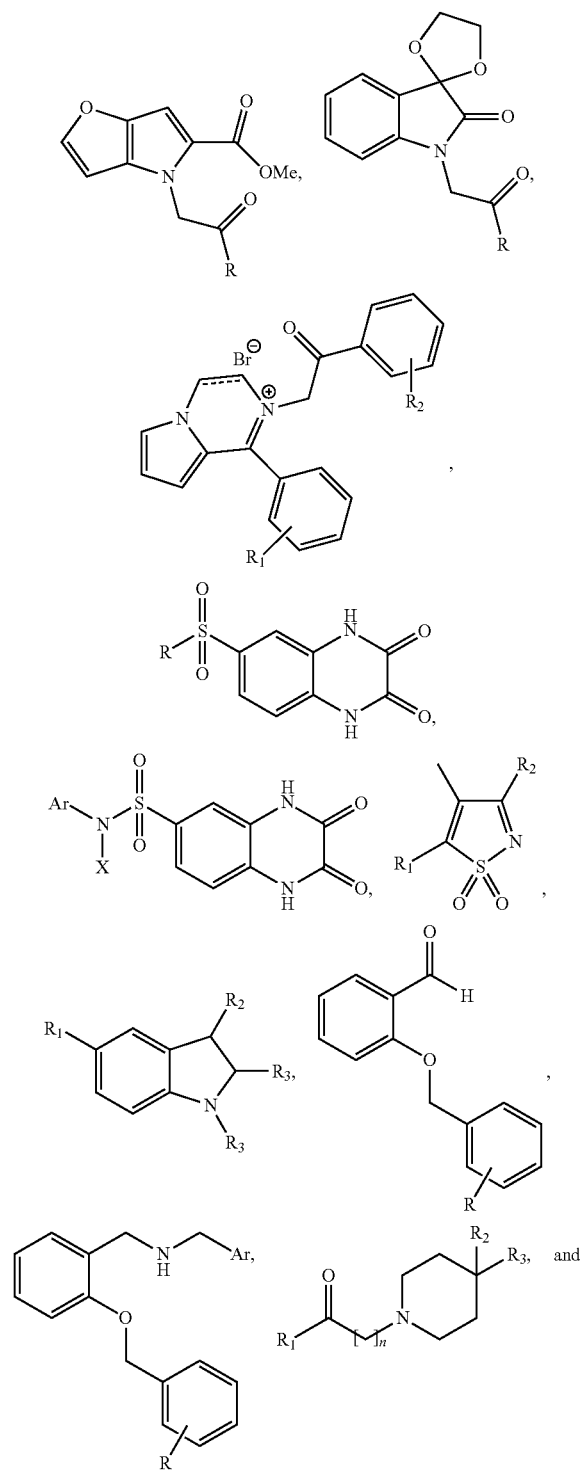

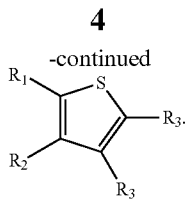

The presently-disclosed subject matter also includes a pharmaceutical composition comprising a compound as described herein, and a suitable pharmaceutical carrier.

In some embodiments, the composition includes a compound as described herein and an aminoglycoside. In some embodiments, the aminoglycoside is kanamycin (KAN).

The presently-disclosed subject matter also includes a method of inhibiting Eis, which involves administering an effective amount of a compound or composition as described herein. In some embodiments, the method further involves administering an aminoglycoside. In some embodiments, the aminoglycoside is kanamycin (KAN).

The presently-disclosed subject matter also includes a method of treating aminoglycoside-resistant *Mycobacterium tuberculosis* (Mtb), which involves administering an effective amount of a compound or composition as described herein. In some embodiments, the method also involves administering an aminoglycoside. In some embodiments, the aminoglycoside is kanamycin (KAN). In some embodiments, the aminoglycoside is administered to a subject in need of treatment for aminoglycoside-resistant Mtb.

The presently-disclosed subject matter also includes a kit, which can include a compound or composition as described herein, packaged together with an aminoglycoside.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
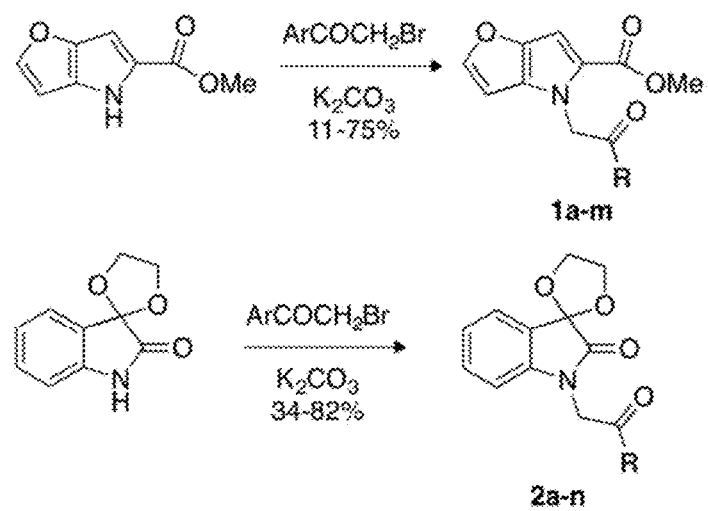
FIG. 1 includes preparation schemes and structures of exemplary Eis inhibitor scaffolds according to the presently-disclosed subject matter and discussed in Example 1.
Figure 2:
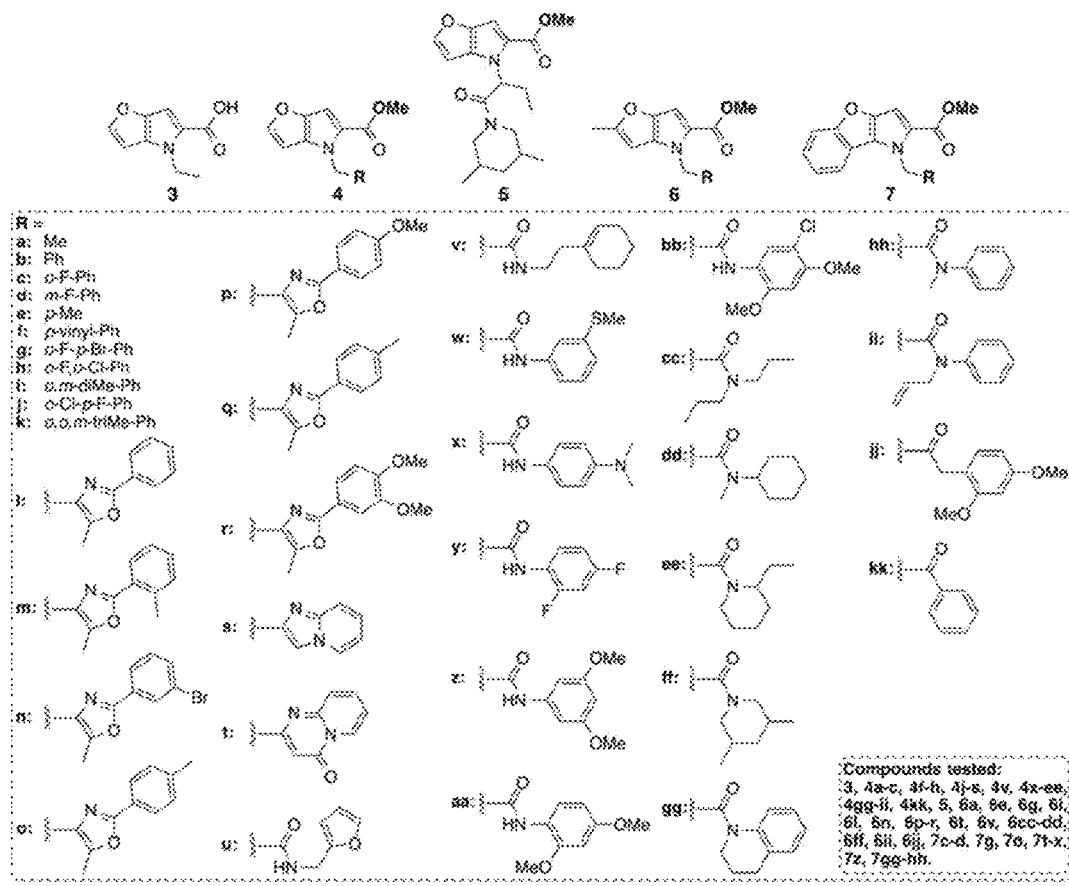
FIG. 2 includes structures of exemplary compounds according to the scaffolds set forth in FIG. 1.
Figure 3:
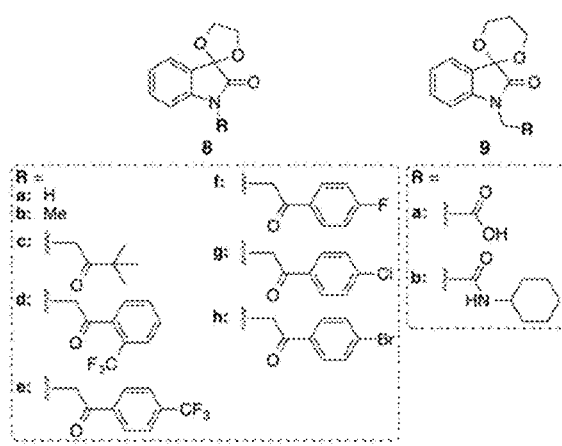
FIG. 3 includes structures of additional exemplary compounds according to the scaffolds set forth in FIG. 1.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter is illustrated by specific but non-limiting examples throughout this description. The examples may include compilations of data that are representative of data gathered at various times during the course of development and experimentation related to the present invention(s). Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The presently-disclosed subject matter includes compounds that are useful for inhibiting Eis.

In some embodiments, the compound is

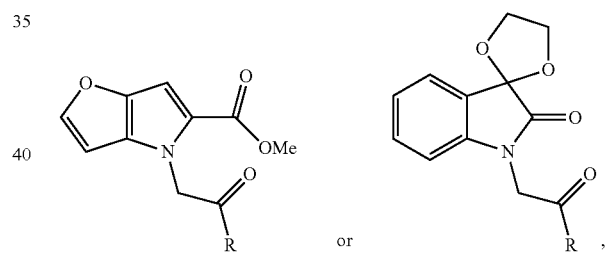

wherein R is selected from the group consisting of Ph, o-F-Ph, m-F-Ph, m-Cl-Ph, m-Br-Ph, m-OMe-Ph, p-F-Ph, p-Cl-Ph, p-Br-Ph, p-Me-Ph, naphthyl, Et, t-Bu, and m-$NO_2$-Ph.

In some embodiments, the compound is

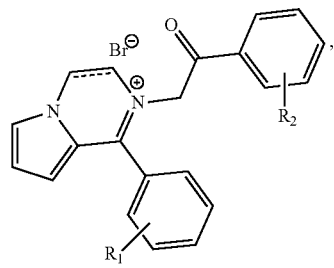

wherein $R_1$ is selected from the group consisting of H, p-F, m,p-di-F; and $R_2$ is selected from the group consisting of H, o-F, m-F, m-Cl, m-Br, m-OH, m-OMe, p-F, p-Cl, p-Br, and p-Me.

In some embodiments, the compound is
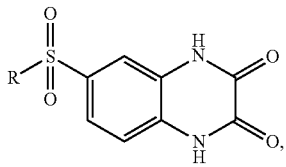
wherein R is selected from the group consisting of
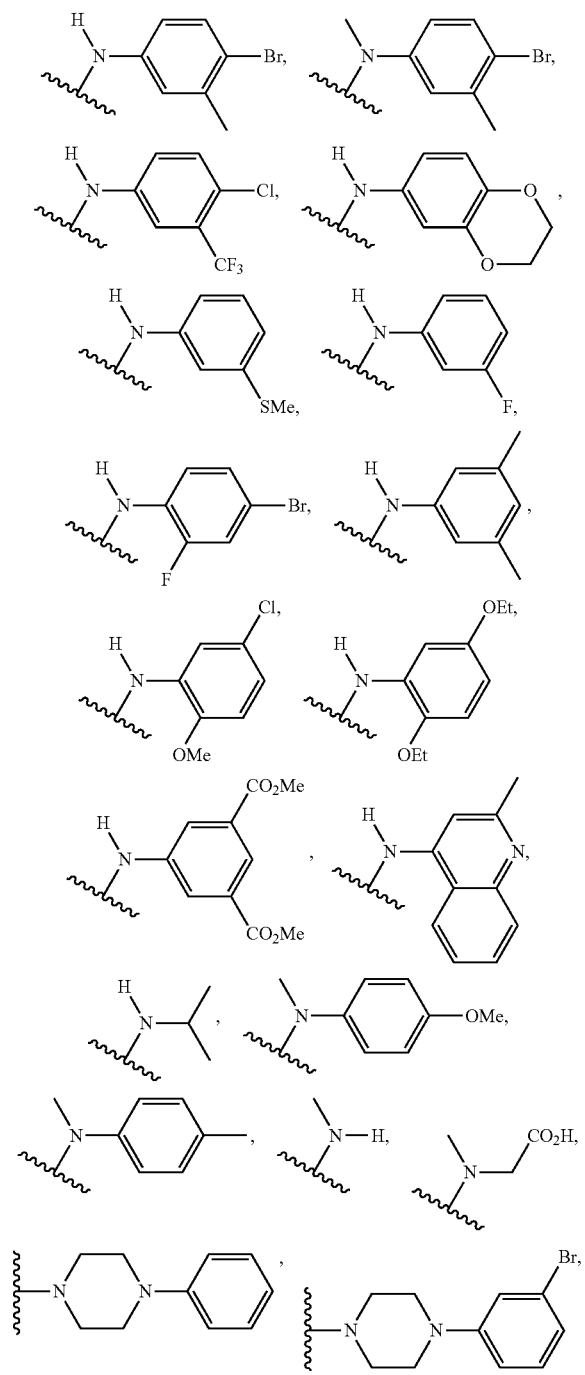
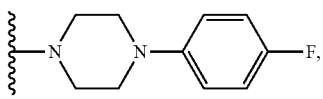
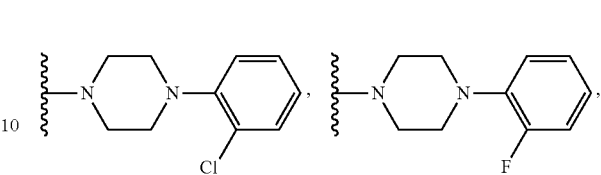
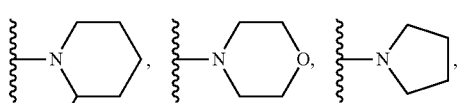
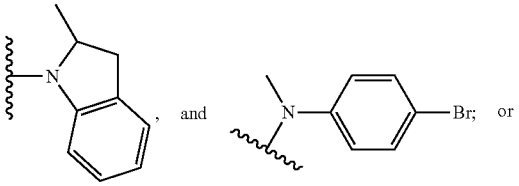
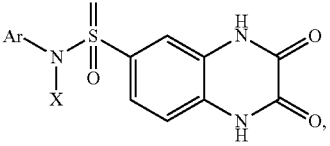
wherein X is selected from the group consisting of H and Me, and Ar is selected from the group consisting of
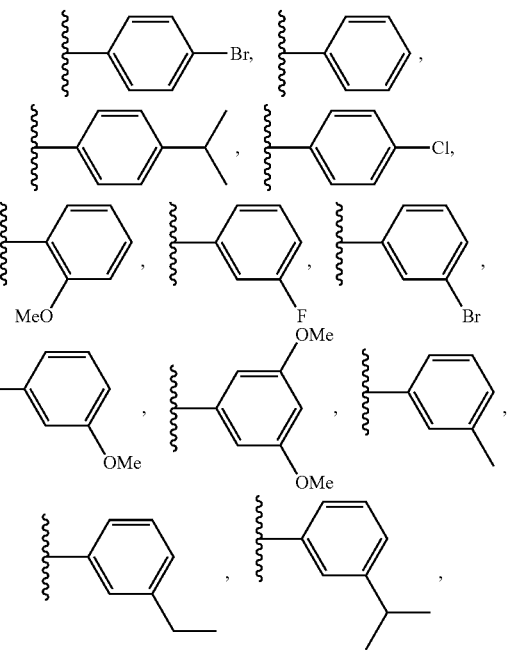

-continued
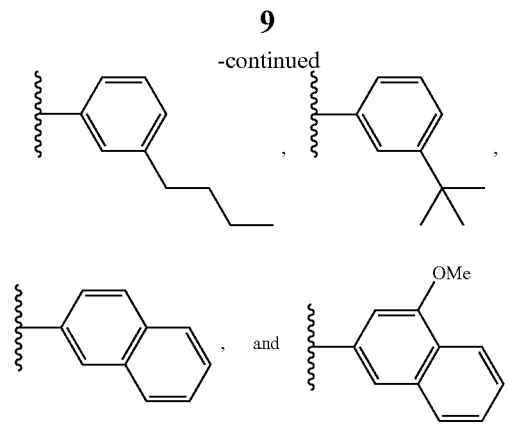
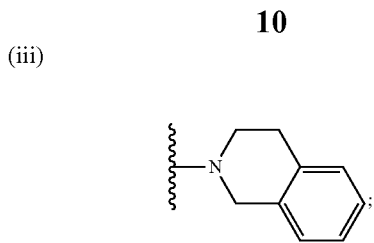
In some embodiments, the compound is
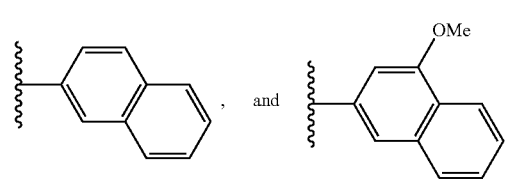
wherein $R_1$ is selected from the group consisting of
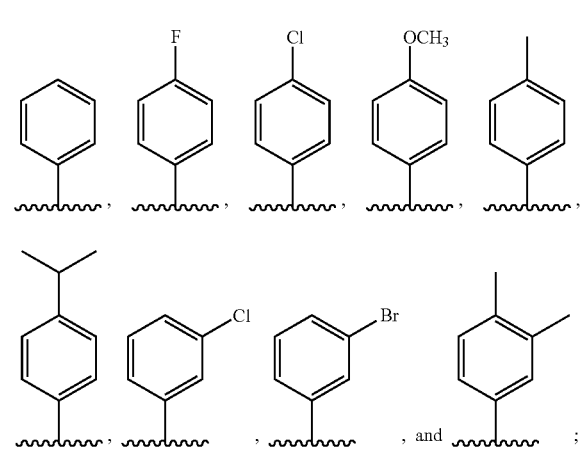
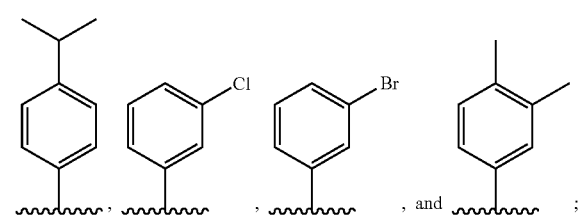
and wherein R2 is selected from the group consisting of
(i)
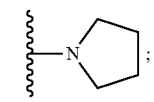
(ii)
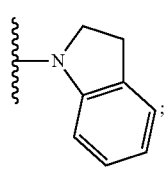 [SMILES: *N1CCc2ccccc21]
(iii)
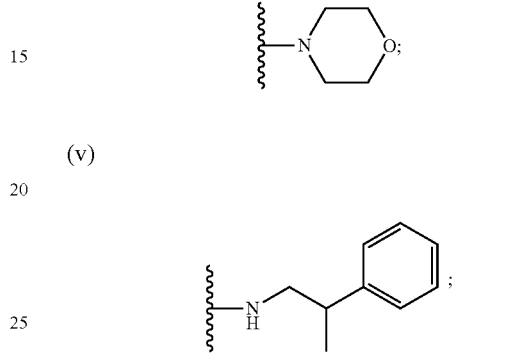
(iv)
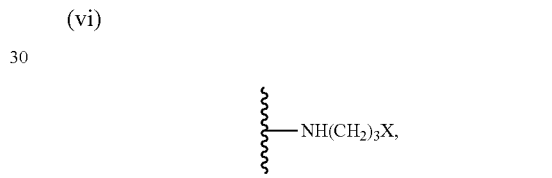
(v)
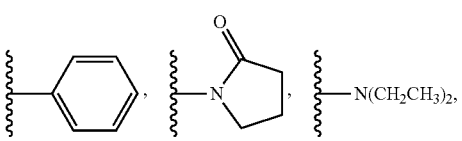
(vi)
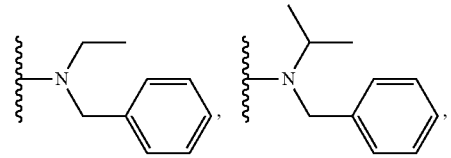
wherein X is selected from the group consisting of
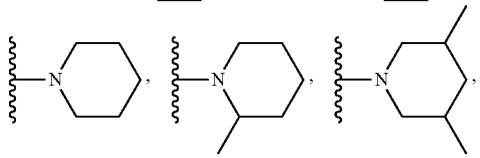
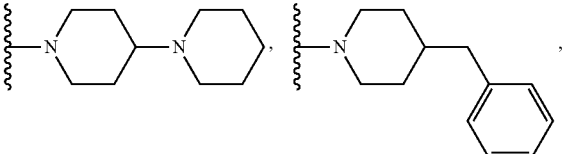
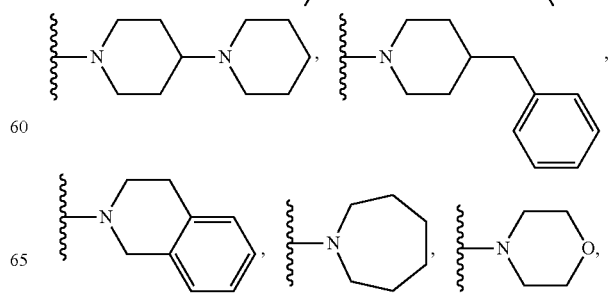

-continued
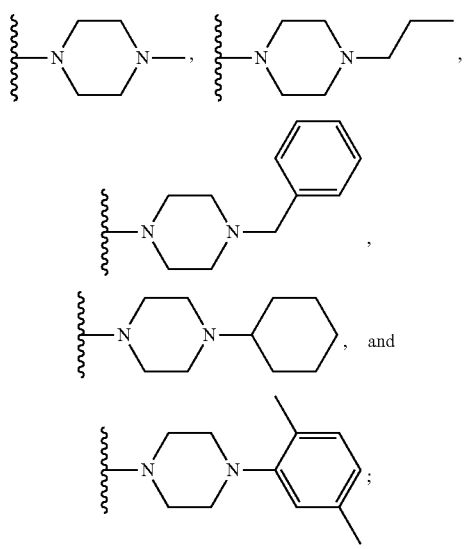
(vii)
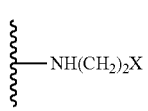
wherein X is selected from the group consisting of:
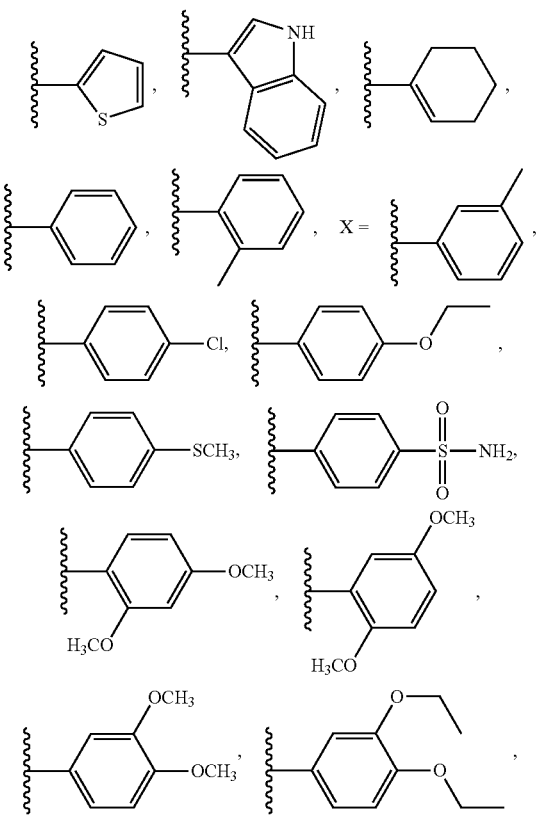
-continued
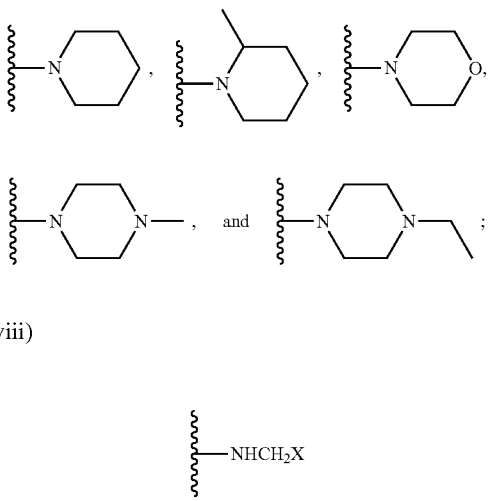
(viii)
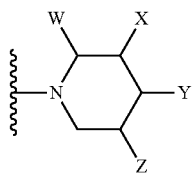
wherein X is selected from the group consisting of:
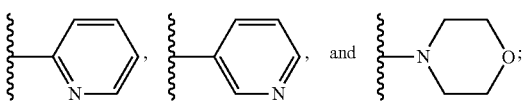
(ix)
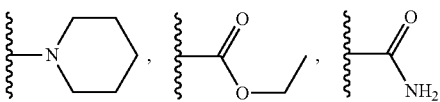
wherein W, X, and Z are each independently selected from the group consisting of H and CH$_3$, and wherein Y is selected from the group consisting of H, CH$_3$,
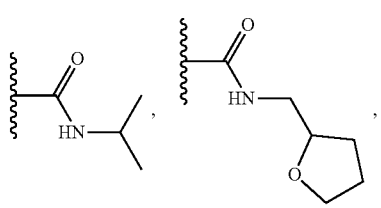
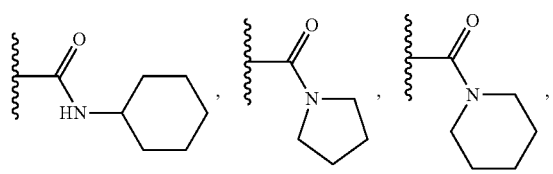

-continued

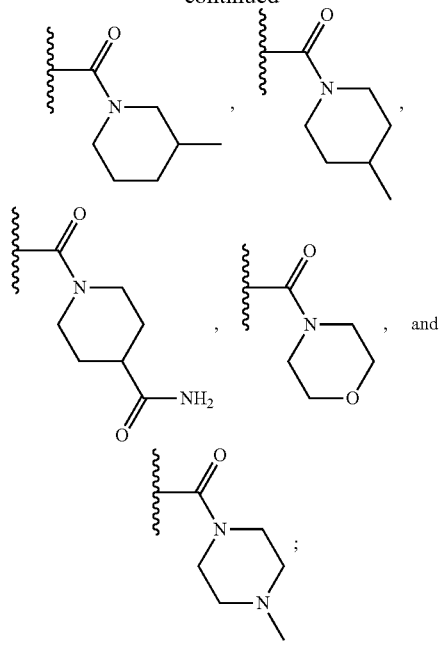

(x)

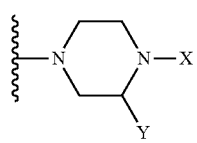

wherein Y is selected from the group consisting of H and CH₃, and wherein X is selected from the group consisting of CH₃, CH₂CH₃, (CH₂)₂CH₃,

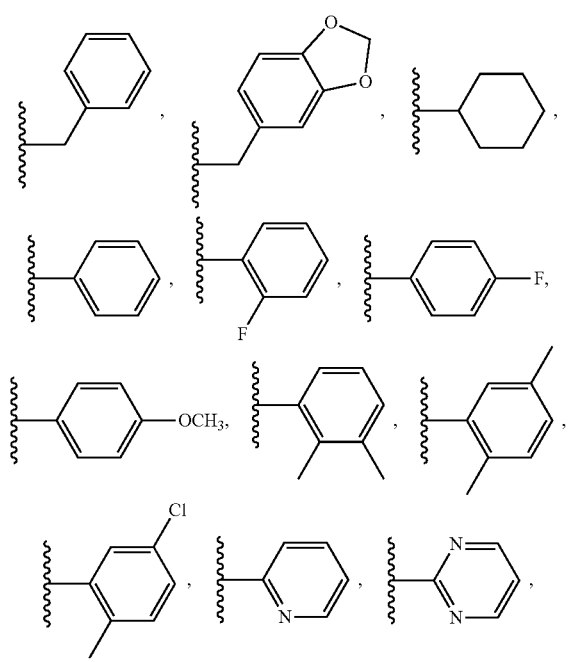

-continued

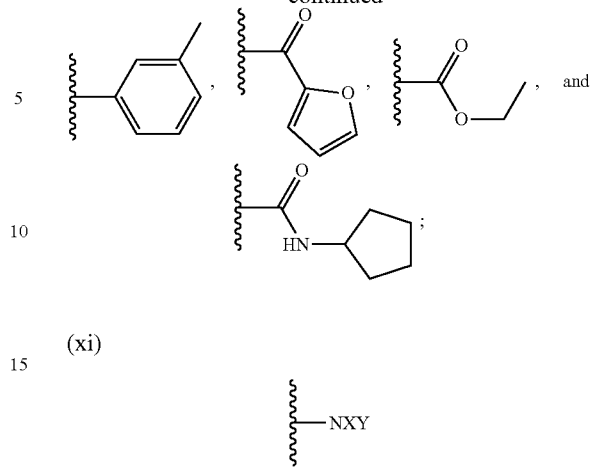

(xi)

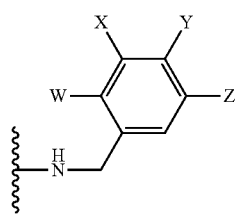

wherein
Y is selected from the group consisting of H, CH₃, CH₂CH₃, and CH(CH₃)₂, and
X is selected from the group consisting of CH₂CH₃,

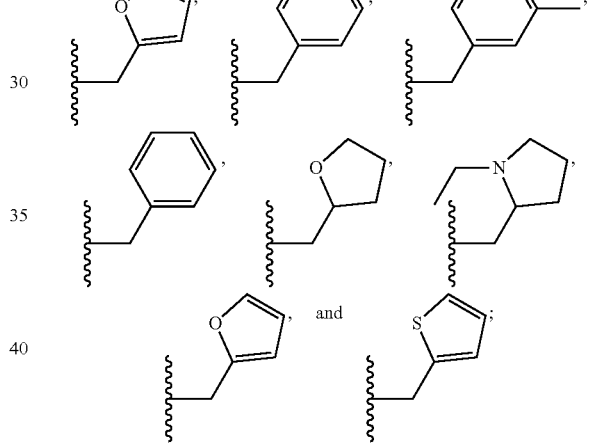

(xii)

wherein
W is selected from the group consisting of H, CH₃, F, Cl, OCH₃, and OCH₂CH₃,
X is selected from the group consisting of H, Cl, Br, OCH₃, OCH₂CH₃, and OCH₂O,
Y is selected from the group consisting of H, CH₃, CH₂CH₃, Br, F, Cl, OCH₃, OCH₂CH₃, O(CH)(CH₃)₂, OCH₂O, N(CH₃)₂, N(CH₂CH₃)₂, and
Z is selected from the group consisting of H and OCH₃;

(xiii)

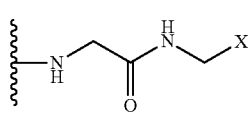

wherein X is selected from the group consisting of

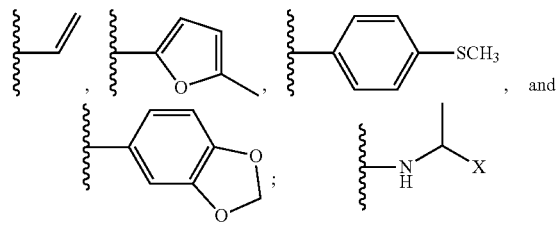

wherein X is selected from the group consisting of

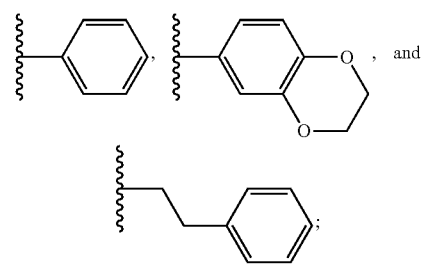

(xiv)

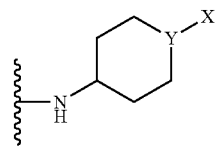

wherein
Y is selected from the group consisting of N and C, and
X is selected from the group consisting of

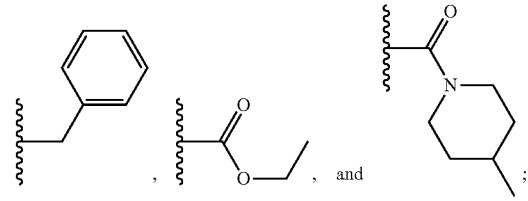

(xv)

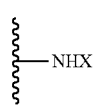

wherein X is selected from the group consisting of: $CH_3$, $CH_2CH_3$, $(CH_2)_2CH_3$, $CH(CH_3)_2$, $CH(CH_3)CH_2CH_3$, $C(CH_3)_3$, $(CH_2)_2CH(CH_3)_2$, $(CH_2)_2OCH_3$, $(CH_2)_3OCH_3$, $(CH_2)_3OCH_2CH_3$, $(CH_2)_3OCH(CH_3)_2$,

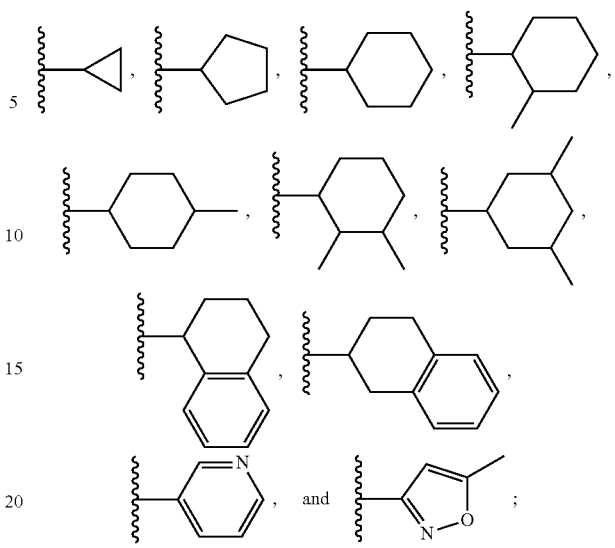

(xvi)

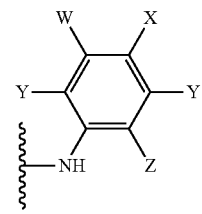

wherein
V is selected from the group consisting of H, $CH_3$, $CH_2CH_3$, F, Cl, Br, $OCH_3$, and $OCH_2CH_3$, W is selected from the group consisting of H, $CH_3$, F, Cl, $CH_2CH_3$, $SCH_3$, $OCH_3$, $OCH_2O$, and $CO_2CH_3$, X is selected from the group consisting of H, $CH_3$, $CH_2CH_3$, $CH(CH_3)_2$, F, Cl, Br, $OCH_3$, $OCH_2O$, $OCH_2CH_3$,

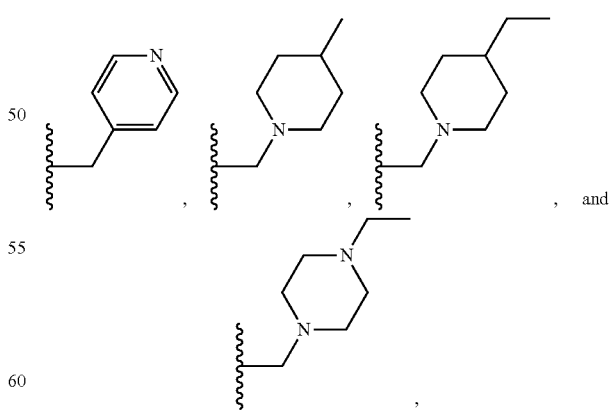

Y is selected from the group consisting of H, $CH_3$, F, Cl, $OCH_3$, $CO_2CH_3$, Br, $CH_2CH_3$, and $OCH_2CH_3$, Z is selected from the group consisting of H, $CH_3$, and $CH_2CH_3$, (xvii)

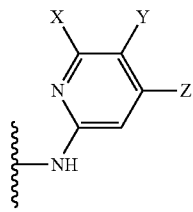

wherein
X is selected from the group consisting of H and CH₃,
Y is selected from the group consisting of H, CH₃, Cl, and Br, and
Z is selected from the group consisting of H and CH₃; and (xviii)

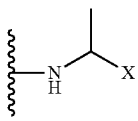

wherein X is selected from the group consisting of

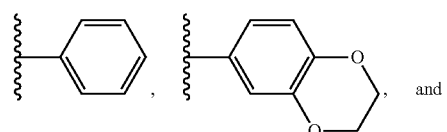, and

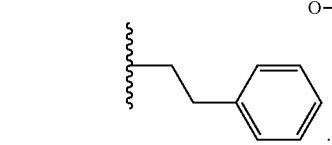.

In some embodiments, the compound is

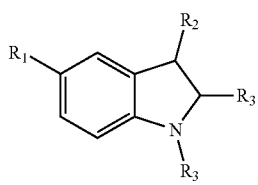

where R₁-R₄ are selected to provide a compound selected from the group consisting of:

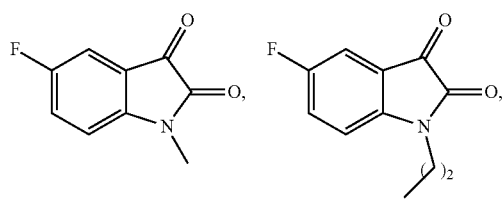

-continued

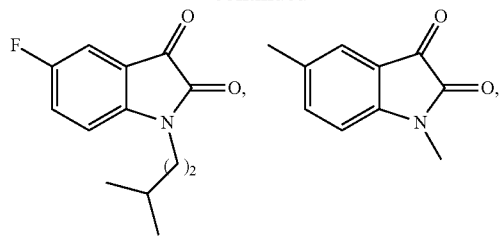

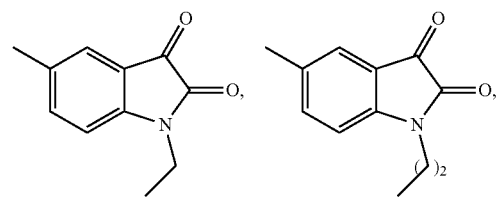

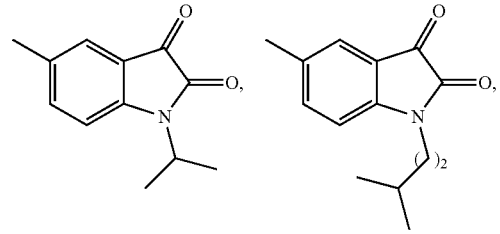

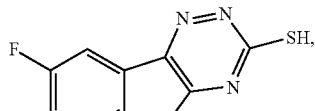

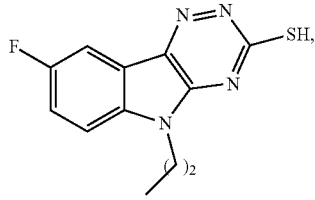

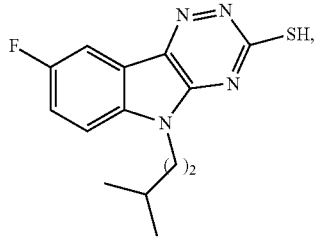

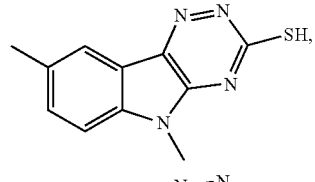

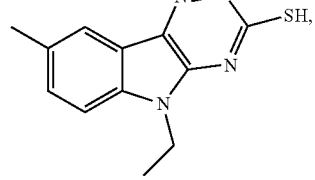

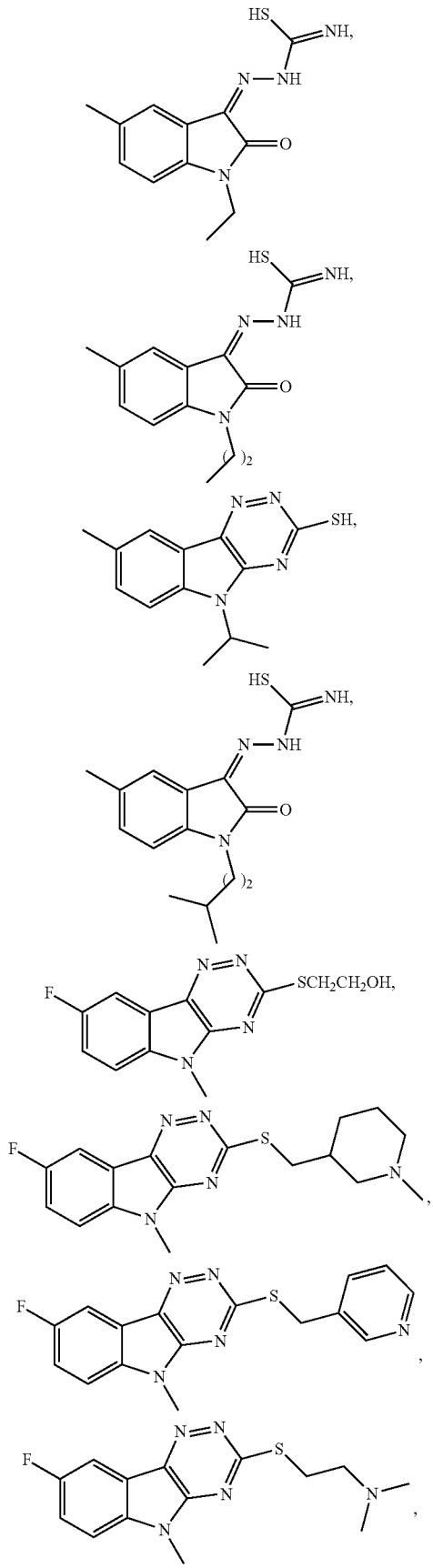
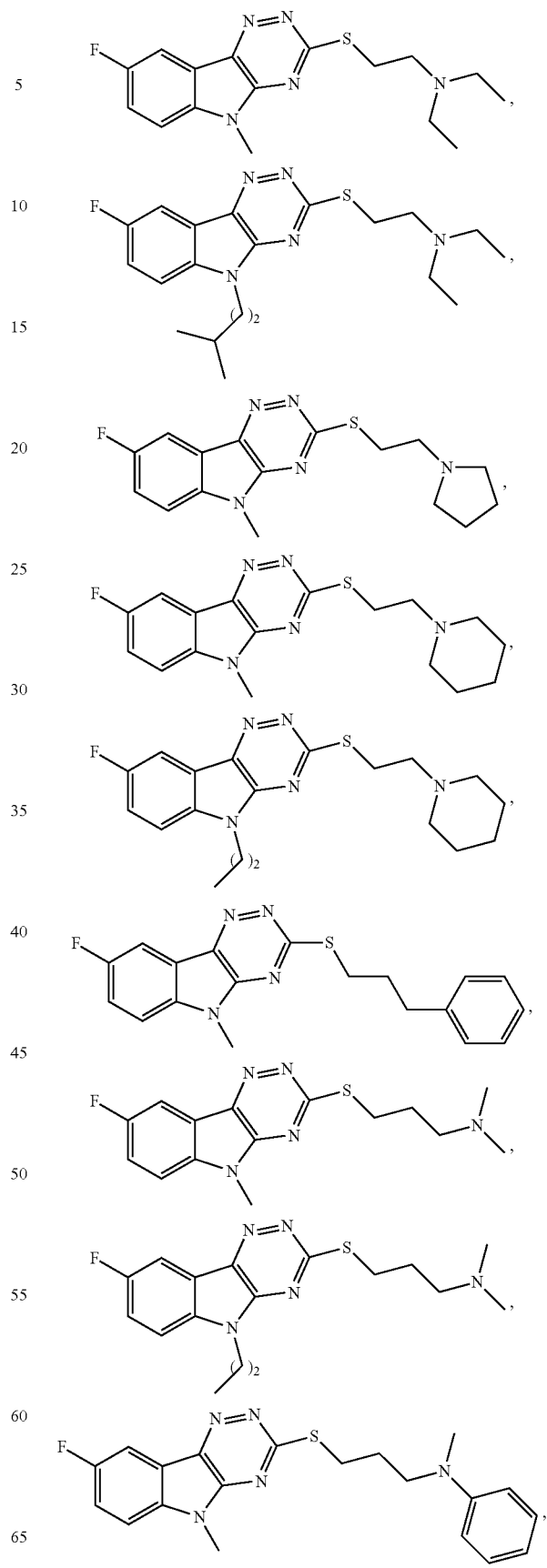

-continued
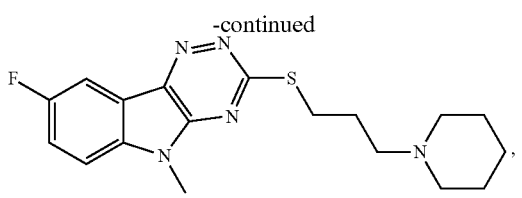
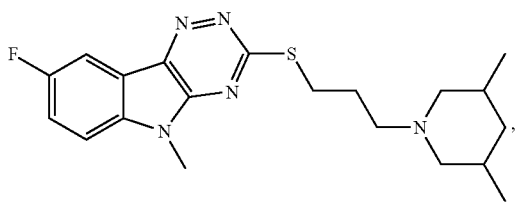
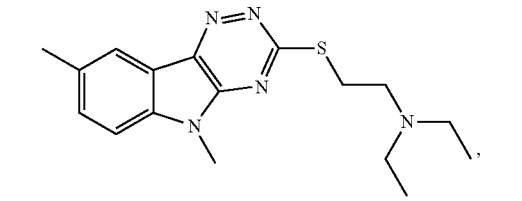
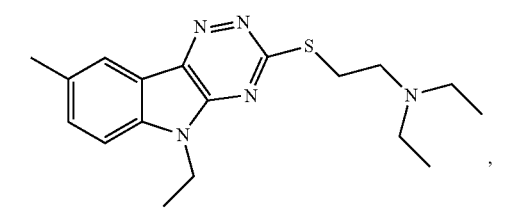
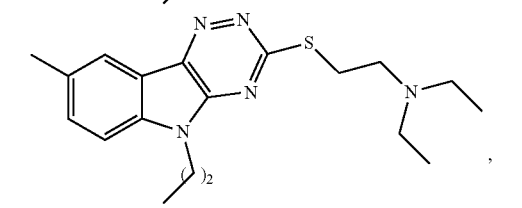
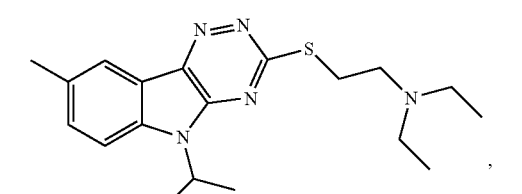
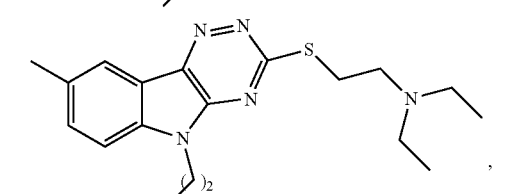
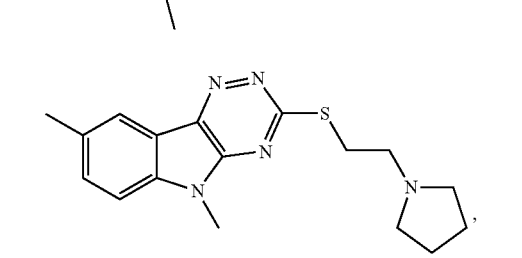
-continued
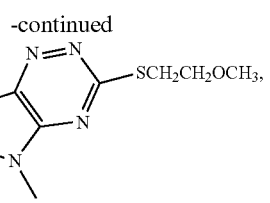
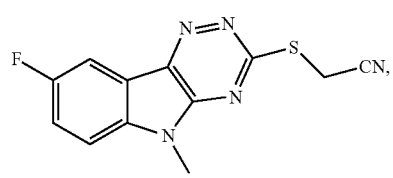
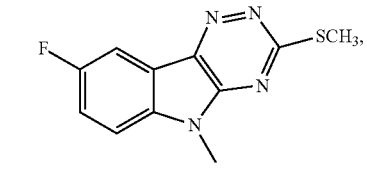
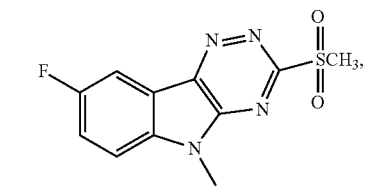
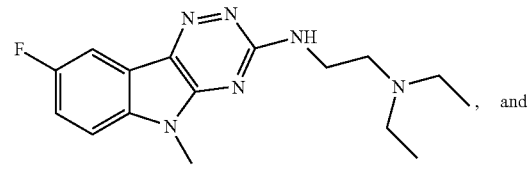, and
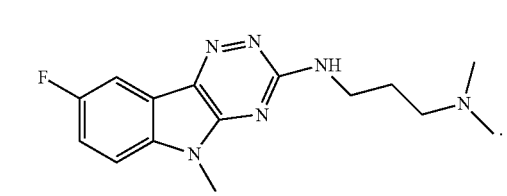.
In some embodiments, the compound is
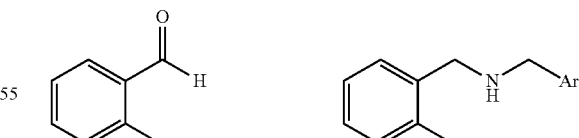 or 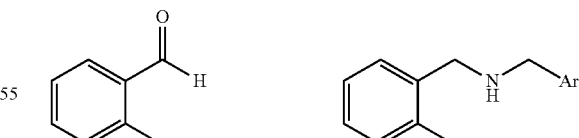,
wherein R is selected from the group consisting of 4-Cl, 4-F, 4-Br, 3-Cl, 3-F, and H; and Ar is selected from the group consisting of Ph, 3-Py, 2-Py, 4-Py, and Ph.

In some embodiments, the compound is
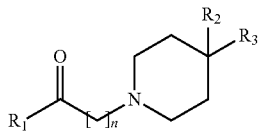
where R₁-R₃ and n are selected to provide a compound selected from the group consisting of:
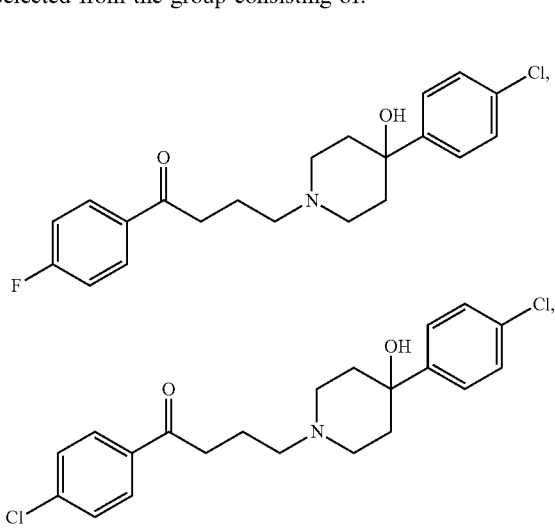
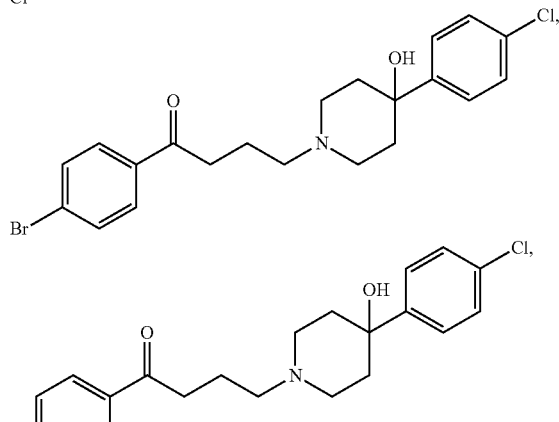
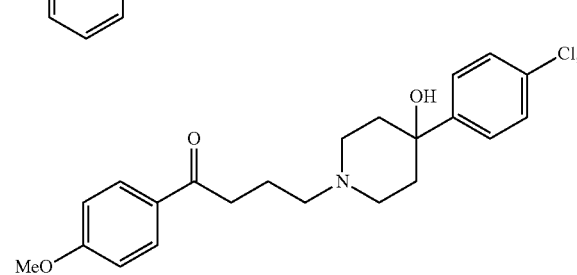
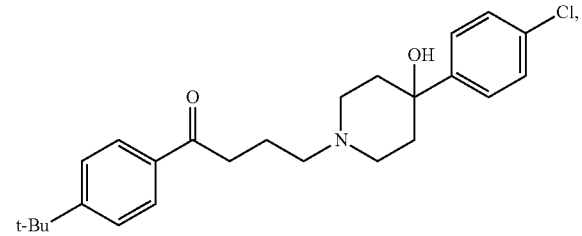
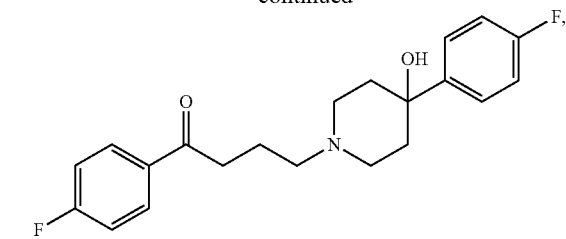
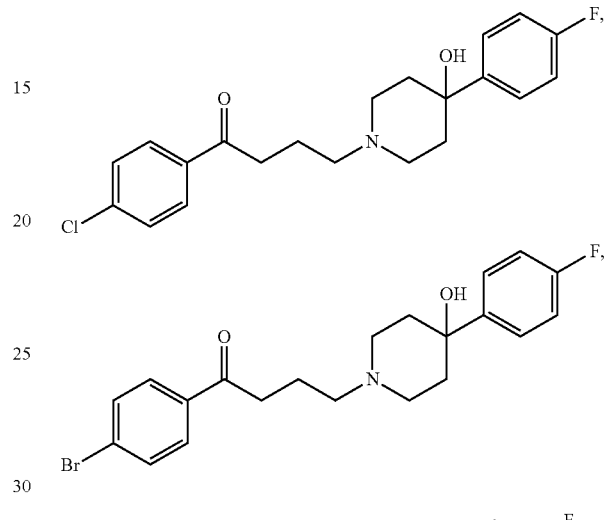
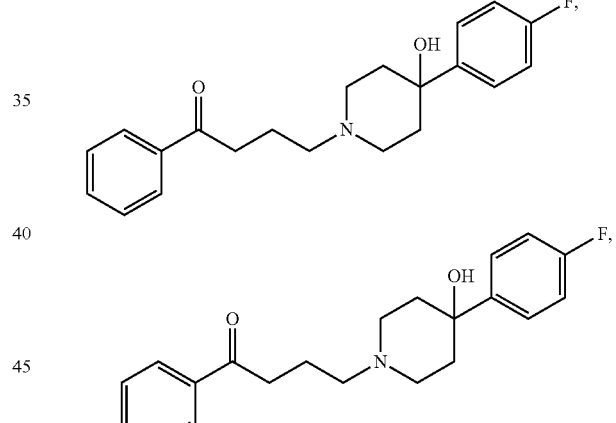
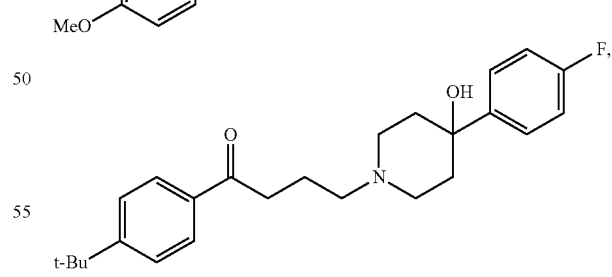
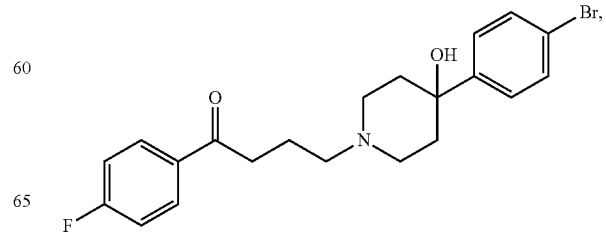

-continued
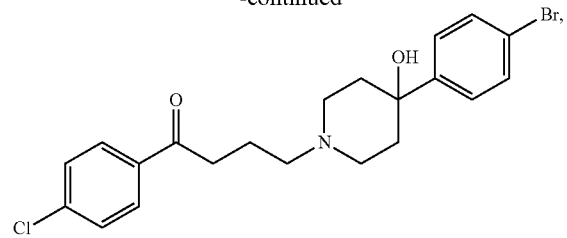
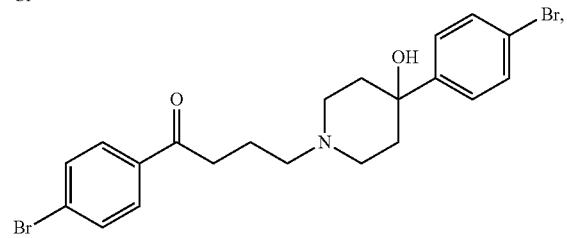
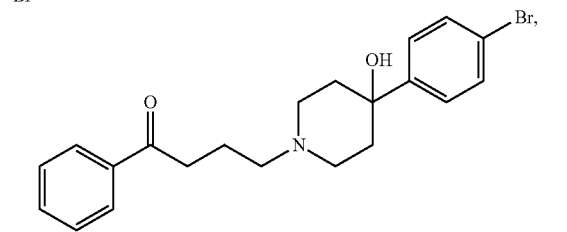
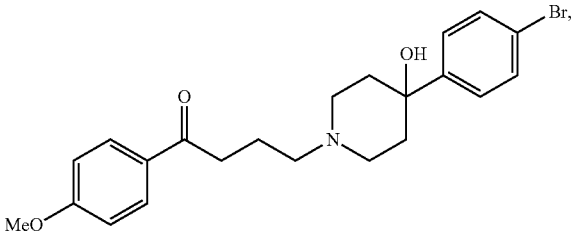
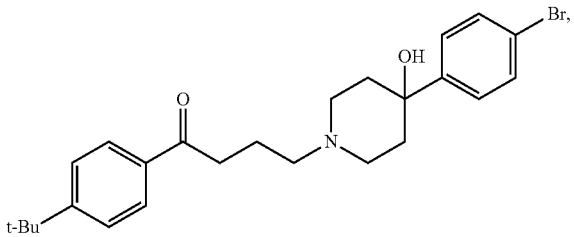
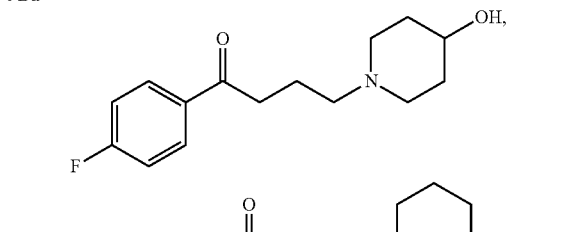
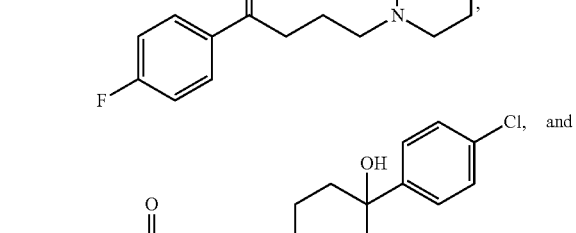
-continued
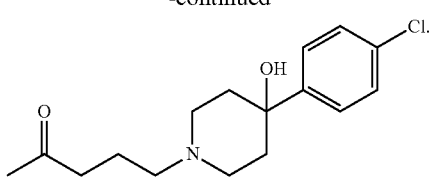
In some embodiments, the compound is
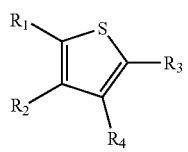
where $R_1$-$R_4$ are selected to provide a compound selected from the group consisting of:
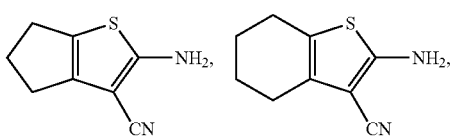
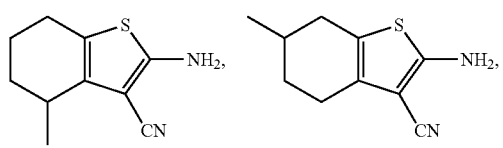
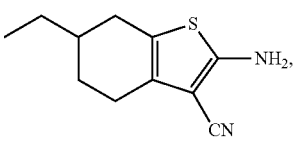
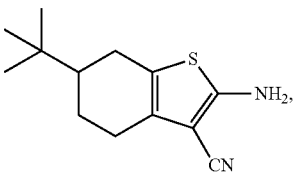
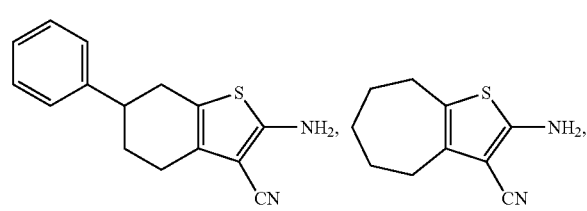
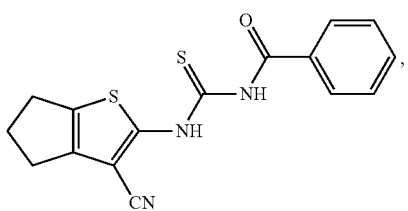

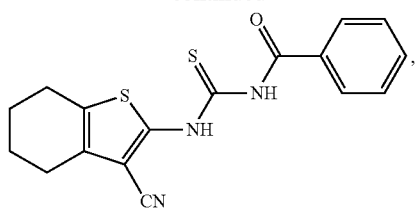
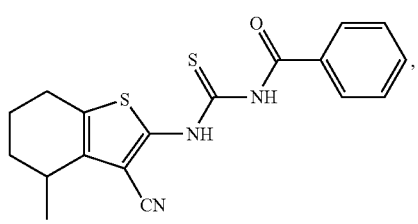
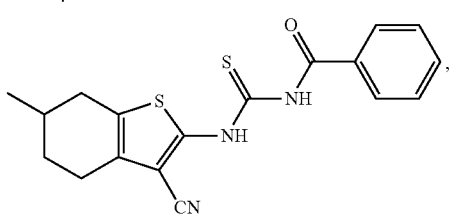
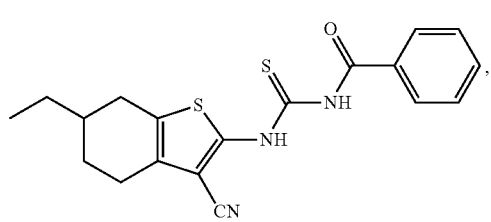
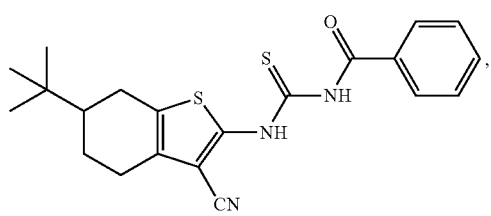
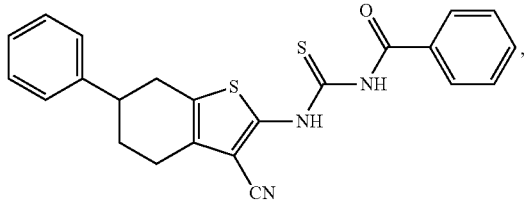
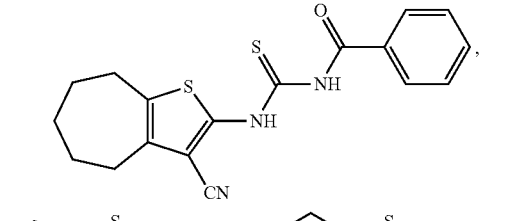
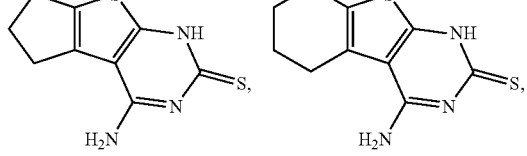
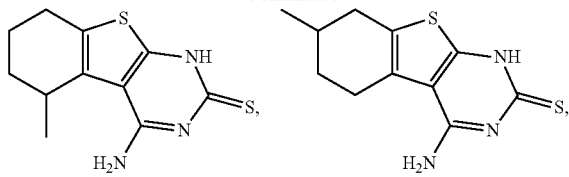
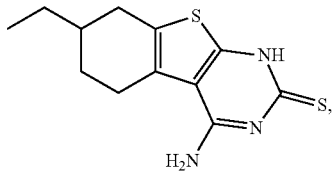
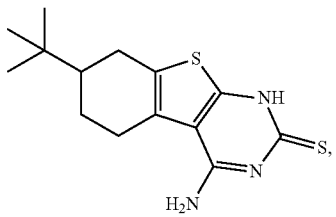
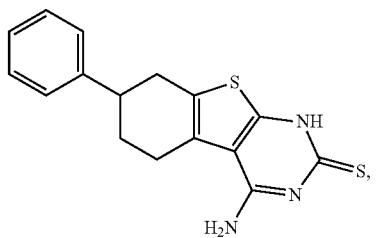
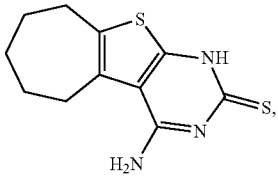
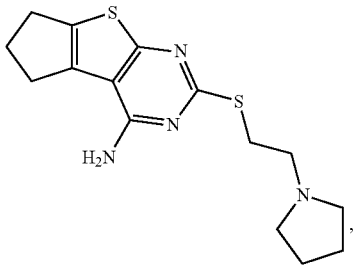
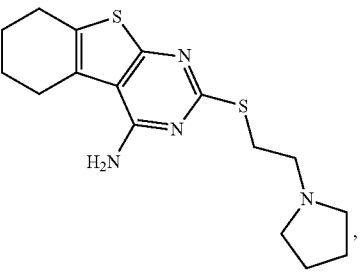

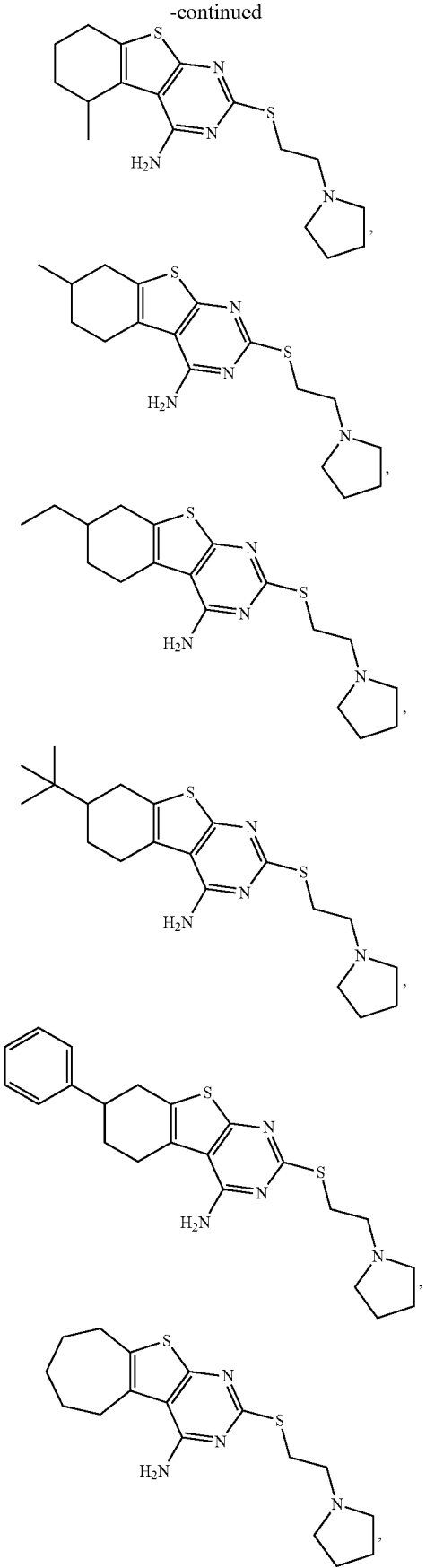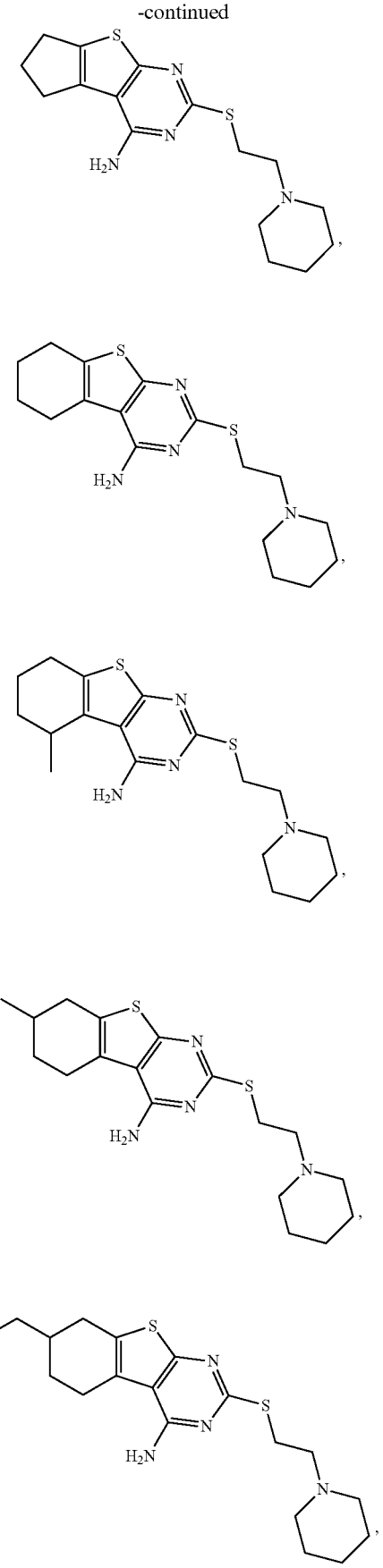

31
-continued
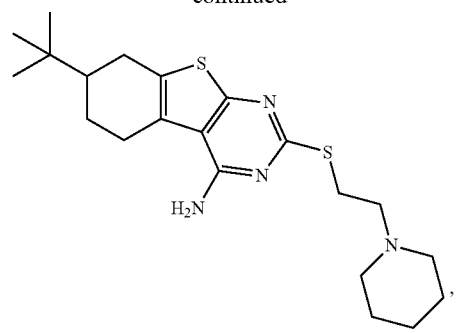
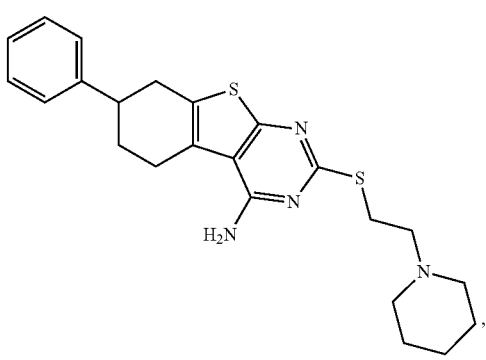
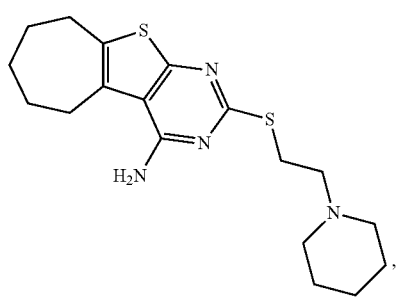
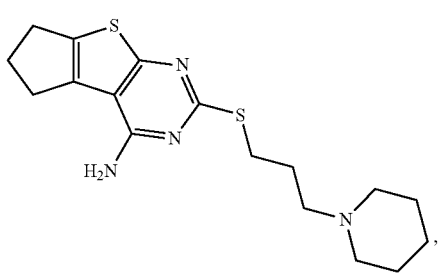
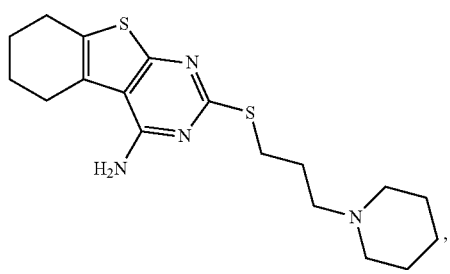
32
-continued
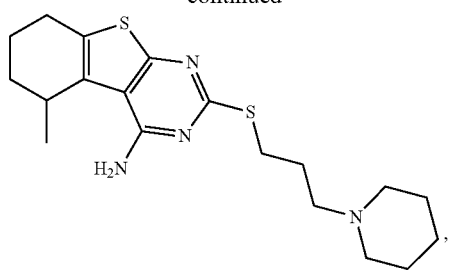
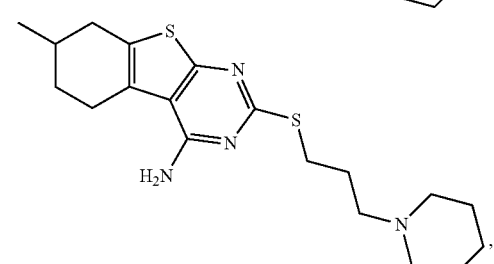
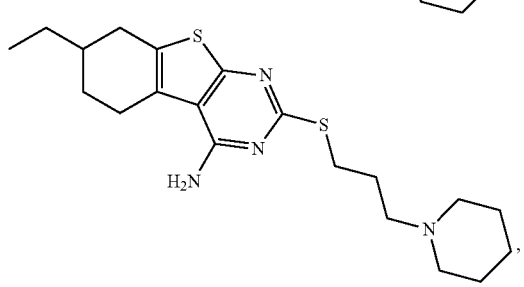
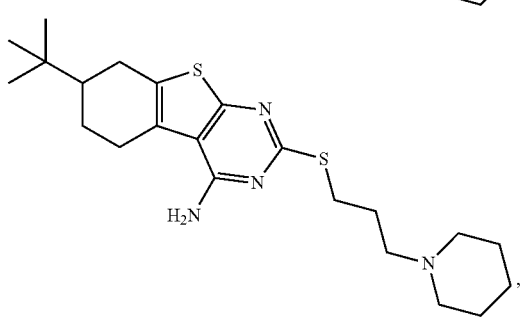
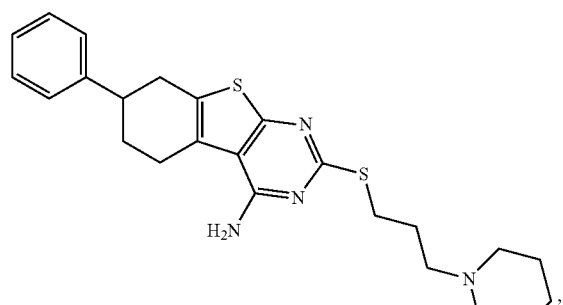
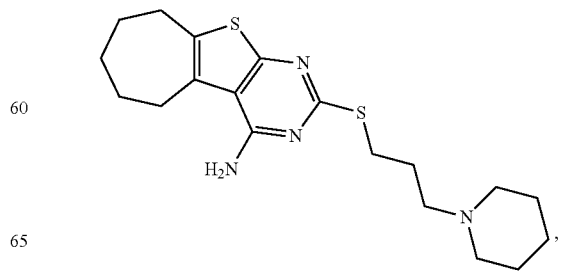

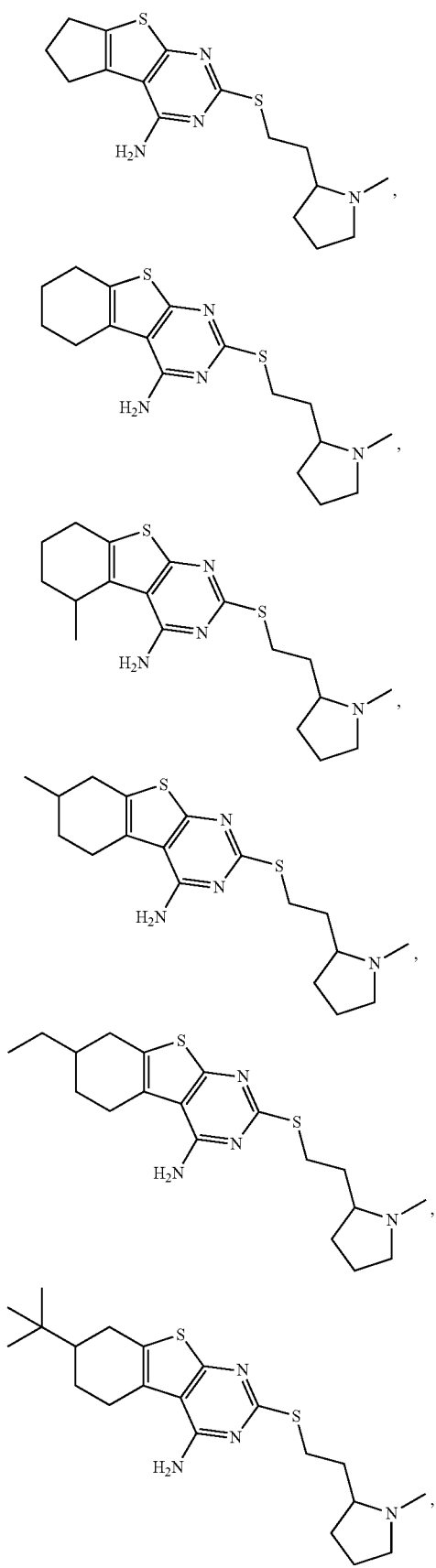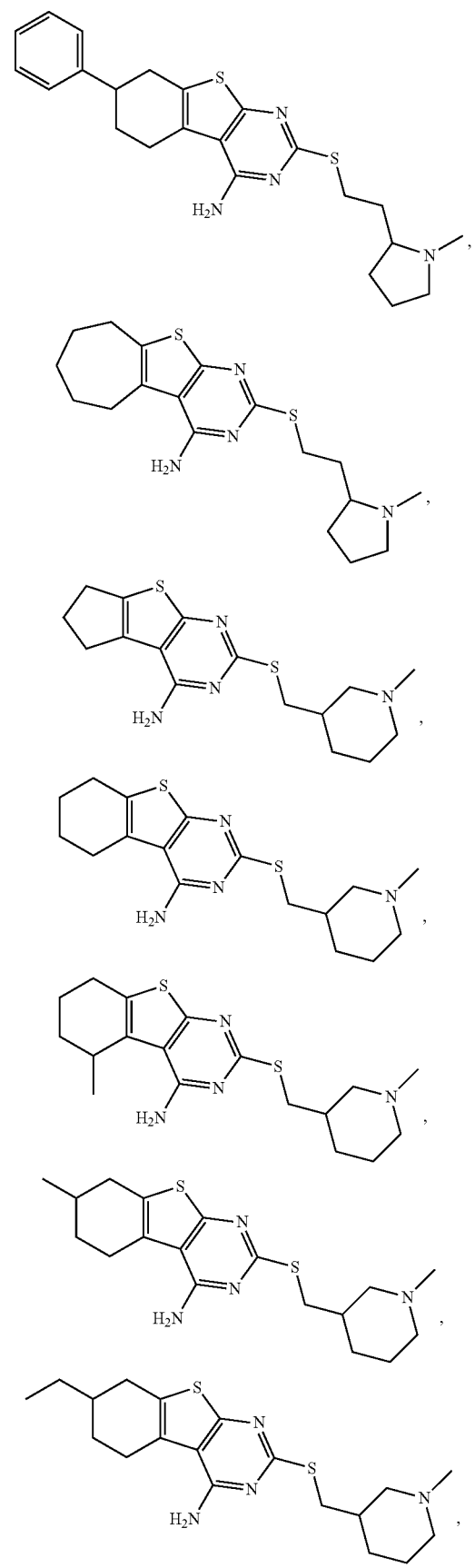

35
-continued
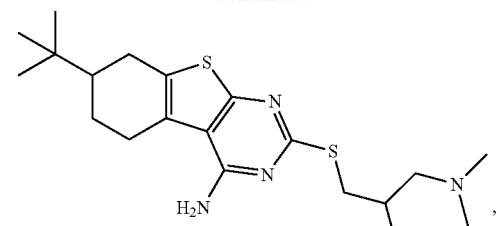
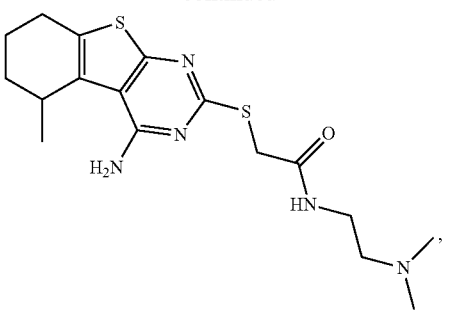
36
-continued
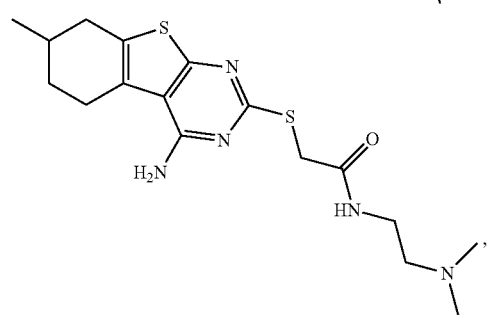
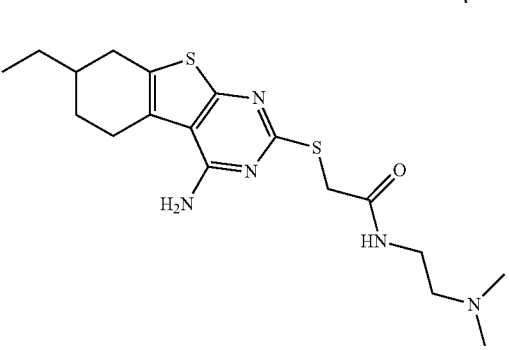
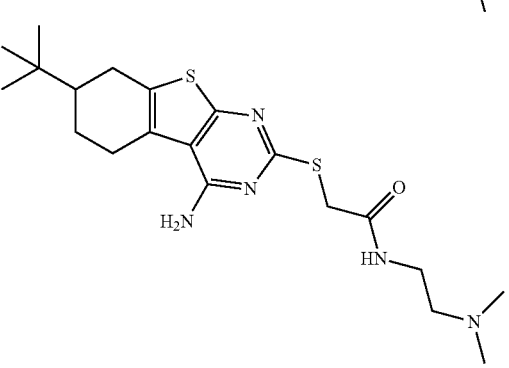
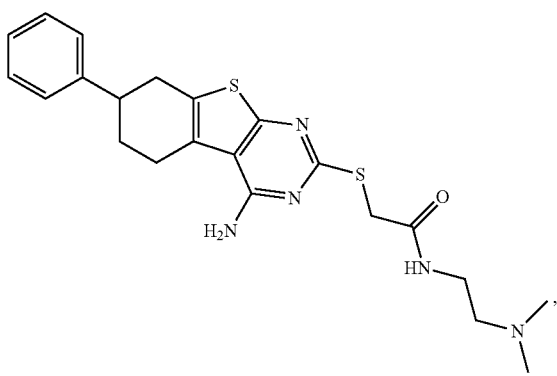

37
-continued
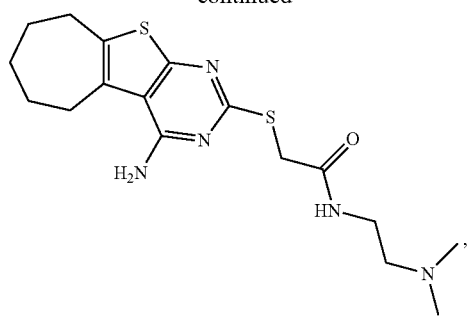
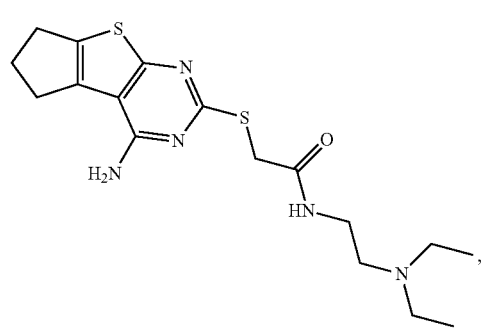
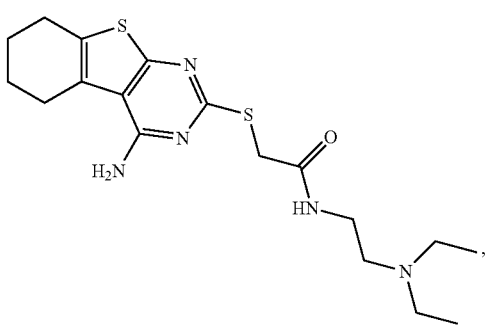
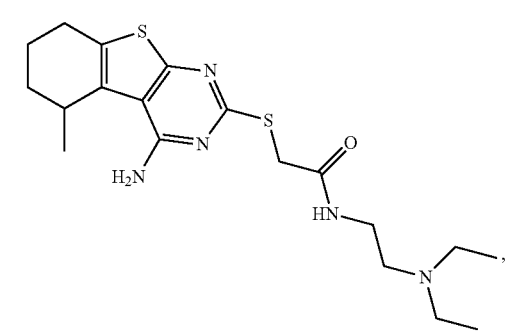
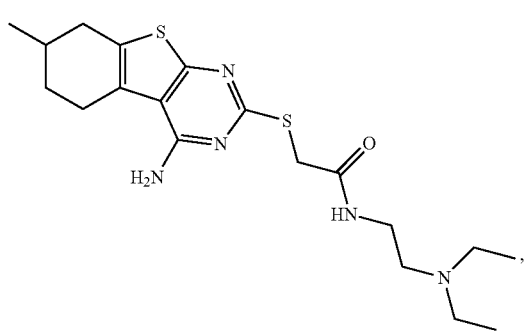
38
-continued
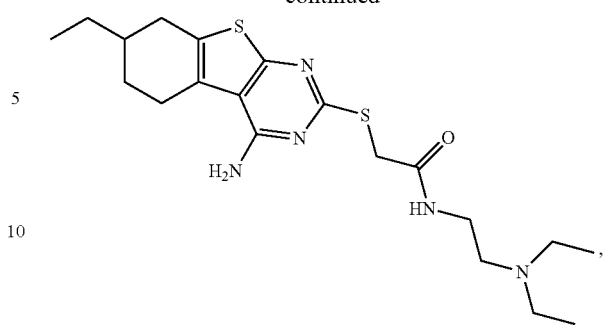
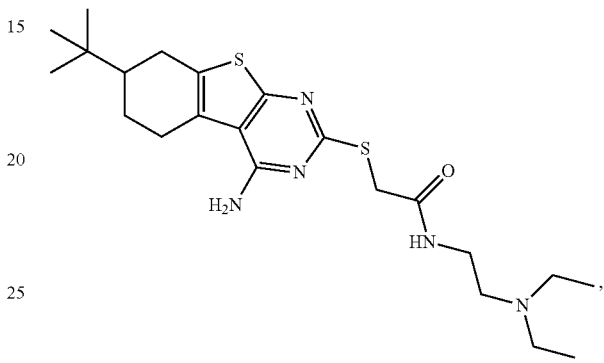
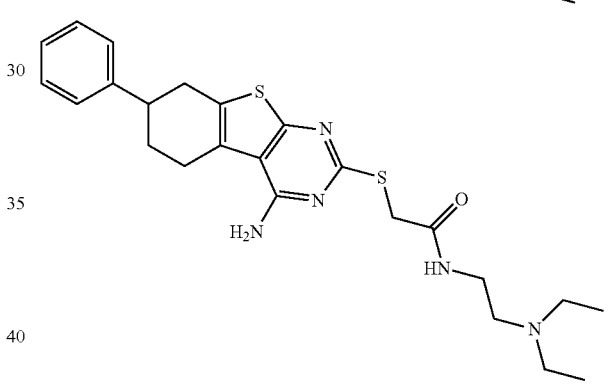
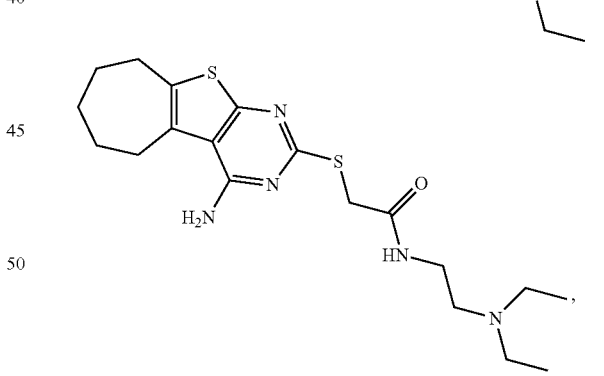

-continued
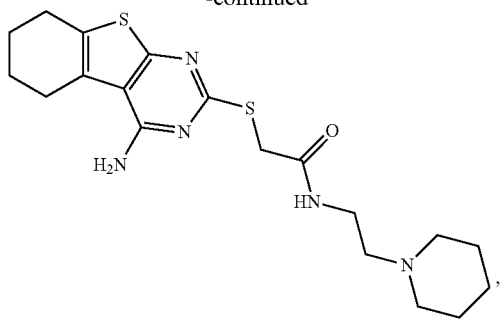
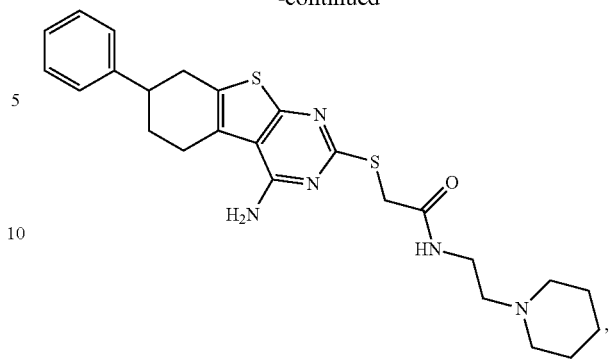
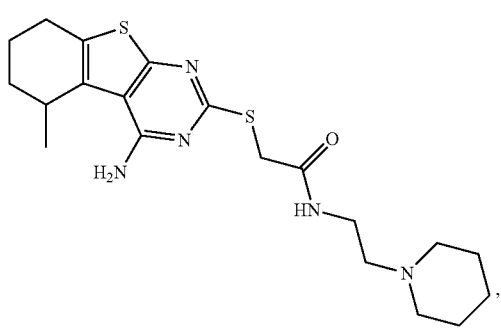
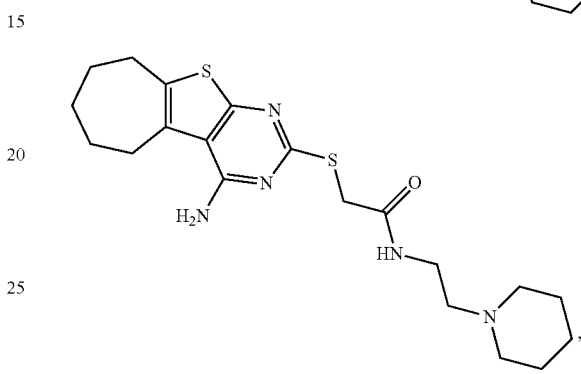
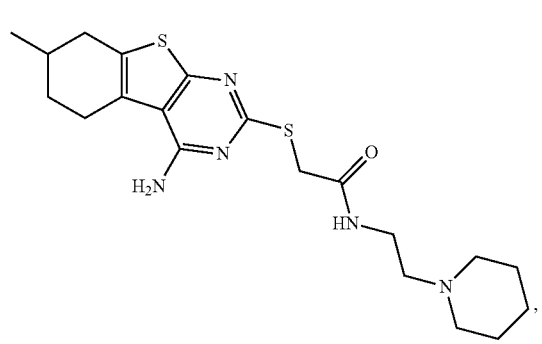
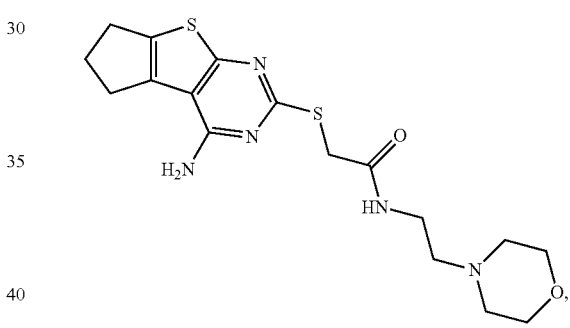
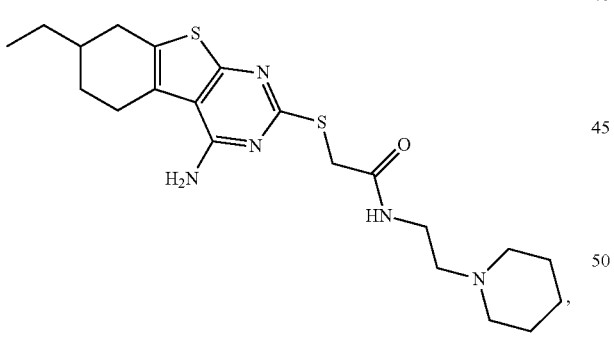
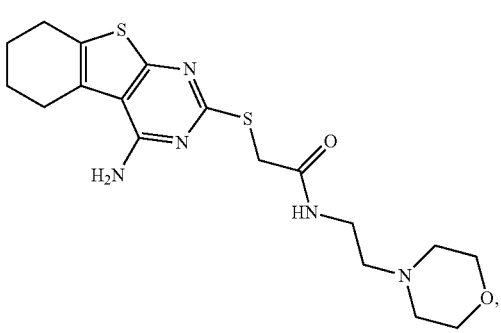
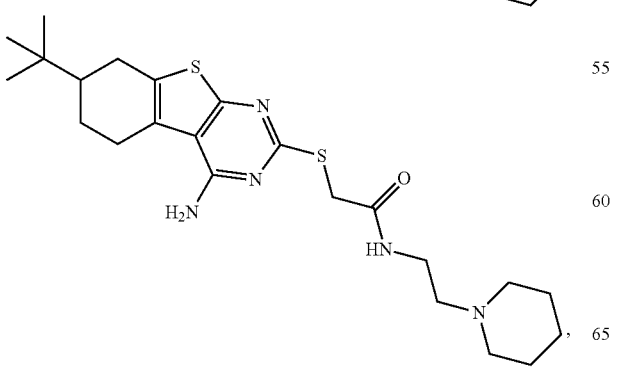
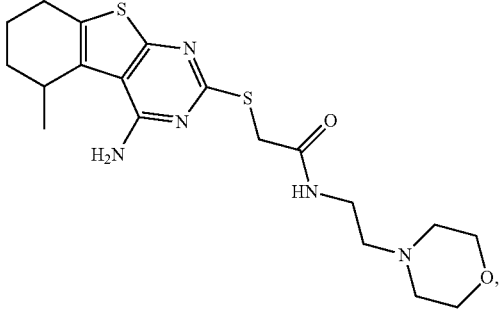

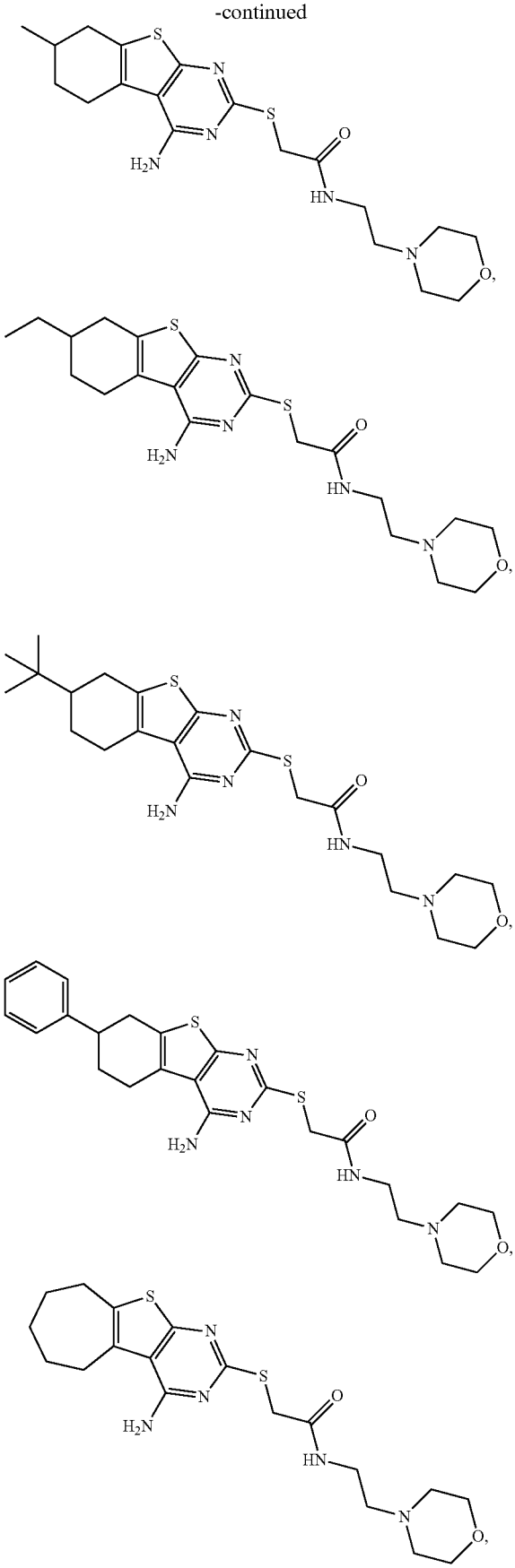

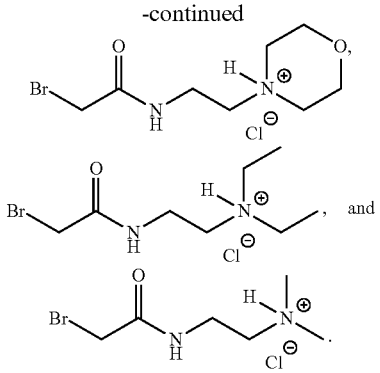

The presently-disclosed subject matter further includes methods or inhibiting Eis and methods of treating aminoglycoside-resistant Mtb. In some embodiments the method involves administering a compound or composition as disclosed herein. In some embodiments, the method involves administering a compound or composition to a subject in need of treatment for aminoglycoside-resistant Mtb. In some embodiments, the method further includes administering an aminoglycoside. In some embodiments the aminoglycoside is kanamycin (KAN).

The presently-disclosed subject matter further includes composition that include at least one compound disclosed herein as an Eis inhibitor, and an aminoglycoside. In some embodiments the aminoglycoside is kanamycin (KAN).

The presently-disclosed subject matter further includes kits comprising at least one compound disclosed herein as an Eis inhibitor, packaged together with an aminoglycoside. In some embodiments the aminoglycoside is kanamycin (KAN).

The presently disclosed subject matter includes identified potent inhibitors of Eis enzymatic activity with resulting sensitization of KAN-resistant Mtb cells, in which the resistance to KAN is caused by Eis upregulation. The inhibitors bind in the AG binding pocket blocking the access of AGs to the active site of the enzyme. The inhibitor binding is accompanied by induced-fit conformational changes of the protein. These compounds have a great potential for further development as KAN adjuvants in Mtb.

The presently-disclosed subject matter includes novel small molecule compositions, and small molecule compositions useful as inhibitors of Eis enzymatic activity. In some embodiments, the inhibitors can effectively overcome kanamycin resistance in strains of Mtb.

The presently-disclosed subject matter further includes a pharmaceutical composition including a small molecule, as described herein, and a suitable pharmaceutical carrier. The presently-disclosed subject matter also includes a method of treating a bacterial infection comprising administering to an individual an effective amount of a small molecule Eis inhibitor, as disclosed herein. In some instances, the pharmaceutical composition is administered with an aminoglycoside. In some instances the aminoglycoside is Kanamycin.

Methods of treating kanamycin resistance are also disclosed herein, comprising administering a small molecule composition disclosed herein. Also provided are methods of treating tuberculosis comprising administering the Eis inhibitors disclosed herein with kanamycin.

In some embodiments, a method is provided for treating antibiotic resistance and/or inhibiting Eis enzymatic activity in a cell. In some embodiment the method includes contacting the cell with compounds disclosed herein. The term "contacting" as used herein refers to any means by which the compound is brought into sufficient proximity and/or in direct contact with a cell such that the cell is capable of receiving the compound. For instance, in some embodiments contact refers to coating or otherwise exposing a cell to the compound. In some embodiments contact refers to culturing a cell in a solution that includes the compound. In other embodiments the cell is within a subject, and contact refers to administering a compound to the subject such that a cell within the subject is capable of receiving the novel small molecule compounds. In some embodiments, such methods can include further administration of an antibiotic at the same time as the administration of the compound, or prior to or subsequent to the administration of compound. In some embodiments, the antibiotic is kanamycin. The presently-disclosed subject matter further includes composition that include at least one compound disclosed herein as an Eis inhibitor, and an aminoglycoside. In some embodiments the aminoglycoside is kanamycin (KAN). In some embodiments, the cell exhibits resistance to kanamycin. In some embodiments, said cell is within a subject diagnosed with tuberculosis.

While the following terms used herein are believed to be well understood by one of ordinary skill in the art, definitions are set forth to facilitate explanation of the presently-disclosed subject matter.

The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

Unless otherwise indicated, the term "administering" is inclusive of all means known to those of ordinary skill in the art for providing a preparation to a subject, including administration by inhalation, nasal administration, topical administration, intravaginal administration, ophthalmic administration, intraaural administration, intracerebral administration, intravitreous administration, intracameral administration, posterior sub-Tenon administration, posterior juxtascleral administration, subretinal administration, suprachoroidal administration, cell-based administration or production, rectal administration, and parenteral administration, including injectable such as intravenous administration, intra-arterial administration, intramuscular administration, and/or subcutaneous administration. Administration can be continuous or intermittent. A preparation can be administered therapeutically; that is, administered to treat an existing condition of interest. A preparation can be administered prophylactically; that is, administered for prevention of a condition of interest.

In some embodiments a subject will be administered an effective amount of at least one compound and/or composition provided in the present disclosure. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

In some embodiments the subject in need thereof will be suffering or will have been diagnosed tuberculosis and/or related diseases, disorders, pathologies, or conditions.

As used herein, the terms "treatment" or "treating" relate to any treatment of a condition of interest, including but not limited to prophylactic treatment and therapeutic treatment. As such, the terms treatment or treating include, but are not limited to: preventing a condition of interest or the development of a condition of interest; inhibiting the progression of a condition of interest; arresting or preventing the development of a condition of interest; reducing the severity of a condition of interest; ameliorating or relieving symptoms associated with a condition of interest; and causing a regression of the condition of interest or one or more of the symptoms associated with the condition of interest.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "an enzyme" includes a plurality of such enzymes, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±5%, in some embodiments ±1%, in some embodiments ±0.5%, in some embodiments ±0.1%, and in some embodiments ±0.01% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As will be recognized by one of ordinary skill in the art, the terms "reduce", "reducer", "reduction", "reducing", "suppression," "suppressing," "suppressor," "inhibition," "inhibiting" or "inhibitor" do not refer to a complete elimination of angiogenesis in all cases. Rather, the skilled artisan will understand that the term "reducing", "suppressing" or "inhibiting" refers to a reduction or decrease in a particular condition. Such reduction or decrease can be determined relative to a control. In some embodiments, the reduction or decrease relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

As described herein, the presently-disclosed subject matter further includes pharmaceutical compositions comprising at least one enzyme described herein together with a pharmaceutically acceptable carrier.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compositions can be formulated as eye drops. For example, the pharmaceutically acceptable carrier may comprise saline solution or other substances used to formulate eye drop, optionally with other agents. Thus, eye drop formulations permit for topical administration directly to the eye of a subject.

The compositions can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds can also be formulated in rectal compositions, creams or lotions, or transdermal patches.

The presently-disclosed subject matter further includes a kit that can include an enzyme and/or a pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

The presently-disclosed subject matter includes novel small molecules. Also disclosed are small molecules that inhibit Eis. Small molecule Eis inhibitors disclosed herein aid in reducing KAN resistance and/or restoring KAN susceptibility in *Mycobacterium tuberculosis*. The presently-disclosed subject matter further includes a pharmaceutical composition including a small molecule inhibitor, as described herein, and a suitable pharmaceutical carrier, optionally administered with Kanamycin. The presently-disclosed subject matter further includes a method of treating tuberculosis, including aminoglycoside resistant tuberculosis, comprising administering to an individual an effective amount of a small molecule Eis inhibitor, as disclosed herein, to inhibit the Eis acetyltransferase of *Mycobacterium tuberculosis* and reduce KAN resistance and/or restore KAN susceptibility.

In certain embodiments, the present disclosure further provides a method of treating, preventing and/or reducing kanamycin resistance and/or restoring KAN susceptibility in *Mycobacterium tuberculosis*. The method comprises at least the step of administering an effective amount of a small molecule inhibitor provided in the present disclosure to a subject. In some embodiments, the subject is in need of treatment. In some instances, the *Mycobacterium tuberculosis* strain is Mtb K204 or H37Rv. In some embodiments, the small molecule is administered with an aminoglycoside, for example, kanamycin. In some embodiments, the treatment reduces and/or eliminates the Eis-mediated KAN resistance of *Mycobacterium tuberculosis*.

Additionally, in certain embodiments, the inhibitors of the present disclosure have a Mtb strain K204 $MIC_{KAN}$ value of less than about 5.0 μg/mL, of less than about 2.5 μg/mL, or less than about 1.25 μg/mL. In other embodiments, the inhibitors have a $MIC_{KAN}$ value of less than about 0.625 μg/mL for *Mycobacterium tuberculosis* (Mtb) strain H37Rv.

The presently-disclosed subject matter is further illustrated by the following specific but non-limiting examples. The following examples may include compilations of data that are representative of data gathered at various times during the course of development and experimentation related to the present invention.

EXAMPLES

Example 1

This Example related to Eis inhibitors having the following scaffolds: the methyl 4H-furo[3,2-b]pyrrole-5-carboxylate (scaffold 1) and the 3-(1,3-dioxolano)-2-indolinone (scaffold 2) identified by high-throughput screening HTS, the synthesis of 13 and 14 analogues of these scaffolds, respectively, and their biochemical and biological testing.

First, we screened ~123,000 small molecules for inhibition of KAN acetylation by Eis_Mtb. The HTS yielded two promising scaffolds 1 and 2 (FIG. 1). Sixty compounds containing scaffold 1 (FIG. 2) were present in the HTS library. In these sixty compounds, the pyrrole ring was decorated with different groups including alkyl chains, aryl and oxazole rings, as well as amides. Fifty-nine of these scaffold 1 molecules did not inhibit Eis_Mtb, however compound 1a (FIG. 1, also labeled as 4kk in FIG. 2) displayed some inhibition in the HTS. Because 1a contained an aryl ketone group, we opted to synthesize 1a along with 12 additional analogues (1b-1m) comprised of different aryl groups (FIG. 1). For scaffold 2, ten compounds with different groups attached to the indolinone ring were in the HTS library (FIG. 3). A hydrogen (8a), an alkyl (8b), an alkyl ketone (8c), a carboxylic acid (9a), or an amide (9b) substituent resulted in no Eis_Mtb inhibitory activity. Similarly to the scaffold 1 analogues, aryl ketones of scaffold 2 (8f-8h) displayed Eis_Mtb inhibition, with the exception of the trifluoromethyl substituted aryl ketones (8d and 8e). Three compounds synthesized from scaffold 2 (8f-8h, FIG. 3) were found to be active. These and 11 of their analogues containing different aryl substituents for further study (Note: 8f-8h are numbered 2g-2i in FIG. 1 to represent the scaffold 2 series).

Compound 1a and 12 analogues (1b-1m) as well as 14 analogues for scaffold 2 (2a-2n) with different R substituents were synthesized for structure-activity-relationship (SAR) analysis of Eis_Mtb inhibition in vitro and in cellulo (FIG. 1). All new compounds were characterized by $^{1}H$, $^{13}C$ NMR (FIGS. S5-S56), mass spectrometry, and were established to be ≥95% pure by HPLC prior to further testing.

TABLE 1

$IC_{50}$ values against purified Eis_Mtb and MIC values against Mtb H37Rv and Mtb K204 with the compounds at the concentrations specified.

| Cpd | $IC_{50}$ (μM)$^a$ | Concentration tested (μM)$^b$ | H37Rv $MIC_{KAN}$ (μg/mL)$^c$ | K204 $MIC_{KAN}$ (μg/mL)$^d$ |
|---|---|---|---|---|
| — | — | | ≤1.25 | ≥10, 10 |
| 1a | 3 ± 1 | 100 | ≤1.25 | 5, 10 |
| 1b | 2.9 ± 0.9 | 100 | ≤1.25 | 10, 10 |
| 1c | 0.16 ± 0.07 | 15.5 | ≤1.25 | 10, 10 |
| 1d | 0.25 ± 0.08 | 25.1 | ≤1.25 | ≥10, 10 |
| 1e | 0.5 ± 0.2 | 52.6 | ≤1.25 | ≥10, 10 |
| 1f | >200 | 100 | ≤1.25 | ≥10, 10 |
| 1g | 0.3 ± 0.1 | 33.9 | ≤1.25 | 10, 10 |
| 1h | 0.6 ± 0.3 | 64.5 | ≤1.25 | 10, ≥10 |
| 1i | >200 | 100 | ≤1.25 | ≥10, ≥10 |
| 1j | 5.8 ± 1.8 | 100 | ≤1.25 | 5, 10 |
| 1k | >200 | 100 | ≤1.25 | 10, 10 |
| 1l | >200 | 100 | ≤1.25 | ≥10, 10 |
| 1m | >200 | 100 | ≤1.25 | ≥10, 10 |
| 2a | 0.33 ± 0.16 | 32.6 | ≤1.25 | 5, 5 |
| 2b | 23 ± 10 | 100 | ≤1.25 | 10, 10 |
| 2c | 0.30 ± 0.08 | 29.7 | ≤1.25 | 5, 2.5 |
| 2d | 0.015 ± 0.005 | 1.5 | ≤1.25 | ≥10, 10 |

TABLE 1-continued IC$_{50}$ values against purified Eis_Mtb and MIC values against
Mtb H37Rv and Mtb K204 with the compounds at the
concentrations specified.

| Cpd | IC$_{50}$ (μM)$^a$ | Concentration tested (μM)$^b$ | H37Rv MIC$_{KAN}$ (μg/mL)$^c$ | K204 MIC$_{KAN}$ (μg/mL)$^d$ |
|---|---|---|---|---|
| 2e | 0.54 ± 0.25 | 54.2 | ≤1.25 | 10, 5 |
| 2f | >200 | 100 | ≤1.25 | ≥10, 10 |
| 2g | 0.09 ± 0.03 | 8.9 | ≤1.25 | 5, 5 |
| 2h | 2.2 ± 0.7 | 100 | ≤1.25 | 10, 5 |
| 2i | >200 | 100 | ≤1.25 | ≥10, 10 |
| 2j | 8.7 ± 2.2 | 100 | ≤1.25 | 5, 10 |
| 2k | >200 | 100 | ≤1.25 | 10, 10 |
| 2l | >200 | 100 | ≤1.25 | ≥10, 10 |
| 2m | >200 | 100 | ≤1.25 | ≥10, 10 |
| 2n | 1.2 ± 0.4 | 100 | ≤1.25 | 10, 5 |

$^a$IC$_{50}$ against purified Eis_Mtb enzyme,
$^b$Concentrations of Eis inhibitor in the MIC assays. At these concentrations, these compounds did not inhibit the growth of Mtb H37Rv or that of Mtb K204 when tested in the absence of KAN. Concentrations of Eis inhibitors were 100x their IC$_{50}$ when IC$_{50}$ <1 μM, or 100 μM for IC$_{50}$ >1 μM.
$^c$Activity of KAN against Mtb H37Rv.
$^d$Activity of KAN against Mtb K204.
For $^c$ and $^d$, results are from two experiments.

Figure 5:
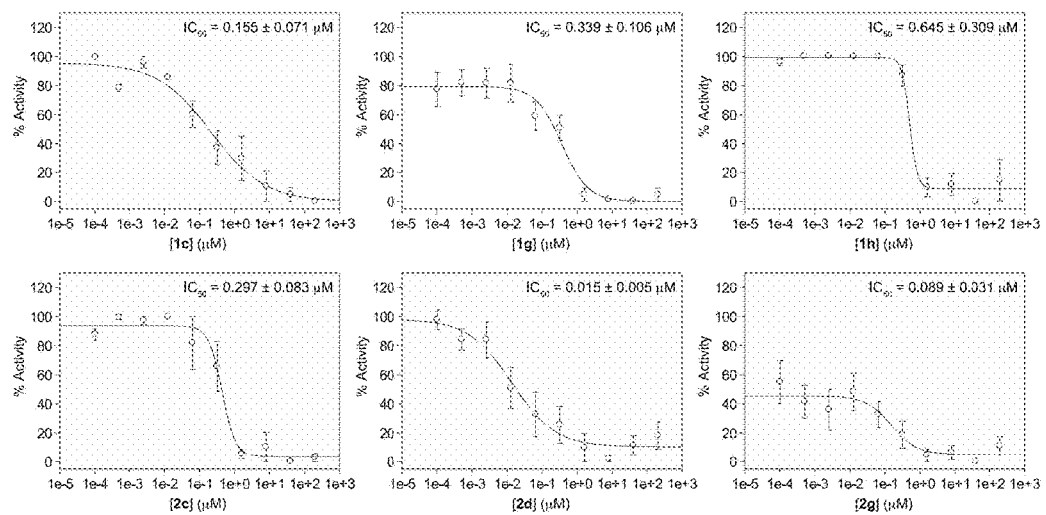
FIG. 5 includes representative $IC_{50}$ curves for exemplary compounds according to the scaffolds set forth in FIG. 1.

We evaluated biochemical (inhibition (IC$_{50}$) of purified Eis_Mtb enzyme) and biological (effect on the KAN MIC values for KAN-sensitive Mtb H37Rv and KAN-resistant Mtb K204 cells) properties of these compounds, in parallel (Table 1; FIG. 5). The freshly synthesized 1a, which displayed some inhibition of Eis_Mtb in the HTS campaign, was confirmed to be a good Eis_Mtb inhibitor in vitro (IC$_{50}$=3±1 μM). In the presence of 1a, KAN displayed an MIC of 5-10 μg/mL against Mtb K204. Having confirmed the weak inhibitory activity of 1a, we explored the effect of substitution on the phenyl ring on the aryl ketone part of scaffold 1. Ortho substitution, as in 1b with a o-fluoro substituent, resulted in almost the same Eis_Mtb inhibitory activity (IC$_{50}$=2.9±0.9 μM) as that for the parent 1a. KAN MIC against Mtb K204 was unaffected by 1b (MIC$_{KAN}$=10 μg/mL). To establish if meta or para substitution would be more favorable than ortho substitution, we generated compounds 1c-1j. For both meta and para substitutions, bulkier substituents led to weaker Eis_Mtb inhibition (IC$_{50}$>200 μM for m-methoxy (1f) and p-bromo (1i) compared to IC$_{50}$=0.16±0.07 and 0.3±0.1 μM for m-fluoro (1c) and p-fluoro (1g), respectively). Most of these derivatives (1c-1i) did not improve KAN activity against Mtb K204. The p-methyl derivative 1j displayed almost the same Eis_Mtb inhibitory activity (IC$_{50}$=5.8±1.8 μM) and MIC value against Mtb K204 as that of 1a. We generated 1k (naphthyl substituted) with the hope of strengthening any possible π-π interaction between the inhibitor and the AG-binding site of the Mtb Eis. This compound was found to be completely inactive (IC$_{50}$>200 μM and MIC$_{KAN}$=10 μg/mL against Mtb K204). Finally, replacing the phenyl ring with alkyl chains (ethyl (1l) and t-butyl (1m)) did not improve the Eis inhibition or MIC$_{KAN}$ for K204 Mtb.

For scaffold 2, compound 2g-2i, which displayed Eis_Mtb inhibition in the HTS, were freshly synthesized. The p-fluoro substituted 2g displayed good Eis inhibitory activity (IC$_{50}$=0.09±0.03 μM) and when used in combination with KAN resulted in MIC$_{KAN}$ of 5 μg/mL against K204 Mtb. The p-chloro substituted 2h was less active (IC$_{50}$=2.2±0.7 μM) than the p-fluoro substituted 2g and did not sensitize Mtb K204 to KAN (MIC$_{KAN}$=5-10 g/mL). The p-bromo substituted 2i was found to be completely inactive (IC$_{50}$>200 μM and MIC$_{KAN}$≥10 μg/mL against Mtb K204), while it displayed limited Eis inhibition in the HTS, which could indicate that the compound in the HTS library was not completely pure. We also found that the p-methyl derivative 2j displayed a 100-fold decrease in Eis inhibitory activity (IC$_{50}$=8.7±2.2 μM) from 2g and in combination with KAN resulted in almost the same KAN MIC (5-10 μg/mL) against KAN-resistant Mtb as 2g did. The non-substituted counterpart of parent 2g, derivative 2a, displayed weaker Eis inhibitory activity (IC$_{50}$=0.33±0.16 μM) and improved the activity of KAN against Mtb K204 (MIC$_{KAN}$=5 μg/mL). We also synthesized the m-fluoro, m-chloro, and m-bromo derivatives 2c, 2d, and 2e. The m-chloro substituted 2d showed the same inhibitory activity as that of 2g, but did not sensitize Mtb K204 to KAN (MIC$_{KAN}$≥10 μg/mL). The m-fluoro and m-bromo substituted 2c and 2e resulted in a 3- and 5-fold worse Eis inhibitory activity (IC$_{50}$=0.30±0.08 and 0.54±0.25 μM), respectively. When used with the m-bromo-substituted 2e, KAN had an MIC of 5-10 μg/mL against Mtb K204. However, when used with the m-fluoro substituted 2c, KAN displayed a better MIC value of 2.5-5 μg/mL. As observed with scaffold 1, the presence of m-methoxy-phenyl, naphthyl, ethyl, and t-butyl groups in scaffold 2 resulted in molecules that were completely inactive (IC$_{50}$>200 μM and MIC$_{KAN}$≥10 μg/mL against Mtb K204). For scaffold 2, we also synthesized a m-nitro substituted compound (2n) to investigate the potential effect of a strong electron-withdrawing group on Eis inhibitory activity. Compound 2n was less active (IC$_{50}$=1.2±0.4 μM) than 2g, but it sensitized Mtb K204 to KAN (MIC$_{KAN}$=5-10 μg/mL). The absence of antibacterial activity of these compounds when used alone along with a general correlation between IC$_{50}$ and MIC values indicated that inhibition of Eis by these compounds is the main mechanism of sensitization to KAN.

To investigate the selectivity of our inhibitors towards Eis_Mtb, we tested two of our derivatives, one from each series, 1c and 2c, against three other AAC enzymes with different acetylation regiospecificities: AAC(2')-Ic from Mtb,[5] AAC(3)-IV from E. coli,[12] and AAC(6')-Ie/APH(2")-Ia from Staphylococcus aureus.[13] Similarly to other known non-Eis AACs, these three enzymes were previously shown to be strictly regiospecific, but, like Eis, each enzyme was capable of acetylating structurally distinct AGs.[40] Neither 1c nor 2c inhibited KAN acetylation by these three AACs at concentrations as high as 200 μM, which indicated that our compounds were highly selective against Eis_Mtb.

Figure 4:
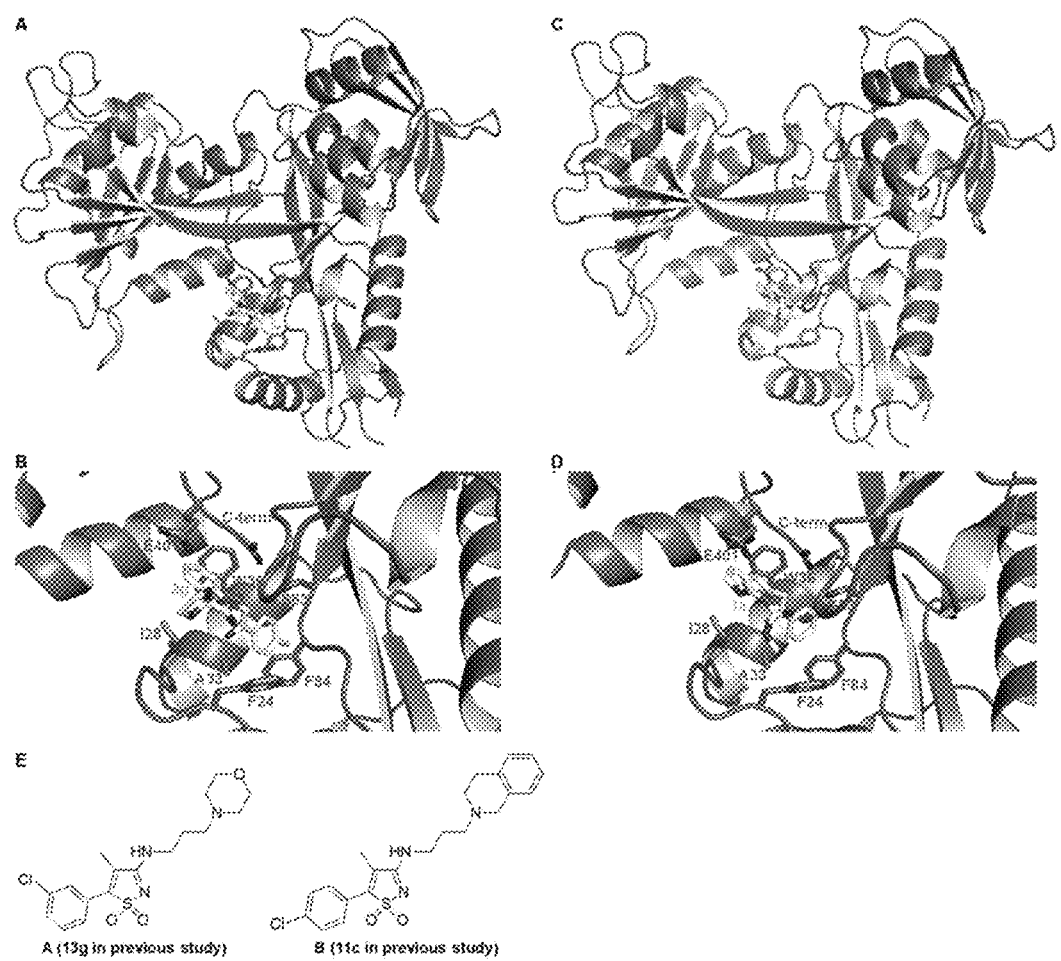
FIG. 4 includes five panels, including models of compound 2g (panels A and B) and 1a (panels C and D) in complex with a monomer of Eis_Mtb (panels A and C) or in complex with Eis (panels B and D), and the structures of compounds A and B (panel E) that were used to model compounds 2g and 1a in the active site of Eis.

To explain the results of our SAR study, we used previously published crystal structures of ternary Eis_Mtb-CoA-compound A (13g in ref[14]; PDB ID 5EC4) and B (11c in ref[14]; PDB ID 5EBV) complexes to model our inhibitors 1a and 2g in a position similar to that of inhibitors A and B (FIG. 4). Without the crystal structures, de novo computational modeling of and screening for Eis inhibitors, including pharmacophore-based computer modeling, are invalidated by significant conformational changes in the Eis active site upon inhibitor binding.[13] The inhibitors occupy the site overlapping with the AG-binding site of Eis. The models show that the cores of inhibitors 1a and 2g are surrounded by the side chains of hydrophobic amino acid residues (Trp36, the aliphatic part of Glu401, Ile28, Phe24, and Val400). The cores stack with the indole of Trp36, and in the orthogonal direction they are sandwiched between Glu401, the Eis C-terminus on one side and Ile28 on the other. The acetophenone rings of both series 1 and 2 with different substituents stack with Phe84, explaining why replacing these aromatic rings with alkyl chains resulted in a loss of activity for 1l, 1m, 2l, and 2m. The acetophenone rings are also surrounded by several hydrophobic amino acid residues (Phe84, Trp36, Met65, Ala33). Therefore putting a polar methoxy group in this hydrophobic environment would likely destabilize Eis binding, explaining the $IC_{50}$ values of >200 µM for 1f and 2f. The para position of the acetophenone rings is flanked by Phe84 and Trp36, and it is ~5 Å away from Trp13 and Met65, explaining why the bulkier bromo substituents of 1i and 2i resulted in lower Eis inhibitory activity, whereas the small fluoro substituents of 1 g and 2g improved Eis inhibitory activity. The ortho position of the acetophenone rings is flanked by Phe402, explaining why an ortho substituent, as in 1b and 2b, resulted in a loss of Eis inhibition. The models shows that there is space for small substitution in the meta position of the acetophenone rings (a ~5 Å-gap). Small substituents such as the fluoro and chloro of 1c, 1d, 2c and 2d fit well in the cavity, explaining why these compounds displayed good Eis inhibition. However, bulkier substituents such as the bromo of 1e and 2e or the nitro of 2n are too big to be accommodated at this site and would clash with Eis residues, accounting for the poor Eis inhibition by these compounds. We also determined that the calculated Log P values of all compounds are in the desirable range (0.98-3.75).

In sum, we have discovered two scaffolds with Eis inhibitory activity. From 27 synthesized analogues of these scaffolds with the variable acetophenone appendage, we identified potent inhibitors of Eis. Growth inhibition studies of our inhibitors in combination with KAN in KAN-susceptible Mtb H37Rv ($MIC_{KAN} \leq 1.25$ µg/mL) and KAN-resistant Mtb K204 ($MIC_{KAN} \geq 10$ µg/mL) showed that some of our inhibitors were able to sensitize Mtb K204 to KAN. Smaller substituents, like hydrogen and fluorine, yielded the best compounds. In contrast, larger substituents, such as bromo or methoxy dramatically decreased the potency of the compounds. The best compound identified was 2c with the 3-(1,3-dioxolano)-2-indolinone core and a m-fluoro-phenyl substituent. This compound when used in combination with KAN reduced the $MIC_{KAN}$ for KAN-resistant Mtb to 2.5-5 µg/mL. While CLSI recommends $MIC_{KAN}$ of 5 µg/mL on Middlebrook 7H10 agar, it has no recommendation for susceptibility testing by Alamar Blue, the method used here. One study suggests a critical $MIC_{KAN}$ of 2.5 µg/mL for Alamar Blue testing. Since our inhibitors are able to return KAN-resistant isolates to an $MIC_{KAN}$ below the critical concentration, essentially making resistant Mtb isolate KAN-susceptible, such inhibitors could play a crucial role in recovering KAN as a treatment option.

Example 2

Figure 6:
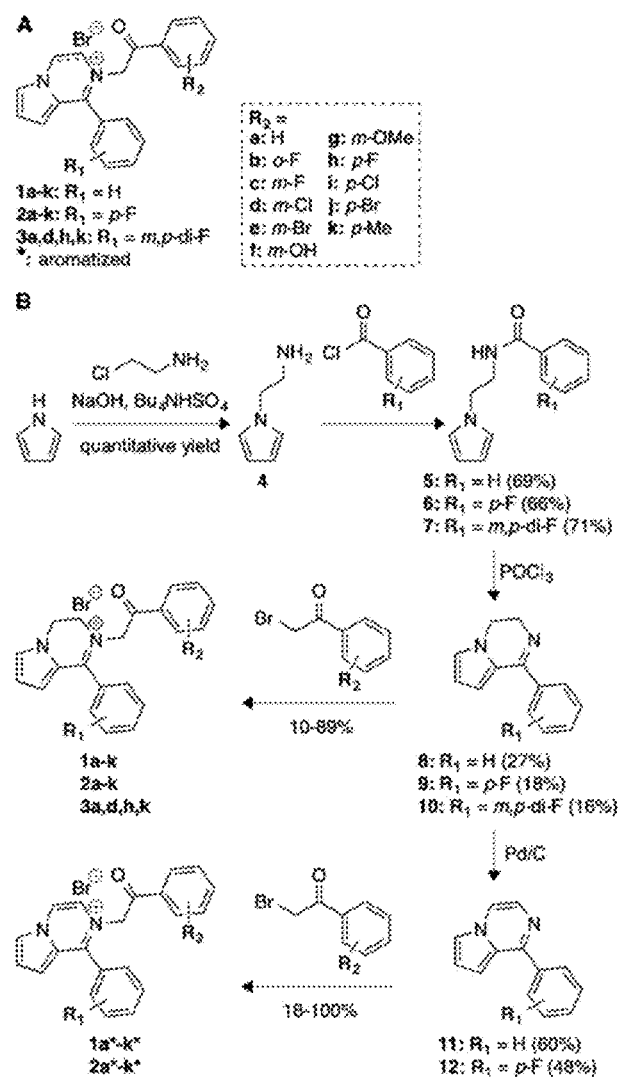
FIG. 6 includes preparation schemes and structures of exemplary Eis inhibitor scaffolds according to the presently-disclosed subject matter and discussed in Example 2.

This Example related to Eis inhibitors having the scaffolds as set forth in FIG. 6 and reports report the chemical synthesis of various compounds, along with their biochemical and biological studies. Among compounds in this series, we have generated novel and promising Eis inhibitors that not only efficiently inhibit the purified enzyme, but also restore KAN sensitivity of KAN-resistant Mtb bacteria. We also present a crystal structure of Eis in complex with CoA and one potent inhibitor (compound 2k*), which explains the structure-activity relationship (SAR).

Compound 1a* and 47 additional analogues 1a-3k with different $R_1$ and $R_2$ substituents on the two phenyl rings and either a fully aromatized (indicated by an asterisk after the compound number) or a non-aromatized pyrrolo[1,5-a]pyrazine core were generated for a thorough SAR analysis of Eis inhibition (Scheme 1B). The synthesis of all compounds started with a reaction between the commercially available pyrrole and 2-chloroethylamine, which afforded compound 4 in quantitative yield. Compound 4 was reacted with different substituted benzoyl chlorides to obtain amides 5-7 in 66-71% yields. The resulting amides were mixed with phosphorus(V) oxychloride to generate cyclized products 8-10. Then, compounds 8-10 were reacted with various substituted 2-bromoacetophenones to obtain the desired non-aromatized products 1a-k, 2a-k, and 3a,d,h,k. In order to generate the aromatized counterparts of these products, compounds 8 and 9 were first aromatized in the presence of Pd/C to generate molecules 11 and 12. Conventionally, Pd/C is a hydrogenation catalyst. In the absence of hydrogen gas, Pd/C is known to catalyze an oxidative aromatization instead of hydrogenation. More details about this heteroaromatic aromatization were summarized in an excellent review.[19] Compounds 11 and 12 were further reacted with the different substituted 2-bromoacetophenones to furnish the desired fully aromatized analogues 1a*-k* and 2a*-k*. These compounds were evaluated for Eis inhibition using the clinically relevant KAN as the AG substrate ($IC_{50}$ values in Table 2).

TABLE 2

Inhibition of Eis-catalyzed KAN acetylation ($IC_{50}$ values) by the pyrrolo[1,5-a]pyrazine derivatives as well as effect of these molecules on KAN MIC values for Mtb H37Rv and KAN-resistant Mtb K204.

| Cpd # | $R_1$ | $R_2$ | Aromatic | $IC_{50}$ (µM)[a] | H37Rv $MIC_{KAN}$ (µg/mL)[b] | K204 $MIC_{KAN}$ (µg/mL)[c] | Cpd # | $R_1$ | $R_2$ | Aromatic | $IC_{50}$ (µM)[a] | H37Rv $MIC_{KAN}$ (µg/mL)[b] | K204 $MIC_{KAN}$ (µg/mL)[c] |
|---|---|---|---|---|---|---|---|---|---|---|---|---|---|
| 1a | H | H | no | 0.9 ± 0.2 | —[d] | —[d] | 2a | p-F | H | no | 0.47 ± 0.05 | —[d] | —[d] |
| 1b | H | o-F | no | 0.7 ± 0.2 | —[d] | —[d] | 2b[e] | p-F | o-F | no | 1.4 ± 0.4 | —[d] | —[d] |
| 1c | H | m-F | no | 0.05 ± 0.01 | ≤1.25 | 10, 10 | 2c | p-F | m-F | no | 0.7 ± 0.2 | —[d] | —[d] |
| 1d | H | m-Cl | no | 0.5 ± 0.1 | ≤1.25 | 10, 10 | 2d | p-F | m-Cl | no | 0.15 ± 0.04 | ≤1.25 | >10, >10 |
| 1e | H | m-Br | no | 0.44 ± 0.16 | ≤1.25 | 10, 10 | 2e | p-F | m-Br | no | 0.07 ± 0.02 | ≤1.25 | >10, >10 |
| 1f[e] | H | m-OH | no | 4.2 ± 1.7 | —[d] | —[d] | 2f[e] | p-F | m-OH | no | 8.7 ± 1.6 | —[d] | —[d] |
| 1g | H | m-OMe | no | 0.15 ± 0.04 | ≤1.25 | 10, 10 | 2g[e] | p-F | m-OMe | no | 1.3 ± 0.4 | —[d] | —[d] |
| 1h | H | p-F | no | 0.039 ± 0.007 | ≤1.25 | 10, 10 | 2h | p-F | p-F | no | 0.23 ± 0.02 | ≤1.25 | 10, 5 |
| 1i | H | p-Cl | no | 0.31 ± 0.09 | ≤1.25 | 5, 5 | 2i | p-F | p-Cl | no | 0.5 ± 0.1 | —[d] | —[d] |
| 1j | H | p-Br | no | 0.76 ± 0.17 | —[d] | —[d] | 2j[e] | p-F | p-Br | no | 1.6 ± 0.5 | —[d] | —[d] |

TABLE 2-continued

Inhibition of Eis-catalyzed KAN acetylation ($IC_{50}$ values) by the pyrrolo[1,5-a]pyrazine derivatives as well as effect of these molecules on KAN MIC values for Mtb H37Rv and KAN-resistant Mtb K204.

| Cpd # | $R_1$ | $R_2$ | Aromatic | $IC_{50}$ (μM)[a] | H37Rv $MIC_{KAN}$ (μg/mL)[b] | K204 $MIC_{KAN}$ (μg/mL)[c] | Cpd # | $R_1$ | $R_2$ | Aromatic | $IC_{50}$ (μM)[a] | H37Rv $MIC_{KAN}$ (μg/mL)[b] | K204 $MIC_{KAN}$ (μg/mL)[c] |
|---|---|---|---|---|---|---|---|---|---|---|---|---|---|
| 1k | H | p-Me | no | 0.64 ± 0.18 | —[d] | —[d] | 2k | p-F | p-Me | no | 0.47 ± 0.08 | —[d] | —[d] |
| 1a* | H | H | yes | 0.064 ± 0.008 | ≤1.25 | 5, 5 | 2a* | p-F | H | yes | 0.35 ± 0.07 | ≤1.25 | 5, 5 |
| 1b* | H | o-F | yes | 0.21 ± 0.05 | ≤1.25 | 5, 5 | 2b* | p-F | o-F | yes | 0.29 ± 0.07 | ≤1.25 | 5, 2.5 |
| 1c* | H | m-F | yes | 0.06 ± 0.01 | ≤1.25 | 5, 5 | 2c* | p-F | m-F | yes | 0.22 ± 0.05 | ≤1.25 | 2.5, 2.5 |
| 1d* | H | m-Cl | yes | 0.025 ± 0.006 | ≤1.25 | 5, 5 | 2d* | p-F | m-Cl | yes | 0.06 ± 0.02 | ≤1.25 | 5, 5 |
| 1e* | H | m-Br | yes | 0.34 ± 0.10 | ≤1.25 | 2.5, 2.5 | 2e* | p-F | m-Br | yes | 0.06 ± 0.02 | ≤1.25 | 5, 5 |
| 1f* | H | m-OH | yes | 1.8 ± 0.5 | ≤1.25 | 10, 5 | 2f*[e] | p-F | m-OH | yes | 8.4 ± 2.8 | ≤1.25 | 10, 10 |
| 1g* | H | m-OMe | yes | 0.21 ± 0.07 | ≤1.25 | 5, 5 | 2g* | p-F | m-OMe | yes | 0.53 ± 0.11 | ≤1.25 | 5, 2.5 |
| 1h* | H | p-F | yes | 0.029 ± 0.007 | ≤1.25 | 5, 5 | 2h* | p-F | p-F | yes | 0.13 ± 0.04 | ≤1.25 | 1.25, 1.25 |
| 1i* | H | p-Cl | yes | 0.56 ± 0.20 | ≤1.25 | 1.25, 1.25 | 2i* | p-F | p-Cl | yes | 0.18 ± 0.06 | ≤1.25 | 2.5, 5 |
| 1j* | H | p-Br | yes | 0.27 ± 0.01 | ≤1.25 | 2.5, 2.5 | 2j* | p-F | p-Br | yes | 0.50 ± 0.13 | ≤1.25 | 5, 2.5 |
| 1k* | H | p-Me | yes | 0.19 ± 0.02 | ≤1.25 | 2.5, 5 | 2k* | p-F | p-Me | yes | 0.08 ± 0.03 | ≤1.25 | 2.5, 5 |
| | | | | | | | 3a | m,p-di-F | H | no | 0.15 ± 0.05 | ≤1.25 | 10, 10 |
| | | | | | | | 3d | m,p-di-F | m-Cl | no | 0.043 ± 0.006 | ≤1.25 | >10, >10 |
| | | | | | | | 3h | m,p-di-F | p-F | no | 0.11 ± 0.03 | ≤1.25 | 10, 10 |
| | | | | | | | 3k | m,p-di-F | p-Me | no | 0.11 ± 0.03 | ≤1.25 | 10, 10 |
| Control without an Eis inhibitor: | | | | 1.25 | 10 | | | | | | | | |

[a]$IC_{50}$ values against purified Eis_Mtb enzyme.
[b]Anti-tubercular activity of KAN against Mtb H37Rv.
[c]Anti-tubercular activity of KAN against Mtb K204.
[d]The inhibitor interacted with alamarBlue® resulting in a color change, therefore, it was impossible to determine the MIC using this method.
[e]In MIC assays, the compounds were tested at concentrations that were 100-fold higher than $IC_{50}$. When the $IC_{50}$ value was >1 μM the compounds were tested at 100 μM. The compounds were not toxic to Mtb in the absence of KAN at these concentrations.

We first tested whether the freshly synthesized parent compound 1a* was indeed a potent Eis inhibitor. Expectedly, the freshly synthesized compound 1a* was found to display potent inhibition of Eis ($IC_{50}$=0.064±0.008 μM), which was ~6-fold better than the $IC_{50}$ value of the commercially available compound 1a* ($IC_{50}$=0.36±0.03 μM) from our previous HTS (Note: freshly synthesized powder are often more active than HTS library compounds, which may degrade upon storage).[18] The hit scaffold 1a* contains a pyrrolo[1,5-a]pyrazine core, a phenyl ring adjacent to the pyrrolo[1,5-a]pyrazine core (containing $R_1$), and an acetophenone moiety (containing $R_2$). A comparison of the chemical structure of compound 1a* with those of the previously published isothiazole S,S-dioxide-based Eis inhibitors co-crystallized with Eis (FIG. 8)[15] suggested that 1a* binds to Eis at the AG binding pocket[20] similarly to the isothiazole S,S-dioxides. Examination of the Eis crystal structure bound to the AG tobramycin (TOB) (PDB: 4JD6[20]) indicated that the positively-charged pyrrolo[1,5-a]pyrazine core is presumably essential for binding to the negatively-charged AG binding pocket and thus, should not be modified. Based on our previous survey of the hits of this HTS,[18] we also determined that the phenyl ring adjacent to the pyrrolo[1,5-a]pyrazine core (containing $R_1$) is likely important for Eis inhibition. In fact, replacing the phenyl ring of 1a* with an ethyl group resulted in a 25-fold reduction in the inhibitory activity ($IC_{50}$=9.25±1.50 μM).[18] Also from the crystal structure of Eis in complex with the isothiazole S,S-dioxide-based Eis inhibitors, we have rationalized that this phenyl ring is important due to its snug fit in a hydrophobic binding pocket in the AG binding cavity. On the other hand, the π-electron rich acetophenone moiety (containing $R_2$) and the fully aromatic pyrrolo[1,5-a]pyrazine core were predicted to be crucial for binding due to potential π-π interactions with aromatic residues within the Eis binding pocket. However, it remains unexplored whether and which substitutions at $R_1$ and $R_2$ positions would be beneficial. We hypothesized that: (i) tailor fitting the Eis binding pocket by introducing subtle modifications at $R_1$ and $R_2$ would lead to the discovery of novel optimized inhibitors from our hit scaffold 1a*, and (ii) disruption of the aromaticity of the pyrrolo[1,5-a]pyrazine core would be detrimental to the binding affinity of the molecule to the Eis binding pocket. In our biochemical analysis, we will first examine the aromatic compounds and then explore their non-aromatic counterparts. Both the aromatic and non-aromatic molecules are divided into two series. In series 1, $R_1$ was kept constant ($R_1$=H), and various substituted acetophenones were installed onto the pyrrolo[1,5-a]pyrazine core (changing $R_2$). Similarly, in series 2, $R_1$ was kept constant ($R_1$=p-F), and the same various substituted acetophenones were installed onto the pyrrolo[1,5-a]pyrazine core (changing $R_2$). For the non-aromatic compounds, four additional members were added to a third series (series 3) where $R_1$ was m,p-di-F.

We began our analysis of the aromatic compounds by investigating series 1. To probe the ortho position of the acetophenone moiety, compound 1b* ($R_1$=H, $R_2$=o-F) was generated and found to display a ~3-fold reduction in Eis inhibitory activity ($IC_{50}$=0.21±0.05 μM) when compared to the freshly synthesized parent 1a* (Note: from here on, when comparing to 1a*, we refer to the freshly synthesized 1a*), indicating that ortho substitution was not beneficial. We then explored substitutions at the meta position with compounds 1c*-1g*. The meta-substituted compound 1c* ($R_1$=H, $R_2$=m-F) was found to have comparable Eis inhibitory activity ($IC_{50}$=0.06±0.01 μM) to the parent compound 1a*. We systematically increased the size of the halogen substituents in compounds 1d* ($R_1$=H, $R_2$=m-Cl) and 1e* ($R_1$=H, $R_2$=m-Br).

Interestingly, compound 1d* displayed an $IC_{50}$ value of 0.025±0.006 μM, which was ~3-fold smaller than that of the parent compound 1a*. On the other hand, compound 1e* ($IC_{50}$=0.34±0.10 μM) was not as potent as compound 1d*, suggesting that the Br substituent was possibly too sterically hindered and thus, not well tolerated in the Eis binding pocket. Compound 1f* ($R_1$=H, $R_2$=m-OH) ($IC_{50}$=1.8±0.5 μM) was less potent than the parent compound, which suggested that having a highly polar substituent could be disfavored. Alternatively, replacing the hydroxyl group by a methoxy (compound 1g* ($R_1$=H, $R_2$=m-OMe)) yielded a molecule with improved Eis inhibition ($IC_{50}$=0.21±0.07 μM) when compared to 1f*. Overall, we found that the Cl was the best substituent at the meta position. We pondered whether this trend would translate to the para position, which prompted us to evaluate compounds 1h* ($R_1$=H, $R_2$=p-F), 1i* ($R_1$=H, $R_2$=p-Cl), and 1j* ($R_1$=H, $R_2$=p-Br). Intriguingly, the smaller F substituent was optimal at the para position with an $IC_{50}$ value of 0.029±0.007 μM contrary to what we observed at the meta position.

Intriguingly, inhibitor 1h* displayed an $IC_{50}$ of 0.029±0.007 μM, which, similarly to the $IC_{50}$ values for several other inhibitors was smaller than the half of the enzyme concentration used in our assay (0.25/2=0.125 μM). This effect has at least three potential explanations: (1) If inhibition of one monomer per Eis hexamer by one inhibitor molecule leads to the loss of activity of the entire hexamer, then the $IC_{50}$ can, in principle, be as low as 0.125/6=0.02 μM; (2) If only a fraction of Eis protein is active in acetylating KAN and binding inhibitors (e.g., due to protein aggregation), then the concentration of active Eis in the assay is an overestimate of the concentration of active enzyme; and (3) If inhibitor binding to Eis causes Eis aggregation and inactivates multiple hexamers, then $IC_{50}$ is also a fraction of the half of the enzyme concentration in the assay. Mechanism #3 is unlikely, because we do not observe global conformational changes in Eis upon inhibitor binding in crystal structures. Distinguishing among these mechanisms of these highly potent analogues is a goal of ongoing work in the group.

Subsequently, we investigated the effect of $R_1$ substitutions on the phenyl ring adjacent to the pyrrolo[1,5-a]pyrazine core. As the p-F substitution was one of the best in terms of activity when we varied $R_2$ in series 1, we first decided to install the p-F substituent at the $R_1$ position and generated series 2 analogues. Analogue 2a* ($R_1$=p-F, $R_2$=H) displayed weaker Eis inhibition ($IC_{50}$=0.35±0.07 μM) than did 1a*. Similarly to 1b* ($R_1$=H, $R_2$=o-F), the ortho-substituted analogue 2b* ($R_1$=p-F, $R_2$=o-F) was also not optimal. When we increased the size of the $R_2$ substituents at the meta position, we observed that the larger halogens led to more potent Eis inhibition (Br=Cl>F) and yielded compounds with $IC_{50}$ values varying from 0.06 to 0.22 μM. Unlike compound 1e* ($R_1$=H, $R_2$=m-Br; $IC_{50}$=0.34±0.10 μM), the m-Br substituted analogue 2e* ($R_1$=p-F, $R_2$=m-Br; $IC_{50}$=0.06±0.02 μM) was much more potent, which pointed to the possibility that changing $R_1$ from H to p-F could lead to a slight variation in the binding orientation of the molecule, especially near the meta position of the acetophenone ring. Additionally, the m-hydroxy and m-methoxy substitutions, as in the cases of 2f* ($R_1$=p-F, $R_2$=m-OH) and 2g* ($R_1$=p-F, $R_2$=m-OMe) either completely abolished Eis inhibitory activity or resulted in moderate inhibition of the enzyme ($IC_{50}$=8.4±2.8 and 0.53±0.11 μM, respectively). This was consistent with the observations made with compounds 1f* ($R_1$=H, $R_2$=m-OH) and 1g* ($R_1$=H, $R_2$=m-OMe). For the para-substituted analogues (2h* ($R_1$=p-F, $R_2$=p-F), 2i* ($R_1$=p-F, $R_2$=p-Cl) and 2j* ($R_1$=p-F, $R_2$=p-Br)), similarly to what was observed with series 1, the larger halogen substituents were generally less favorable with activities varying in the range of 0.13-0.50 μM. We also evaluated the para-methylated analogue 2k* ($R_1$=p-F, $R_2$=Me) and found that 2k* displayed excellent activity with an $IC_{50}$ value of 0.08±0.03 μM, which was 2-fold better than that of 1k* ($IC_{50}$=0.19±0.02 μM).

Having established the general SAR trends for the aromatic analogues, we next aimed to determine whether their non-aromatic counterparts (1a-k and 2a-k) would exhibit decreased activity due to potential disruption of the π□π interactions with Eis aromatic amino acid residues. Indeed, we found that most of the non-aromatic analogues generally displayed less potent Eis inhibition than their aromatic counterparts did. In four out of 22 cases, the aromatic and non-aromatic compounds display nearly equipotent inhibition of Eis. In the case of compounds 1c and 1c* ($R_1$=H, $R_2$=m-F), the $IC_{50}$ values were virtually the same ($IC_{50}$=0.05±0.01 and 0.06±0.01 μM, respectively). Additionally, compounds 2e and 2e* ($R_1$=p-F, $R_2$=m-Br) were also practically equipotent in terms of Eis inhibitory activities ($IC_{50}$=0.07±0.02 and 0.06±0.02 μM, respectively). Compounds 1g and 1g* ($R_1$=H, $R_2$=m-OMe) ($IC_{50}$=0.15±0.04 and 0.21±0.07 μM, respectively) were also similar. For the pair 1i and 1i* ($R_1$=H, $R_2$=p-Cl) ($IC_{50}$=0.31±0.09 and 0.56±0.20 μM, respectively), the non-aromatic counterpart 1i was marginally better. Regardless of whether the analogue in series 2 was aromatic or non-aromatic, it was conclusive that at the meta position of the acetophenone moiety, bigger halogen substituents such as Cl and Br were generally better suited, and at the para position of the acetophenone, the smaller F substituent was the best.

Once our pyrrolo[1,5-a]pyrazine derivatives were optimized for inhibition of the purified Eis enzyme in vitro, we set to confirm whether these compounds could display Eis inhibitory activity in the Mtb culture, by measuring the effect of the compounds on KAN MIC ($MIC_{KAN}$). Compounds were tested in combination with KAN against the KAN-sensitive H37Rv Mtb strain as a control and against the KAN-resistant Mtb K204, which is H37Rv Mtb bearing a clinically occurring point mutation in the eis promoter leading to overexpression of Eis.[4] Mtb H37Rv has an $MIC_{KAN}$ of 1.25 μg/mL, whereas KAN-resistant Mtb K204 has an $MIC_{KAN}$ of ≥10 μg/mL. Active compounds were expected to resensitize Mtb K204 to KAN. The compounds were generally tested at concentrations that were 100-fold higher than their respective $IC_{50}$ values in the enzymatic assays, to correct for the variation in the potency of Eis inhibition. Weakly potent compounds ($IC_{50}$>1 μM) were tested at 100 μM in the MIC assays. Mtb is notorious for its highly lipophilic and complex cell wall, which provides intrinsic resistance to many antibacterial compounds and presents an immense challenge for anti-tubercular drug discovery. Indeed, as shown in our previous Eis inhibitors studies,[15] some of the most potent in vitro compounds were not active in Mtb cultures. We also cannot exclude low solubility or aggregation of the compounds in the culture media as a reason for poor activity. Herein, we determined the MIC values for KAN ($MIC_{KAN}$) against Mtb K204 in the absence or presence of our Eis inhibitors and compared them to the $MIC_{KAN}$ of the drug-sensitive Mtb H37Rv strain. As anticipated, most compounds caused a reduction in the $MIC_{KAN}$ for Mtb K204, overcoming KAN resistance. Poor Eis inhibitors such as compounds 1f* and 2f* with relatively high $IC_{50}$ values were unable to resensitize Mtb K204 to the action of KAN. These observations, together with the lack of toxicity of these inhibitors when used without KAN for either Mtb strains, validate Eis inhibition as the principal mechanism of $MIC_{KAN}$ reduction by these compounds. Mtb H37Rv, for which $MIC_{KAN}$ is virtually unaffected by the inhibitors, serves as an important negative control in this regard. Some of the good Eis inhibitors such as compounds 1c-1e, 1g, 1h, 2d, 2e, 2h, 3a, 3d, 3h, and 3k did not resensitize Mtb K204 to the action of KAN despite their nanomolar $IC_{50}$ values ($MIC_{KAN} \geq 10$ µg/mL), indicating that these molecules may not go through the cell envelope. Compounds 1a*-1e*, 1g*, 1h*, 1i, 1j*, 1k*, 2a*-2e*, 2g*, 2i*-2k* partially restored activity of KAN ($MIC_{KAN}$=2.5-5 µg/mL). Generally, the analogues in series 1 and 2 displayed better potency compared to the analogues in series 3 in Mtb culture. While the charged nature of these compounds may contribute adversely to the permeability of the compounds through the greasy mycobacterial cell envelope, their better solubility in aqueous solution when compared to other uncharged Eis inhibitors may offset this potential issue. Therefore, these compounds serve as valuable alternatives to uncharged Eis inhibitors of other scaffolds in further preclinical development of Eis inhibitors as KAN adjuvants in TB therapy. Indeed, two compounds, 1i* and 2h*, are highly promising for future development, as they completely restore the potency of KAN, fully overcoming Eis upregulation.

Figure 7:
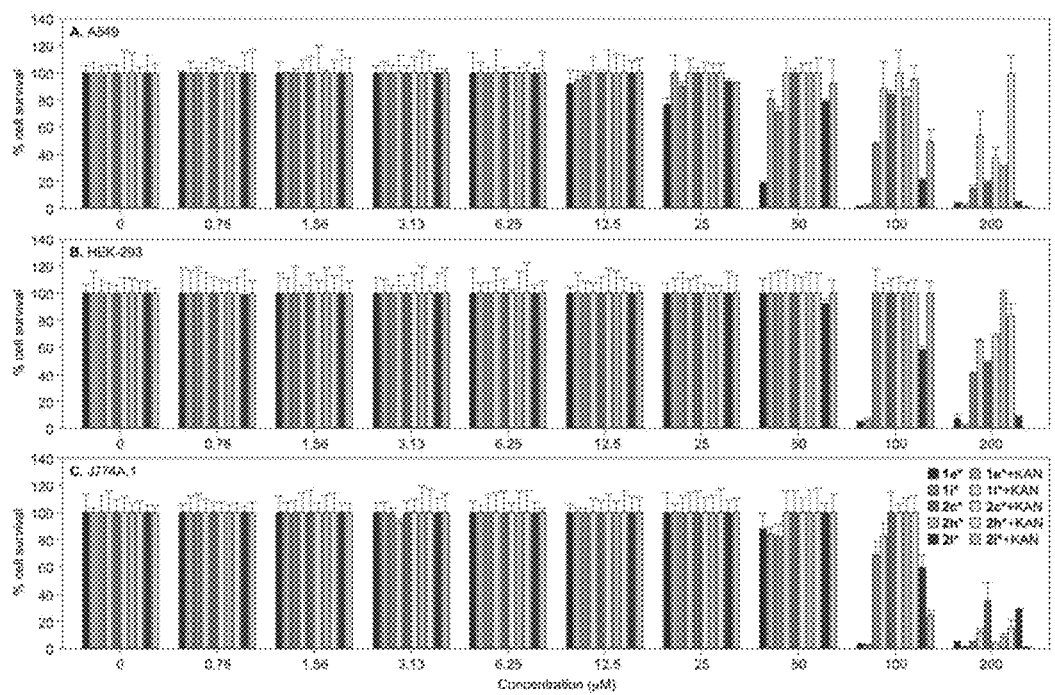
FIG. 7 includes results of mammalian cytotoxicity studies of selected compounds (1e*, 1i*, 2c*, 2h*, and 2i*) alone (represented as dark color columns) or in the presence of 50 µg/mL (equivalent to 86 µM) KAN (represented as light color columns immediately to the right of the dark color column of the corresponding compound in the absence of KAN) against A. A549, B. HEK-293, and C. J774A.1 cells.
Figure 9:
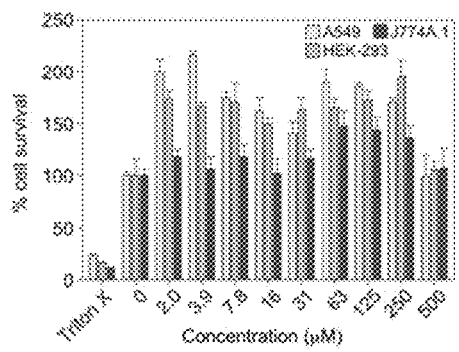
FIG. 9 includes results of a study showing cytotoxicity of KAN against A549, HEK-293, and J774A.1 mammalian cell lines.

Cytotoxicity to three different mammalian cell lines was tested for five representative potent Eis inhibitors (FIG. 7) in the absence and presence of KAN at the concentration of 50 µg/mL (equivalent to 86 µM) greatly exceeding the $MIC_{KAN}$ of Mtb. The negative control corresponded to no inhibitor treatment and was standardized as 100% cell survival. The positive control was a treatment with Triton 100-X®, where we observed most of the cells killed. The cytotoxicity data are presented in FIG. 7. We observed that at sub-$IC_{50}$ concentrations, our Eis inhibitors induced cell proliferation, thereby displaying >100% cell survival. With the exception of compound 1e*, which at 50 µM exhibited significant cytotoxicity against one of the three cell lines, none of the compounds were cytotoxic against any of the three cell lines up to 50 µM. Three compounds (1i*, 2c*, 2h*) had no significant cytotoxicity up to 100 µM, without or with KAN. The lack of cytotoxicity indicates the absence of toxic off-target effects in the mammalian cells, strengthening the promise of these compounds as candidates for animal and clinical studies. Eis inhibitors appear to be less toxic when co-administering with KAN. Upon assessing the cytotoxicity of KAN alone (FIG. 9) and Eis inhibitors alone (FIG. 7), one can observe that exposure to KAN or to Eis inhibitors alone at sub-$IC_{50}$ concentrations promotes cell growth. This phenomenon of increased growth in the presence of small quantities of xenobiotics has been previously observed.[21-25] Due to this effect, co-treatment with KAN and Eis inhibitors may result in a faster cell growth than that for KAN alone.

Figure 8:
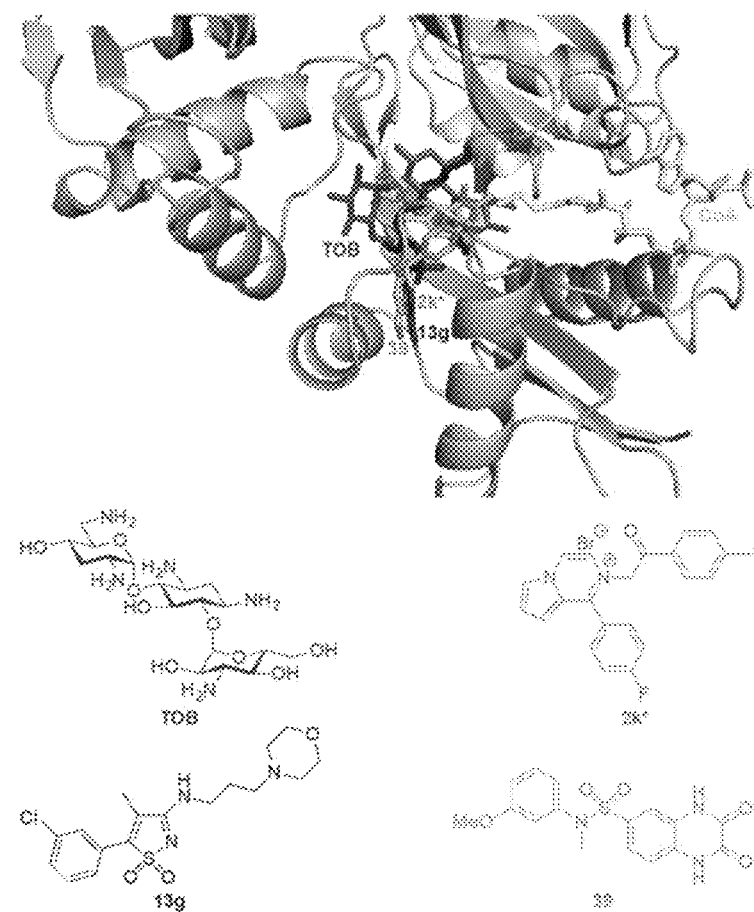
FIG. 8 illustrates the inhibitor/aminoglycoside binding site showing the superimposition of Eis inhibitors and TOB from several crystal structures. The chemical structures of inhibitors 2k*, 13g, and 39, as well as of TOB are shown below the crystal structure.
Figure 10:
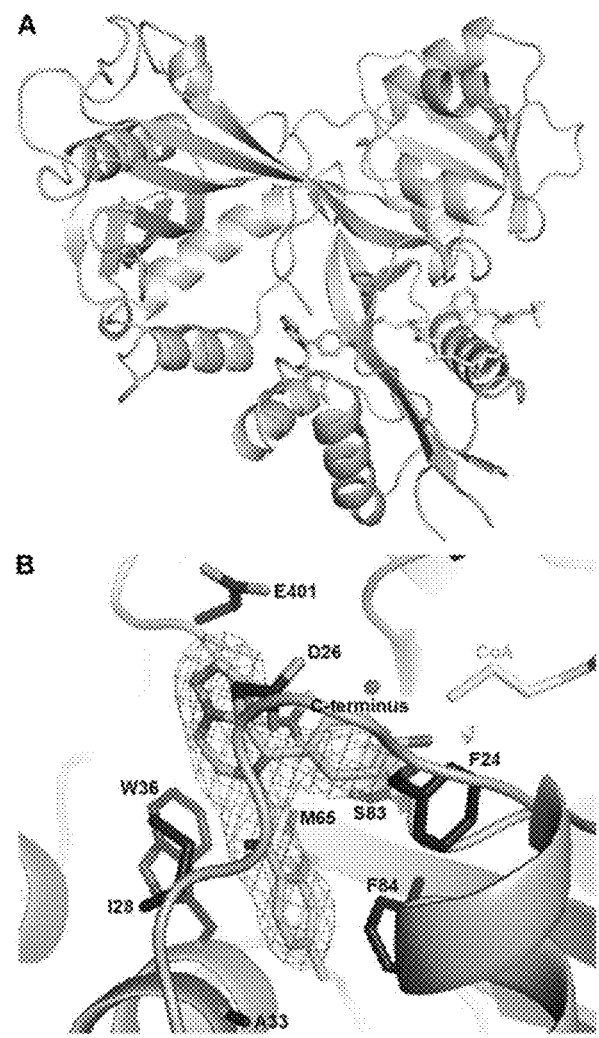
FIG. 10 includes a crystal structure of EisC204A-CoA-inhibitor 2k* complex (PDB ID 5TVJ) (panel A), and a zoom-in view of the binding pocket of compound 2k* (panel B).
Figure 11:
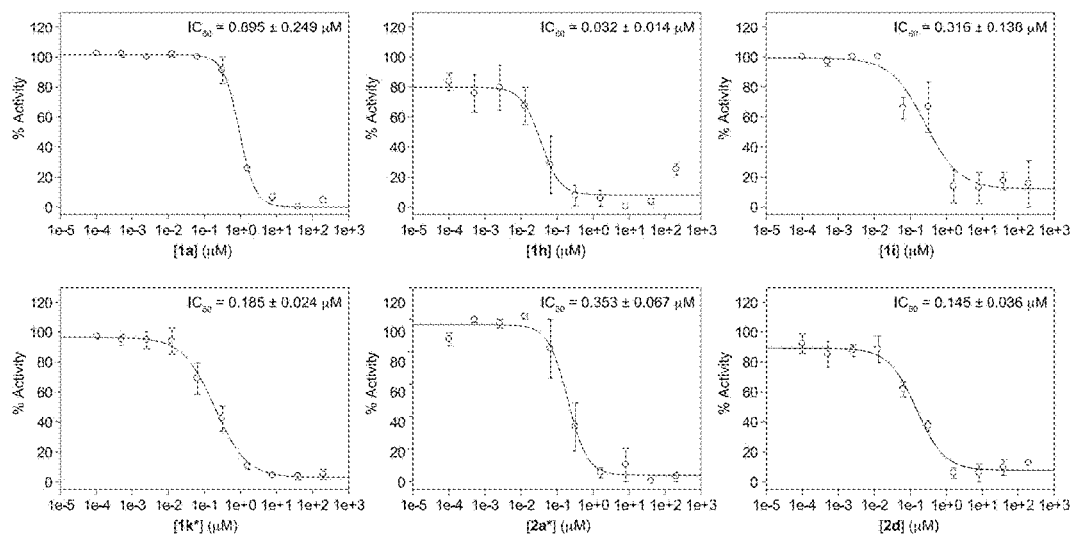
FIG. 11 includes representative $IC_{50}$ curves for exemplary compounds according to the scaffolds set forth in FIG. 6.

To rationalize our SAR study and understand the binding mode of our inhibitors to Eis, we determined a crystal structure of Eis in complex with CoA and inhibitor 2k* (one of our best inhibitors; $IC_{50}$=0.08±0.03 µM) at the resolution of 2.4 Å (FIG. 10). The crystal structure demonstrates that inhibitor 2k* is indeed bound in the AG binding site (established by our reported Eis-CoA-TOB crystal structure;[20] FIG. 8) and is stabilized in the bound state by numerous hydrophobic interactions with Eis. The pyrazine ring is stacked between the side chain of Glu401 of Eis and its C-terminal carboxyl group, with mutually orthogonal π-π interactions of the pyrazine ring with the indole ring of Trp36. This observation supports our initial hypothesis that the aromaticity of the pyrrolo[1,5-a]pyrazine core is crucial for activity and explains why aromatized compounds resulted in better activities during SAR analysis. Attached to the pyrrolo[1,5-a]pyrazine core, the acetophenone ring displayed parallel π-π interaction with Phe84 and showed that our prediction about the importance of the aromatic acetophenone was correct. Additionally, the $R_2$-substituted acetophenone fits in a hydrophobic environment of Leu63, Trp36, and Arg37. Hence, adding a polar hydroxyl group at $R_2$, such as in compounds 1f, 1f*, 2f, and 2f*, destabilizes binding within the hydrophobic environment and results in weaker Eis inhibitory activity. Furthermore, the para position of the acetophenone ring is sterically restrained on all sides, being sandwiched between Phe84 and Trp36 and abutting Trp13 and Met65, explaining why the larger groups in para position, such as in compounds 1i/i*, 1j/j*, 2i/i*, and 2j/j* resulted in decreased Eis inhibitory activities. This $R_2$ binding pocket of Eis accommodates structurally similar substitutions of our previously published inhibitors with different core scaffolds (FIG. 8). Otherwise, these previously reported inhibitors are bound in distinct orientations in the large AG binding cavity. As shown in FIG. 10 and in our SAR analysis, near the two meta positions of the acetophenone ring, there are spacious pockets allowing incorporation of larger substituents at the meta position without compromising activity. Lastly, the phenyl ring containing $R_1$ is located in a spacious binding pocket lined by the terminus of the phosphopantetheinyl tail of the CoA molecule, Asp26, the C-terminal carboxyl group, Ser83, and Phe24, explaining why a phenyl group is preferred over an ethyl group at the $R_1$ position. In summary, the crystal structure of the EisC204A-CoA-inhibitor 2k* complex allowed us to explain our biological data and provides a basis for future additional structure-based development of Eis inhibitors.

In conclusion, via a SAR study, we tailor-fitted Eis inhibitors possessing the pyrrolo[1,5-a]pyrazine core to its Eis binding pocket and identified multiple novel nanomolar potency inhibitors. We validated our hypothesis that the aromaticity of the pyrrolo[1,5-a]pyrazine core was important for activity and that aromatic analogues were overall better inhibitors than their non-aromatic counterparts. For the aromatic analogues, our study indicated that the SAR strongly correlates with the size of the halogen substituent(s). At the meta position of the acetophenone, bigger halogens such as Cl and Br were generally well tolerated. On the other hand, at the para position, substitutions of a smaller F atom and a methyl group produced analogues with substantially improved activities. The SAR analysis also revealed that the substitution of a polar functional group such as the hydroxyl group greatly perturbed the hydrophobic environment leading to decreased activity. These SAR observations were explained by the crystal structure analysis, which will greatly facilitate future medicinal chemistry studies. Most significantly, by in vitro Mtb culture assays, we confirmed that our Eis inhibitors were capable of penetrating the Mtb cell wall and cancelling the KAN-resistance of Mtb K204, which overexpresses Eis. As exemplified by a clinically used combination of a β-lactamase inhibitor, clavulanic acid, and penicillin, these Eis inhibitors may become similarly significant as adjuvant molecules in a combination therapy with KAN to prevent emergence of and combat KAN resistance in MDR- and XDR-TB.

Example 3

This Example relates to the discovery and rational structure-based optimization via medicinal chemistry of promising sulfonamide Eis inhibitors that not only efficiently inhibit the purified enzyme, but also restore KAN susceptibility of KAN-resistant Mtb. We also present a crystal structure of Eis in complex with CoA and one potent sulfonamide inhibitor, which reveals its mode of action, explains our SAR study and paves the way for further rational structure-based development of Eis inhibitors.

Identification and Chemical Synthesis of Eis Inhibitors.

Figure 12:
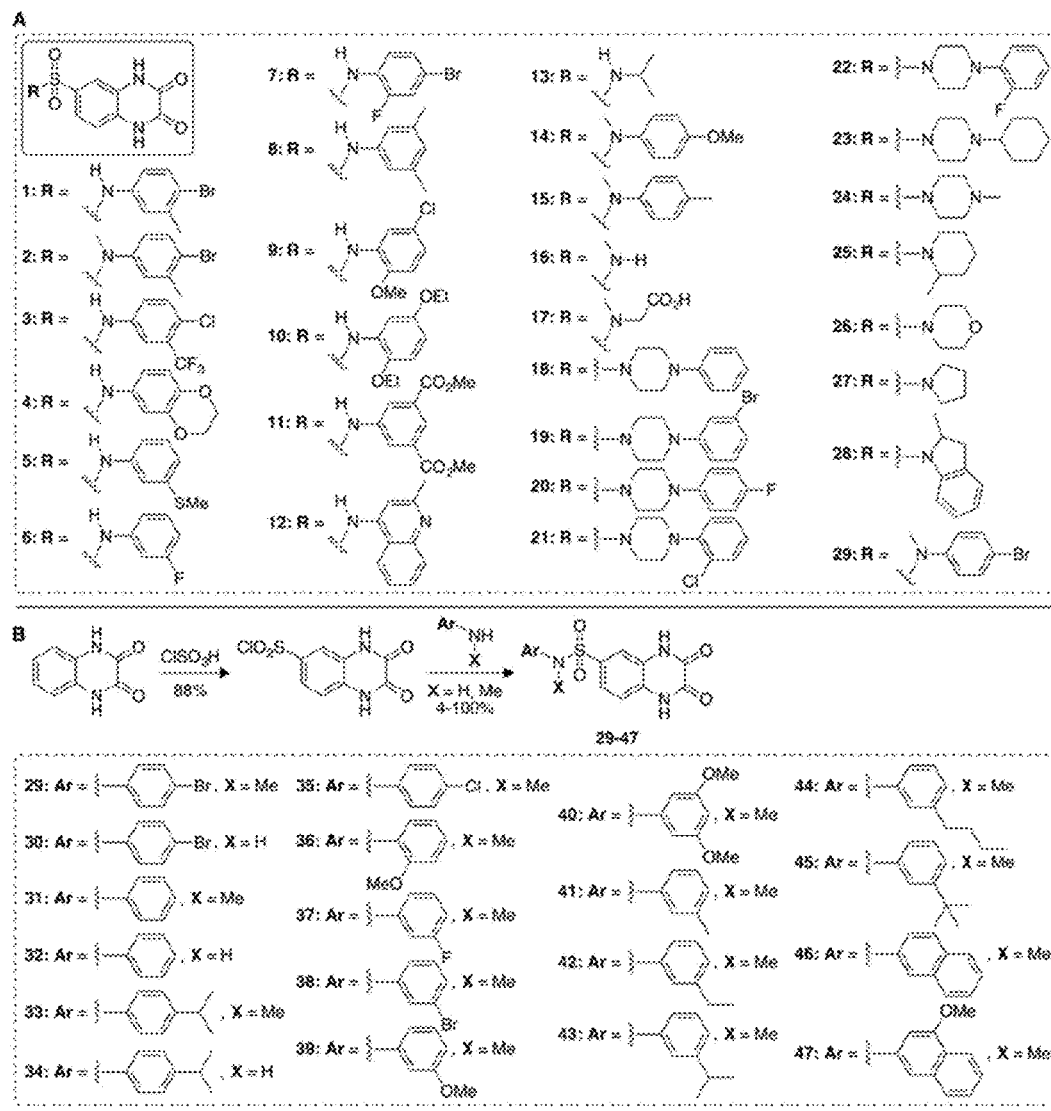
FIG. 12 includes preparation schemes and structures of exemplary Eis inhibitor scaffolds according to the presently-disclosed subject matter and discussed in Example 3.

To identify potential Eis inhibitor candidates, we used an established UV absorbance-based HTS assay[12] to screen over 123,000 structurally diverse small molecules for their inhibition of KAN acetylation by the Eis_Mtb acetyltransferase in vitro. The screening of this molecular library against Eis_Mtb led to the identification of a sulfonamide scaffold (FIG. 12B). The HTS library contained 29 compounds (1-29) with this core structure, and four (1, 3, 4, and 29) were identified as hits (i.e., compounds displaying ≥3-fold higher inhibition than the magnitude of the standard deviation). Compounds 2 and 5-28 were found not to inhibit Eis in the HTS. As compounds 16-28 were unable to inhibit Eis, we concluded that at least an aromatic ring attached to the nitrogen atom is important for inhibitory activity. While compounds 1, 3, and 4 displayed modest Eis inhibition, compound 29 potently inhibited Eis activity ($IC_{50}$=0.5±0.1 μM). Based on this encouraging result, we synthesized compound 29 along with 18 additional sulfonamide analogues (30-47) containing a variety of substituents on the aniline ring to define a preliminary body of structure-activity relationship (SAR) of Eis inhibition. The compounds were synthesized by a reaction of 2,3-dihydroxyquinoxaline with chlorosulfonic acid to generate sulfonyl chloride, which then reacted with different aniline derivatives to yield compounds 29-47 (FIG. 12A).

Biochemical and Biological Testing of Sulfonamides 29-47.

Figure 15:
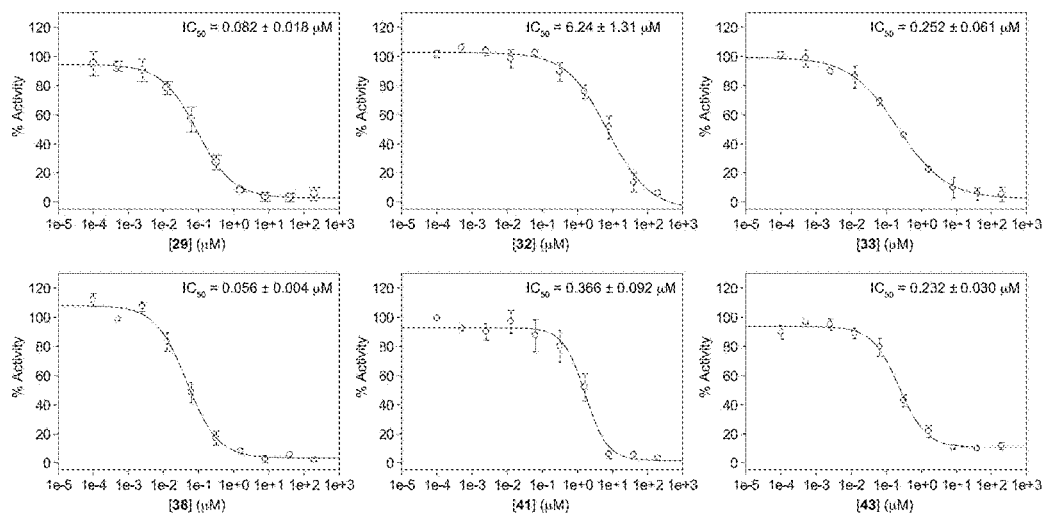
FIG. 15 includes representative $IC_{50}$ curves for exemplary compounds according to the scaffolds set forth in FIG. 12.

To investigate the potential of these compounds as Eis inhibitors for use in combination with KAN, we evaluated their biochemical ($IC_{50}$ values against purified Eis enzyme) and biological (effect on the MIC values of KAN in KAN-sensitive Mtb H37Rv and in KAN-resistant Mtb K204[2]) properties in parallel studies (Table 3 and FIG. 15).

TABLE 3

$IC_{50}$ values against purified Eis and KAN MIC values against Mtb H37Rv and Mtb K204 in the absence and presence of the compounds at the specified concentrations.

| Compound # | Ar | X | $IC_{50}$ (μM)[a] | Concentration tested (μM)[b] | H37Rv $MIC_{KAN}$ (μg/mL)[c] | K204 $MIC_{KAN}$ (μg/mL)[d] |
|---|---|---|---|---|---|---|
| — | — | — | — | — | 1.25 | 10 |
| 29 | p-Br—Ph | Me | 0.08 ± 0.02 | 8 | ≤1.25 | 2.5 |
| 30 | p-Br—Ph | H | 6.2 ± 1.3 | 100 | ≤1.25 | 5 |
| 31 | Ph | Me | 5.8 ± 1.8 | 100 | ≤1.25 | 5 |
| 32 | Ph | H | >200 | 100 | ≤1.25 | 10 |
| 33 | p-iPr—Ph | Me | 0.25 ± 0.06 | 25 | ≤1.25 | 2.5-5 |
| 34 | p-iPr—Ph | H | 10.6 ± 2.5 | 100 | ≤1.25 | 5 |
| 35 | p-Cl—Ph | Me | 0.100 ± 0.045 | 10 | ≤1.25 | 2.5 |
| 36 | o-OMe—Ph | Me | >200 | 100 | ≤1.25 | 10 |
| 37 | m-F—Ph | Me | 3.0 ± 0.7 | 30 | ≤1.25 | 5 |
| 38 | m-Br—Ph | Me | 0.056 ± 0.004 | 5.6 | ≤1.25 | 2.5 |
| 39 | m-OMe—Ph | Me | 5.8 ± 1.2 | 100 | ≤1.25 | ≤1.25 |
| 40 | 3,5-di-OMe—Ph | Me | 7.4 ± 3.3 | 100 | ≤1.25 | 5-10 |
| 41 | m-Me—Ph | Me | 0.37 ± 0.09 | 37 | ≤1.25 | 2.5-5 |
| 42 | m-Et—Ph | Me | 0.027 ± 0.012 | 2.7 | ≤1.25 | 5-10 |
| 43 | m-iPr—Ph | Me | 0.23 ± 0.03 | 23 | ≤1.25 | 2.5-5 |
| 44 | m-nBu—Ph | Me | 0.7 ± 0.3 | 70 | ≤1.25 | 5-10 |
| 45 | m-tBu—Ph | Me | 27 ± 8 | 100 | ≤1.25 | 5-10 |
| 46 | 2-naphthyl | Me | 0.00024 ± 0.00010 | 100 | ≤1.25 | ≤1.25 |
| 47 | 4-OMe-2-naphthyl | Me | 0.30 ± 0.08 | 100 | ≤1.25 | 10 |

[a]$IC_{50}$ values and standard errors for inhibition of purified Eis enzyme,

[b]Compounds were tested at concentrations that were either 100-fold higher than their $IC_{50}$ or at 100 μM if the $IC_{50}$ value could not be achieved while keeping the DMSO concentration at ≤1% in test wells. At these concentrations, the compounds did not inhibit the growth of Mtb H37Rv or that of Mtb K204 when tested in the absence of KAN.

[c]Anti-TB activity of KAN against Mtb H37Rv,

[d]Anti-TB activity of KAN against Mtb K204.

Importantly, Mtb K204 is genetically identical to H37Rv, except for one clinically derived point mutation in the eis promoter that causes upregulation of Eis acetyltransferase resulting in the resistance of Mtb K204 to KAN.[2] In this regard, H37Rv serves as an important Eis knockdown control for validating the mechanism of action of the Eis inhibitors in the bacterial cell. To correct out the effect of different potencies ($IC_{50}$) of the Eis inhibitors as determined by the enzyme assay, in the MIC assays we used the inhibitors at concentrations that were 100-fold higher than their $IC_{50}$ values, where achievable. The freshly synthesized compound 29 displayed robust inhibition of Eis in vitro ($IC_{50}$=0.08±0.02 μM). When combined with KAN, sulfonamide 29, resulted in a four-fold reduced KAN MIC value (2.5 μg/mL) compared to KAN alone (10 μg/mL) for K204 Mtb. This was a reduction almost to the MIC level of KAN in the KAN-susceptible Mtb H37Rv (1.25 μg/mL) parent strain. To gain insight into the importance of the substitution pattern on the aniline portion of the sulfonamide scaffold, we generated secondary (NHAr) and tertiary (N(Me)Ar) sulfonamides (29-47). Eis inhibition assays with the synthesized sulfonamides were carried out in combination with KAN. The non-methylated counterpart of lead compound 29, compound 30, displayed lower Eis inhibitory activity ($IC_{50}$=6.24±1.31 μM) and had a smaller effect than 29 did on the KAN resistance in Mtb K204 (MIC$_{KAN}$=5 μg/mL). Two other non-methylated derivatives, 32 and 34, also resulted in lower Eis inhibitory activity (IC$_{50}$>200 and 10.6±2.5 μM, respectively) and did not overcome KAN resistance in Mtb K204 (MIC$_{KAN}$=10 and 5 μg/mL, respectively). These data, in conjunction with the fact that compounds 1 and 3-13 from the HTS did not display significant Eis inhibition, suggest that the N-methyl group is essential for efficient Eis inhibition and antitubercular activity.

Having established the importance of the N-methyl moiety, we explored the effect of substitutions on the benzene ring of the aniline moiety. Removing all substituents on the benzene ring (compound 31) resulted in a 70-fold decrease in Eis inhibitory activity (IC$_{50}$=5.8±1.8 μM) when compared to that of lead 29 and did not overcome KAN resistance in Mtb K204, suggesting the importance of a substituted aniline for Eis inhibition and antitubercular activity. In general, para substitution (compounds 29 with a p-Br, 33 with a p-iPr, and 35 with a p-Cl) was found to be favorable and yielded compounds with IC$_{50}$ values varying from 0.08-0.25 μM, which overcame KAN resistance (MIC$_{KAN}$=2.5 μg/mL) in KAN-resistant Mtb. Interestingly, p-methoxy substitution resulted in a compound (14) that was found to be inactive during our HTS. To delineate if ortho or meta substitution would be more favorable than para substitution, we generated compounds 36 (with an o-OMe) and 39 (with a m-OMe). The o-methoxy substituted 36 was found to be completely inactive (IC$_{50}$>200 μM and MIC$_{KAN}$=10 μg/mL against Mtb K204), whereas the m-methoxy substituted 39 was found to be a potent Eis inhibitor (IC$_{50}$=5.8±1.2 μM) and was one of our two compounds to fully overcome KAN resistance in Mtb K204 (MIC$_{KAN}$≤1.25 μg/mL). It is important to note that incorporating an additional m-methoxy group, as in compound 40, was detrimental for the overall activity of the molecule, which suggested that mono-substitution is more promising than di-substitution. We also synthesized the m-bromo derivative 38, which demonstrated a slightly improved Eis inhibitory activity (IC$_{50}$=0.056±0.004 μM) than did the corresponding para derivative 29, while also being able to overcome KAN resistance in Mtb K204 (MIC=2.5 μg/mL). We also found that the m-iso-propyl derivative 43 and its para counterpart 35 displayed similar Eis inhibitory activity (IC$_{50}$=0.23±0.03 and 0.25±0.06 μM, respectively) and resulted in identical KAN MIC values (2.5-5 μg/mL) against KAN-resistant Mtb. While the p-methyl derivative 15 was inactive in our HTS, its meta counterpart 41 displayed good Eis inhibition (IC$_{50}$=0.37±0.09 μM) and some ability to overcome KAN resistance in Mtb K204 (MIC 2.5-5 μg/mL). These data suggest that mono-meta substitution is either equal or more advantageous then para, which is more beneficial than ortho. Based on these results, we generated additional m-alkylated sulfonamides (42, 44, and 45) and observed that longer or bulkier alkyl groups, although good for Eis inhibition, did not produce compounds capable of overcoming KAN resistance in Mtb K204. Finally, with the hope of increasing any possible π-π interaction between the inhibitor and the AG-binding site of the Mtb Eis, we generated compound 46, which showed a dramatic increase in Eis inhibitory activity (IC$_{50}$=0.00024±0.00010 μM) and was found to completely overcome KAN resistance in Mtb K204 (MIC$_{KAN}$≤1.25 μg/mL). Compound 46 is currently our most potent and promising Eis inhibitor that can be used in conjunction with KAN. Since compound 39 with the methoxy group in the meta position is one of our best compounds to fully overcome KAN resistance in Mtb K204, we also synthesized compound 47 with a m-methoxy substitution on the naph-thyl group, but this led both to a loss of Eis inhibition and to a loss of the effect on MIC$_{KAN}$ (see next section).

The Eis inhibitors lacked anti-Mtb activity in the absence of KAN in either tested strain (Table 3). Furthermore, most compounds sensitized the KAN-resistant Mtb K204 to KAN, as expected based on their 100-fold IC$_{50}$ concentrations used in these assays, with two compounds (39 and 46) completely cancelling the effect of the Eis upregulation in Mtb K204. The two compounds that were least potent in the enzymatic assay (32 and 36) and used in the MIC assay at concentrations below 100×IC$_{50}$ were also inert in that assay. This general correlation of the potency in the enzymatic assays and their effect on MIC$_{KAN}$ canceling that of Eis upregulation, taken together, validate inhibition of Eis by these compounds as the mechanism of their sensitization of Mtb K204 to KAN. Synergistic growth inhibition in combination with KAN by some effect other than Eis inhibition can be ruled out because the inhibitors do not change MIC$_{KAN}$ in H37Rv. The cell envelope of Mtb is a notoriously tough barrier, and some compounds penetrate the cell envelope more readily than others in a manner that is not correlated with the IC$_{50}$ values. This would explain the variability of MIC$_{KAN}$ values in Table 3.

To examine the selectivity of our two best inhibitors (39 and 46) towards Eis, we next tested these two compounds against three other AAC enzymes: AAC(2')-Ic from Mtb,[19, 20] AAC(3)-IV from E. coli,[21, 22] and AAC(6')-Ie/APH(2")-Ia from Staphylococcus aureus.[23, 24] Sulfonamides 39 and 46 did not inhibit KAN acetylation by the AACs tested at concentrations as high as 200 μM with the exception of 39, which inhibited 15% of the AAC(2')-Ic activity when tested at 200 μM. These data demonstrate the high selectivity of our inhibitors towards Eis.

Crystal Structure of EisC204A-CoA-Inhibitor 39 Complex.

Figure 13:
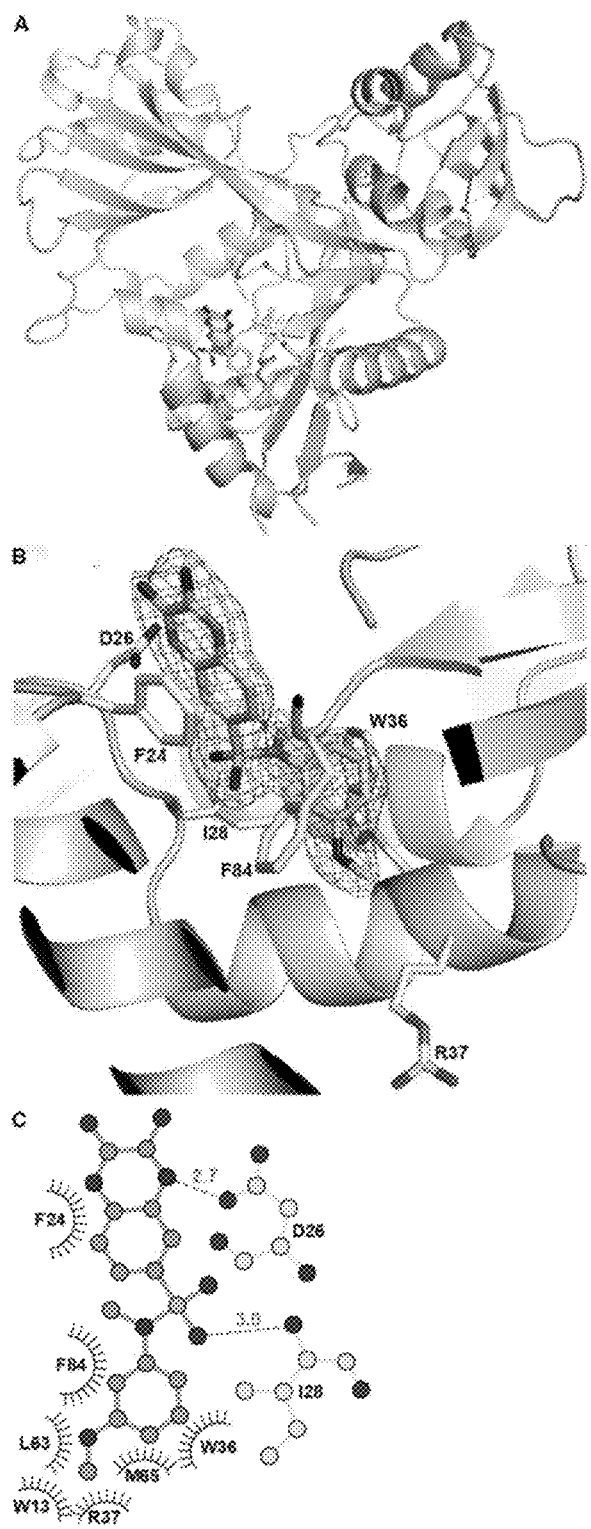
FIG. 13 includes a cartoon view of the crystal structure of Eis in complex with compound 39 and CoA, including the overall view of a monomer of Eis-CoA-inhibitor 39 complex (panel A), the zoomed-in view of the AG-binding site with the bound inhibitor (panel B), and a schematic of Eis-inhibitor 39 contacts (panel C).

In order to characterize the mechanism of our Eis inhibitors, explain the SAR, and aid in future drug development, we determined the crystal structure of Eis in complex with CoA and inhibitor 39 at the resolution of 2.1 Å (FIG. 13 and Table 4).

TABLE 4

X-ray diffraction data collection and refinement statistics for the EisC204A-CoA-inhibitor 39 ternary complex structure (PDB ID 5IV0).

| Data collection | |
|---|---|
| Space group | R32 |
| Number of monomers per asymmetric unit | 1 |
| Unit cell dimensions | |
| a, b, c (Å) | 175.2, 175.2, 122.3 |
| α, β, γ (°) | 90, 90, 120 |
| Resolution (Å) | 50.0-2.1 (2.14-2.10)$^a$ |
| I/σ | 16 (2.1) |
| Completeness (%) | 95.8 (97.7) |
| Redundancy | 3.9 (3.8) |
| R$_{merge}$ | 0.08 (0.50) |
| Number of unique reflections | 37,907 |
| Structure refinement statistics | |
| Resolution (Å) | 40.0-2.1 |
| R (%) | 19.4 |
| R$_{free}$ (%) | 21.9 |
| Bond length deviation (rmsd) from ideal (Å) | 0.006 |
| Bond angle deviation (rmsd) from ideal (°) | 1.35 |
| Ramachandran plot statistics$^b$ | |
| % of residues in most allowed regions | 93.8 |
| % of residues in additional allowed regions | 6.2 |

TABLE 4-continued

X-ray diffraction data collection and refinement statistics
for the EisC204A-CoA-inhibitor 39 ternary complex structure
(PDB ID 5IV0).

| | |
|---|---|
| % of residues in generously allowed regions | 0.0 |
| % of residues in disallowed regions | 0.0 (0 residues) |

[a]Numbers in parentheses indicate the values in the highest-resolution shell.
[b]Indicates Procheck statistics.[29]

Although sulfonamide 46 was our best compound in biochemical and biological studies, it did not co-crystallize with Eis. The crystal structure demonstrates that inhibitor 39 is bound in the part of the AG-binding pocket that is formed by the N-terminal domain of Eis. The inhibitor binding site partially overlaps with the binding site of TOB, as observed in our previously reported structure of Eis-CoA-TOB (FIG. 14),[7] indicating that the Eis inhibitors are competitive with AGs. The inhibitor is apparently stabilized in the bound state by numerous hydrophobic interactions (FIG. 13, panels B and C). The shape of the inhibitor binding pocket and the interacting hydrophobic residues are not conserved in other AAC enzymes, explaining the observed selectivity of the inhibitors. Specifically, the aniline moiety is stacked between the rings of Phe84 and Trp36, with the methoxy group located in the hydrophobic pocket lined by the nonpolar stem of the Arg37 side chain, Phe84, Trp13, and Leu63. This explains why removing the aniline ring resulted in a loss of activity for compounds 13, 16, 17, and 23-27. The quinoxaline moiety stacks against Phe24, a residue that also interacts with TOB (FIG. 14, panel B), as previously observed in a crystal structure of an Eis-TOB complex (FIG. 14).[7] The NH group of the quinoxaline ring on the side of the sulfonamide forms a hydrogen bond with the carboxyl group of Asp26 (N—O distance of 2.7 Å) and the oxygen of the sulfonamide forms a hydrogen bond with the main chain nitrogen of Ile28 (O—N distance of 3.0 Å). Our SAR studies showed that compounds with an N-methyl group of the sulfonamide moiety displayed higher Eis inhibitory activity than those with an NH group, which can be rationalized by the optimal van der Waals interaction of the methyl with Trp36 (the distance between the methyl C atom and the closest C of the Trp36 side chain is 3.6 Å). Eliminating the methyl group would abolish this interaction, putting a polar NH in a hydrophobic environment, likely destabilizing binding (6 vs 37, 30 vs 29, 32 vs 31, and 34 vs 33). Replacing the aniline ring with an N-aryl piperazine (compounds 18-22) resulted in a loss of Eis inhibitory activity when compared to the aniline ring. As described above, this part of the molecule is snugly fit in a hydrophobic pocket, which is too small to accommodate these larger groups. The ortho position of the aniline ring is flanked by the C-terminal residue Phe402 and it abuts Phe84, explaining why an ortho substitution, as in compound 36, resulted in a loss of Eis inhibitory activity. A bulky group such as n-butyl (44) or t-butyl (45) in meta position of the aniline ring would clash with Arg37 that is structurally fixed by π-π stacking with the inhibitor, explaining the poor inhibitory activity of these two compounds. A meta,meta-disubstitution (40) resulted in a dramatic decrease in activity as the second substituent would clash with the side chain of Met65. Electron-donating groups such as methoxy (39) or a naphthalene ring (46) increase the π-π interaction of the aniline ring with Phe84 and Trp36, explaining their stronger interactions in the AG-binding pocket of Eis. However combining the two substituents in compound 47 led to a loss of activity, as both substitutions cannot be sterically accommodated.

Figure 14:
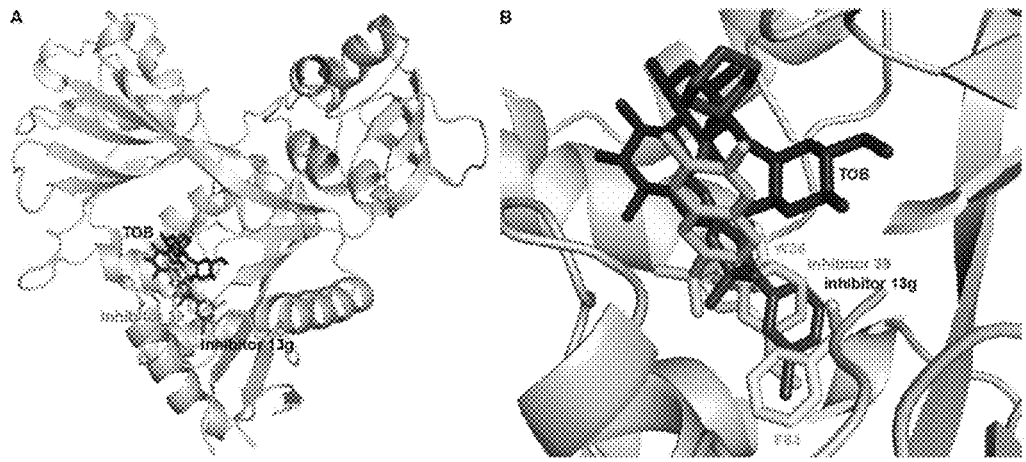
FIG. 14 includes the crystal structure of Eis in complex with inhibitor 39 from this study and a previously published Eis inhibitor (labeled 13g in ref[2]) with an isothiazole S,S-dioxide heterocyclic core obtained by superimposition of the crystal structures (panel A), and the zoomed-in view of the binding site with the bound inhibitors and TOB (panel B).

The overall conformation of Eis in complex with the inhibitor is similar to the previously reported crystal structure.[5] A notable conformational difference is that a part of a loop (residues 28-30) and a helix (residues 31-37) are shifted towards the inhibitor relative to their conformation in the structure without the inhibitor by 1-1.5 Å, apparently in an induced-fit fashion, to maximize steric contacts. The indole ring of Trp36 in this helix is rotated by ~40°, maximizing the stacking with the aniline ring and other interactions, as explained above. These small, but significant conformational changes likely precluded us from obtaining a correct model of a bound inhibitor by prior extensive computational docking simulations. Inhibitor 39 occupies a similar space in the AG binding pocket as a previously reported inhibitor with the isothiazole S,S-dioxide heterocyclic core (labeled 13g in reference[17]) (FIG. 14 FIG. 14), but the orientations of the two inhibitors and their interactions with the protein side chains are largely different. The only common feature is the nearly coplanar binding of the methoxy- and the chlorophenyl rings of the two respective inhibitors, with both rings sandwiched by Phe84 and Trp36 of Eis (FIG. 14 FIG. 14, panel B). In summary, the crystal structure of the EisC204A-CoA-inhibitor 39 complex allowed us to fully explain our biochemical and biological data and provides a solid foundation for further rational structure-based development of Eis inhibitors.

In conclusion, the biochemical, biological, and structural studies described in this manuscript provide a proof-of-principle of the activity of Eis inhibitors as promising KAN adjuvants. The SAR combined with the co-crystal structure will guide future development of these compounds for their clinical use against MDR- and XDR-TB.

Example 4

This example relates to development of inhibitors of Eis, which can be co-administered with KAN in order to prevent inactivation by Eis in Mtb. Here, we report the identification as well as the biochemical and biological characterization of several potent inhibitors of Eis that were able to restore the antibacterial activity of KAN in a KAN-resistant strain, Mtb K204. To clarify in atomic details the mode of action of these compounds and their structure-activity-relationships, we also determined crystal structures of EisC204A in complex with CoA and two of these inhibitors.

Figure 16:
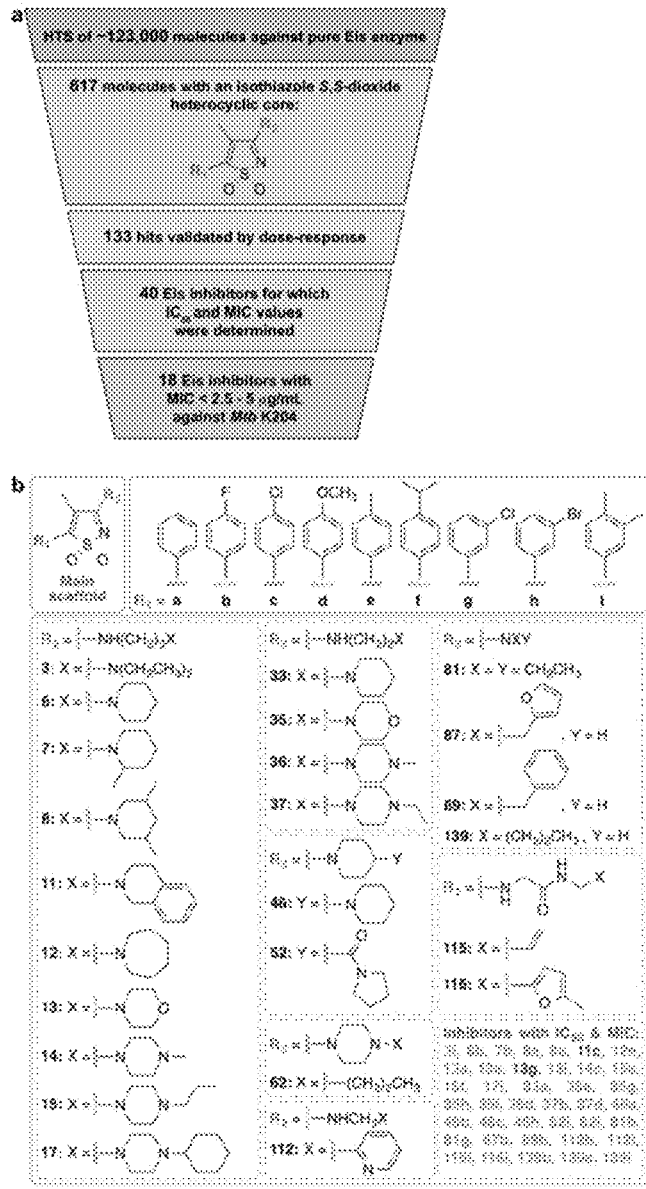
FIG. 16 includes a schematic representation of the winnowing of small organic molecules to 18 showing inhibition of both Eis enzymatic activity and growth of Mtb K204 in the presence of KAN (panel a), and structures of exemplary Eis inhibitor scaffolds according to the presently-disclosed subject matter and discussed in Example 4.
Figure 17:
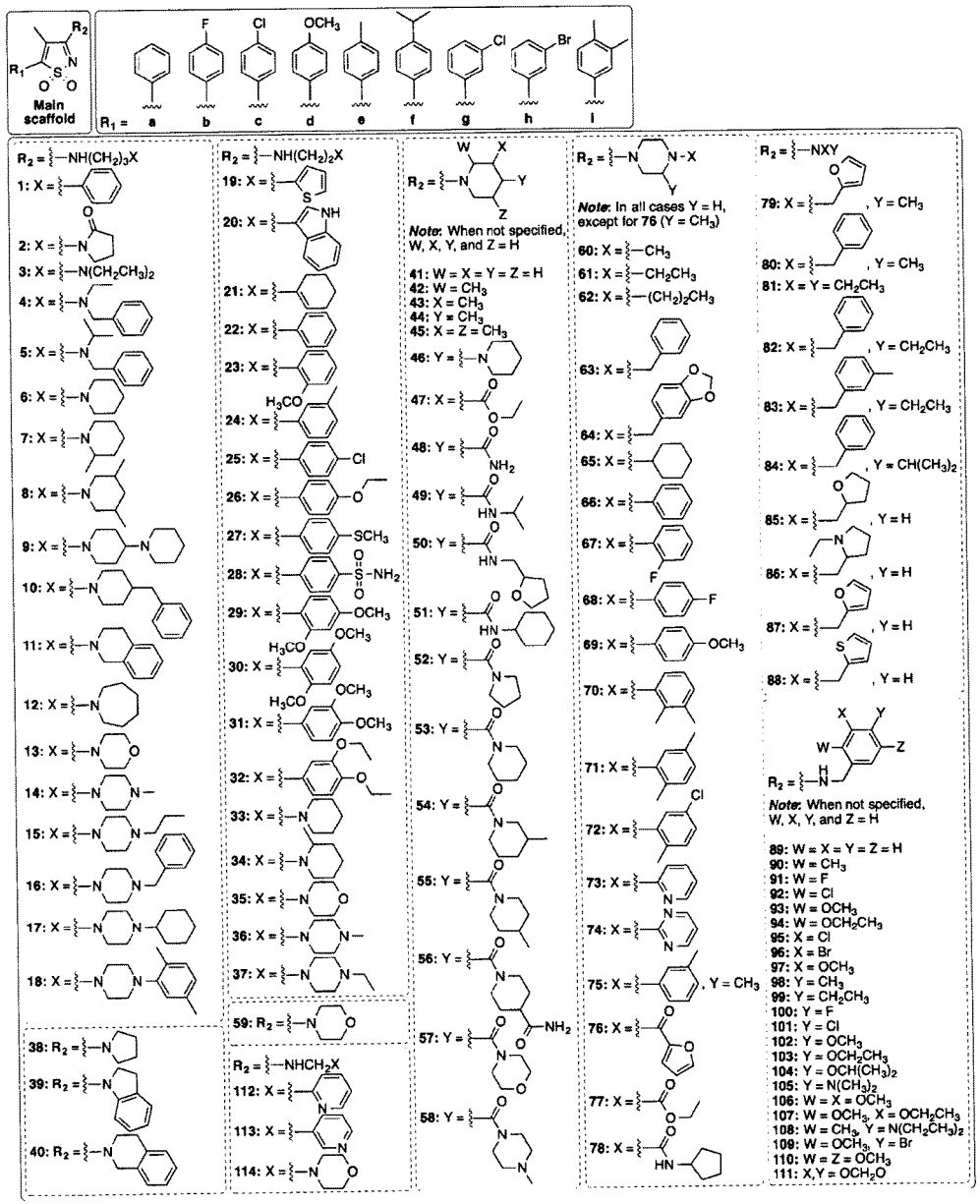
FIG. 17 includes further structures of Eis inhibitor according to the presently-disclosed subject matter and discussed in Example 4.

High-throughput screening leads to the identification of a promising Eis inhibitor scaffold. In order to identify Mtb Eis inhibitors, we carried out a HTS of molecular libraries comprising 123,000 structurally diverse small molecules using a previously reported Eis acetylation assay in the miniaturized format (FIG. 1a).[25] The initial HTS assay was performed using the aminoglycoside neomycin B (NEO) as a substrate, which was selected over KAN to maximize the signal to noise ratio under the HTS conditions. However, KAN was used in all post-HTS assays, since it is the clinically relevant aminoglycoside. The HTS yielded 617 hits containing an isothiazole S,S-dioxide heterocyclic core that were re-tested (FIG. 17). Of these 617 molecules, 133 showed reproducible inhibition of Eis enzymatic activity in the same single-point HTS assay. Thirty-six of these 133 compounds were chosen for further testing in dose-response assays, based on the potency of their inhibition of Eis in the HTS assay and the structural diversity of their chemical substituents ($R_1$ and $R_2$ groups). In a previous study of Eis inhibitors evaluating fewer molecules,[25] we demonstrated that active compounds contained (i) a group that may become positively charged, usually an amine, or (ii) an aromatic group. The presence of either of these groups was therefore also a criterion for selection of compounds for dose-response testing. Additionally, we included four analogues that were not a part of the original library, but which contained the same structural core (FIG. 16b). This process yielded a group of forty molecules, for which we determined $IC_{50}$ values against purified Eis. We also measured the effect of these compounds on KAN MIC for KAN-susceptible (H37Rv) and KAN-resistant (K204) Mtb strains (Table 5), as described in the two following sections.

TABLE 5

Eis inhibition $IC_{50}$ values of tested compounds and the effect of the compounds on kanamycin A MIC values against H37Rv and K204 Mtb strains.

| Cpd | $IC_{50}$ (μM)[a] | Concentration tested (μM)[b] | H37Rv $MIC_{KAN}$ (μg/mL)[c] | K204 $MIC_{KAN}$ (μg/mL)[d] |
|---|---|---|---|---|
| — | — | — | 1.25 | 10 |
| 3i | 0.120 ± 0.035 | 12 | 0.625 | 1.25 |
| 6b | 0.152 ± 0.045 | 15.2 | 0.625 | 2.5 |
| 7b | 0.102 ± 0.034 | 10.2 | 0.625 | 2.5 |
| 8a | 2.85 ± 0.26 | 184.5 | 0.625-1.25 | 5 |
| 8e | 0.200 ± 0.036 | 20 | 0.625 | 2.5-5 |
| 11c | 0.238 ± 0.089 | 23.8 | 0.625 | 1.25 |
| 12e | 0.183 ± 0.043 | 18.3 | 0.625 | 2.5 |
| 13a | 2.82 ± 0.21 | 282.3 | 0.625 | 2.5 |
| 13e | 0.331 ± 0.071 | 33.1 | 0.625 | 2.5 |
| 13g | 0.234 ± 0.060 | 23.4 | 0.625 | 2.5-5 |
| 13i | 0.054 ± 0.002 | 5.42 | 0.625 | 5 |
| 14c | 0.112 ± 0.008 | 11.2 | 0.625 | 5 |
| 15e | 0.535 ± 0.045 | 53.5 | 0.625-1.25 | 5 |
| 15f | 0.148 ± 0.016 | 14.8 | 0.625-1.25 | 10 |
| 17i | 0.232 ± 0.038 | 23.2 | 0.625-1.25 | 5 |
| 33a | 0.123 ± 0.023 | 13.2 | 0.625 | 5 |
| 35e | >200 | 20 | 0.625 | 5 |
| 35g | 2.49 ± 0.49 | 100 | 0.625 | 2.5 |
| 35h | 3.23 ± 0.99 | 100 | 0.625 | 2.5 |
| 35i | 0.985 ± 0.190 | 98.5 | 0.625 | 2.5 |
| 36d | 0.152 ± 0.031 | 15.3 | 0.625 | 2.5-5 |
| 37b | 0.657 ± 0.105 | 65.7 | 0.625 | 2.5-5 |
| 37d | >200 | 20 | 0.625-1.25 | 5-10 |
| 46a | 0.432 ± 0.057 | 43.2 | 0.625-1.25 | 10 |
| 46b | 0.092 ± 0.021 | 9.21 | 0.625-1.25 | 5 |
| 46c | 0.109 ± 0.022 | 10.9 | 0.625 | 2.5 |
| 46h | 0.135 ± 0.031 | 13.5 | 0.625 | 5 |
| 52i | 0.580 ± 0.096 | 58 | 0.625 | 2.5 |
| 62i | 0.386 ± 0.080 | 38.6 | 0.625 | 5 |
| 81b | 1.25 ± 0.22 | 124.8 | 0.625 | 2.5-5 |
| 81g | 1.42 ± 0.42 | 142.3 | 0.625 | 2.5 |
| 87b | >200 | 20 | 1.25 | 10 |
| 89b | >200 | 20 | 1.25 | 10 |
| 112b | >200 | 20 | 0.625 | 10 |
| 112i | 0.621 ± 0.229 | 62.1 | 0.625 | 5 |
| 115i | >200 | 20 | 0.625 | 10 |
| 116i | >200 | 20 | 1.25 | 10 |
| 139b | >200 | 20 | 0.625 | 10 |
| 139e | >200 | 20 | 1.25 | 10 |
| 139i | >200 | 20 | 1.25 | 10 |

[a] The $IC_{50}$ values in the Eis acetyltransferase assay.
[b] At these concentrations, these compounds did not inhibit the growth of H37Rv or that of K204 Mtb, when tested in the absence of KAN.
[c] KAN MIC values for H37Rv Mtb in the absence (first line) and in the presence of each compound at the specified concentrations.
[d] Same as [c], but for K204 Mtb.

Structure-Activity Relationship Studies.

Various $R_1$ and $R_2$ side-chains in the identified isothiazole S,S-dioxide heterocyclic scaffold (FIG. 16b, FIG. 17), were explored to improve anti-Eis potency in vitro. Based on the 617 initial HTS hit molecules, we first drew several unambiguous conclusions about the desirable structure of the $R_2$ side-chain. Most of the compounds for which $R_2$ contained an aromatic ring, a branched alkyl group, a cyclohexyl moiety, or a benzyl functionality did not efficiently inhibit Mtb Eis. Among the forty compounds that were pursued beyond the dose-response assay, compounds containing $R_2$ groups 8, 13, 15, 35, 46, and 81 inhibited Eis in vitro when combined with multiple $R_1$ substituents, while other $R_2$ groups were shown to inhibit Eis in dose-response assays when in combination with only one of the possible $R_1$ substituents (6b, 7b, 11c, 12e, 14c, 17i, 33a, 36d, 37b, 52i, 62i, and 112i). Overall, two large families of $R_2$ substituents emerged as potential potent inhibitors of Eis: (i) compounds with $R_2$ containing two nitrogen atoms separated by three carbon atoms (structures 3, 6-8, 11-15, and 17), particularly compounds with large bulky groups or a cyclohexyl ring attached to the extended nitrogen atom were most often inhibitory; and (ii) compounds containing an $R_2$ group with two nitrogen atoms separated by two carbon atoms also efficiently inhibited Eis (structures 33, 35-37, and 112). In this series of molecules, only compounds with a nitrogen atom located in a cyclohexyl ring were inhibitory.

We next explored the effect of the $R_1$ substituents on Eis inhibition. Upon initial inspection of the 617 HTS hits, the identity of the $R_1$ substituent appeared to have little effect on their Eis inhibitory activity. However, when analyzing these side chains statistically, patterns emerged. The p-fluorophenyl group (b) had the highest percentage (34%) of compounds inhibiting Eis in the initial HTS; this was followed closely by the p-methylphenyl group (e, 33%) and the m,p-dimethylphenyl group (i, 30%), suggesting that these three groups as $R_1$ substitutions have a better chance of contributing positively to Eis inhibition. The next best $R_1$ substituent was the p-chlorophenyl group (c) with 27% of the compounds within this group displaying inhibition of Eis. The m-chlorophenyl group (g) and p-anisole group (d) were next with 19% and 18% of their compounds displaying Eis inhibition, respectively. Finally, with 13%, 12%, and 9% of compounds showing Eis inhibition were compounds containing the p-isopropylphenyl (f), the m-bromophenyl (h), and the phenyl (a) group as $R_1$, respectively.

Having established general trends for the $R_1$ and $R_2$ substituents, we next focused on the measured in vitro potency ($IC_{50}$) of the forty selected compounds (Table 5). Several trends consistent with those established above emerged from these quantitative data. With the exception of compound 112i, mono-substituted $R_2$ amine substituents comprised of a straight alkyl chain (139b, 139e, 139i), an aromatic ring (87b, 89b, 112b), or an amide functionality (115i, 116i) did not inhibit purified Eis. Compounds with $R_2$ substituents containing a diamine separated by two carbon atoms with the second amine present in a cyclohexyl ring all displayed good to moderate Eis inhibition. However, no conclusion could be formed as to what type of cyclohexyl ring was best, an unsubstituted (33a), a morpholino (35e, g, h, and i), or a piperazinyl (36d or 37b) ring, as most $IC_{50}$ values were similar for these compounds. Compound 13i with a diamine separated by three carbons at the $R_2$ position and the m,p-dimethylphenyl group at the $R_1$ position was found to be the most potent Eis inhibitor ($IC_{50}$=0.054±0.002 μM). Interestingly, compound 46b with a cyclohexyl ring directly attached to the core scaffold followed by a second piperazine ring in the para-position was found to be the second best Eis inhibitor ($IC_{50}$=0.092±0.021 μM). These results indicate that both a rotationally free alkyl chain (as in compound 13i) or cyclically restricted alkyl linkers could be useful in designing Mtb Eis inhibitors.

To establish whether the inhibitors identified were specific to Eis over AACs from other families, compounds 46b and 46c were tested against AAC(6')-Ie/APH(2")-Ia from Staphylococcus aureus,[26,27] AAC(3)-IV from E. coli,[28] and AAC(2')-Ic from Mtb.[29,30] Under optimal reaction conditions for each enzyme, no inhibition by either compound was observed with any of these AACs (Table 6). These data demonstrate that the compounds are exquisitely selective for Mtb Eis over other AACs.

TABLE 6

Inhibition of different non-Eis AACs by compounds 46b and 46c.

| Compound | AAC | Concentration[a] (μM) | % activity[b] |
|---|---|---|---|
| 46b | AAC(2')-Ic | 200 | 100 |
| 46b | AAC(3)-IV | 200 | 100 |
| 46b | AAC(6')-Ie[c] | 200 | 80 |
| 46c | AAC(2')-Ic | 200 | 100 |
| 46c | AAC(3)-IV | 200 | 100 |
| 46c | AAC(6')-Ie | 200 | 75 |

[a]Maximum inhibitor concentration tested.
[b]The activity of the enzyme at the maximum inhibitor concentration (200 μM) relative to that without inhibitor.
[c]The acetylation activity of AAC(6')-Ie/APH(2")-Ia enzyme.

Eis Inhibitors Abolish Eis-Mediated Resistance of Mtb to KAN.

Having identified inhibitors of purified Mtb Eis enzyme, we next determined their activity in cellulo. Mycobacteria are notorious for their waxy cell wall that is difficult to penetrate for small molecules. Therefore, we anticipated that not all of the compounds that exhibited inhibition of purified Eis would be effective in cell cultures. We measured the effect of the forty selected compounds (at a concentration of 100-fold higher than their $IC_{50}$ values) on KAN MIC values against Mtb K204, a KAN-resistant strain bearing a clinically observed eis promoter mutation known to upregulate Eis production (Table 5). In the KAN-susceptible H37Rv strain, the MIC value of KAN is 1.25 μg/mL, whereas in the KAN-resistant K204 strain, the MIC value of KAN is 10 μg/mL. As expected, compounds that did not inhibit purified Mtb Eis (35e, 37d, 87b, 89b, 112b, 115i, 116i, and 139b, e, and i) did not overcome resistance to KAN in Mtb K204. 28 of the remaining 30 Eis inhibitors resulted in at least a 2-fold reduction in KAN MIC against Mtb K204, with two of these compounds, 3i and 11c, lowering KAN MIC 8-fold, down to the level of the KAN-susceptible H37Rv strain. Notably, these compounds did not have any effect on growth of either mycobacterial strain in the absence of KAN. Therefore, these compounds act synergistically with KAN against KAN-resistant Mtb. The compounds that reduced the MIC value of the KAN-resistant Mtb strain 4-fold had $IC_{50}$ values that ranged from 0.102±0.034 to 3.23±0.99 μM. Generally, in vitro (Eis inhibition) and in cellulo (KAN-sensitization) activities were correlated among the compounds tested in both assays. This correlation, together with the lack of inhibition of cell growth in the absence of KAN, serve as a strong evidence for inhibition of KAN acetylation by Eis as the principal mechanism of action in the mycobacterial cell. Not unexpectedly, among very potent inhibitors of the enzymatic activity of Eis in vitro, a small fraction of the compounds had little or no effect at sensitizing the resistant Mtb strain K204 to KAN. The lack of activity in the cells was likely due to the inability of these compounds to go through the cell envelope or due to their aggregation in the cell culture media at the concentrations that were much higher than those used in the enzymatic assay.

Crystal Structures of Eis-Inhibitor Complexes Reveal the Inhibition Mechanism.

Figure 18:
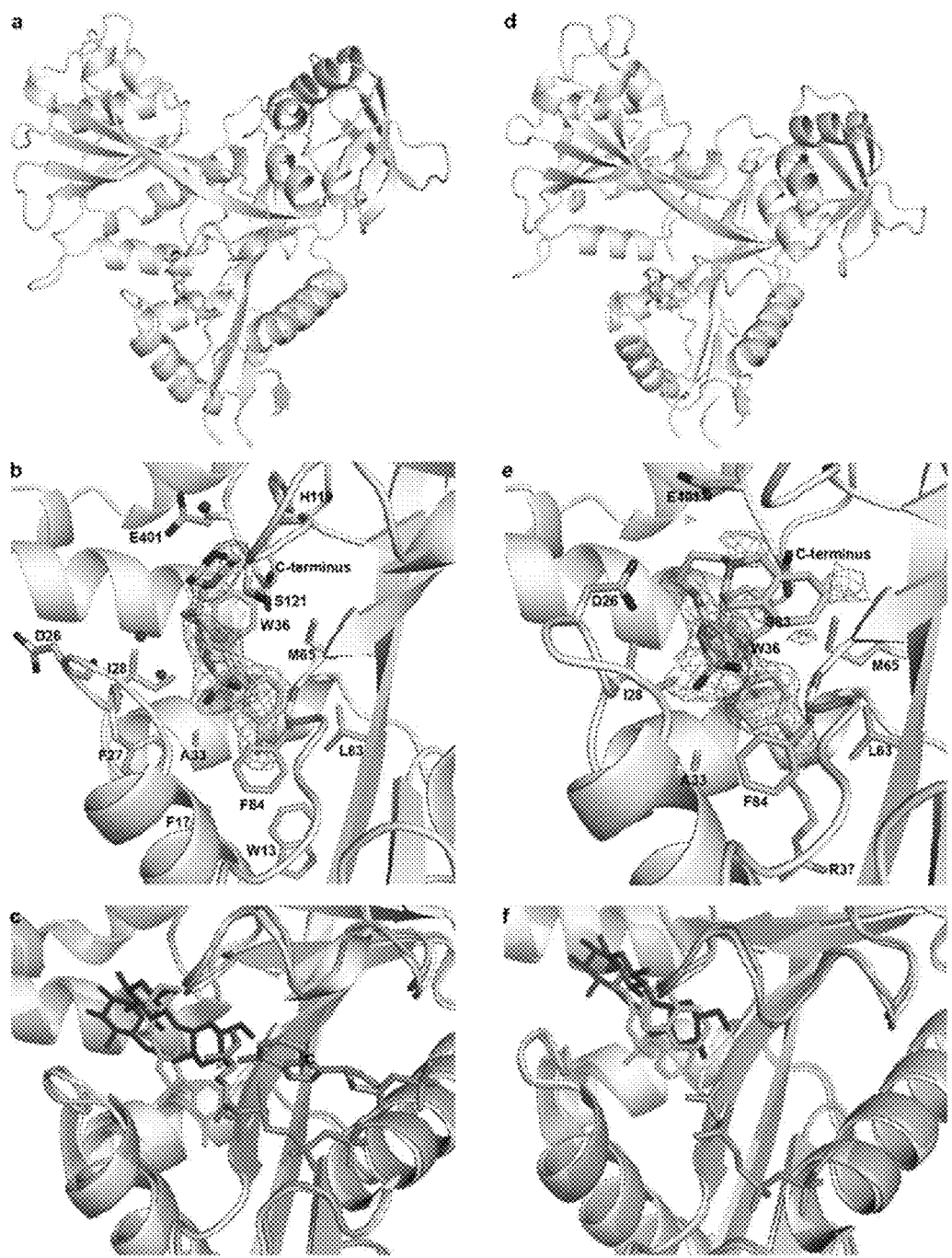
FIG. 18 includes crystal structures of EisC204A from Mtb in complex with 13g (a and b) and 11c (d and e), and the overall views of the Eis monomer with the inhibitors bound (a and c) and zoom-in views of the active site (b and e) show that the inhibitors occupy a site overlapping with the aminoglycoside substrate-binding site; superposition of these respective inhibitor structures with the previously reported crystal structure of EisC204A in complex with CoA and tobramycin is shown in panels c and f.
Figure 19:
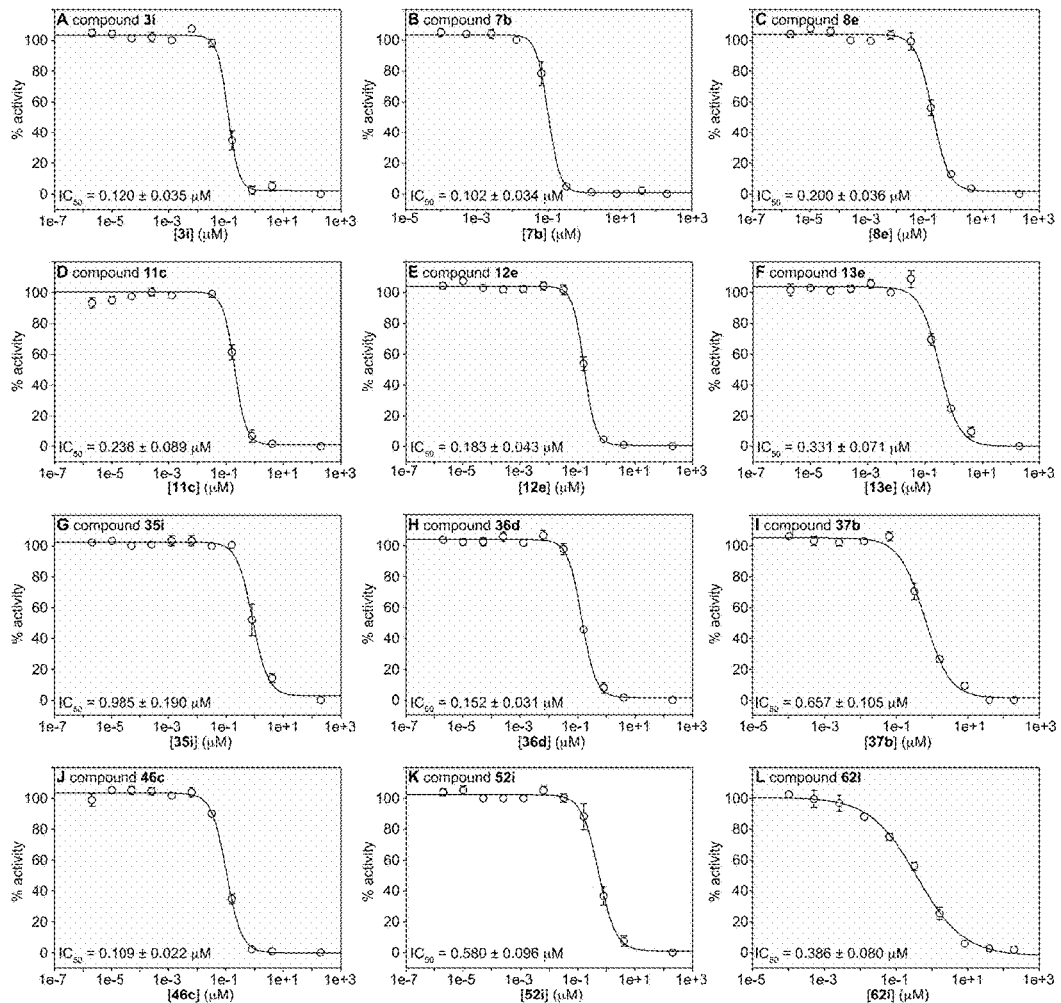
FIG. 19 includes representative $IC_{50}$ curves for exemplary compounds according to the scaffolds set forth in FIGS. 16 and 17.
Figure 20:
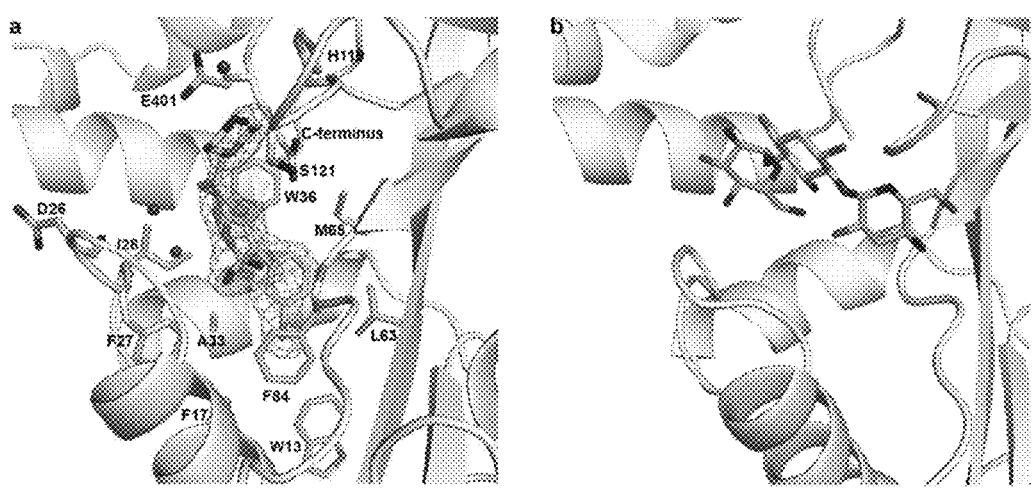
FIG. 20 includes a structural comparison of inhibitor 13g (panel a) and TOB bound in the active site of EisC204A (panel b).

To elucidate the mechanism of Eis inhibition by the isothiazole S,S-dioxide heterocyclic core-containing compounds, rationalize the observed SAR, and guide future rational inhibitor design, we determined 2.2 Å-resolution crystal structures of Eis in complex with CoA and inhibitors 13g and 11c (FIG. 18a,c), which displayed both potent inhibition of Eis acetylation in vitro and the KAN resistance abolishing effect in the Mtb cultures. Both inhibitors and their chemical features were clearly distinguishable and modeled into strong $F_o$-$F_c$ electron density (FIG. 18b,e). The only exception was the 1,2,3,4-tetrahydroisoquinoline group of 11c, for which only partial electron density was observed (FIG. 18e), likely due to a somewhat dynamic behavior of this highly hydrophobic group in a partially polar environment, as allowed by the flexible diamine linkage. No other significant difference electron density that could be attributed to a bound inhibitor was observed elsewhere. Both inhibitors exhibited high steric complementarity with the Eis surface. The binding site for both inhibitors overlapped with the aminoglycoside substrate-binding site, as was recently established by the structure of Mtb Eis in complex with CoA and tobramycin (FIG. 18c,f; FIG. 20 FIG. 20 FIG. 20).[10] In addition, the $R_2$ groups of both inhibitors reached the C-terminal carboxyl group of Eis, which was proposed to serve as the general base in the acetyl transfer reaction. Therefore, these crystal structures indicate that the inhibitors block access of aminoglycosides to the active site of the enzyme. Explaining the critical role of the isothiazole S,S-dioxide heterocyclic core, this group is bound in the same location and orientation in both Eis-inhibitor structures (FIG. 18). Remarkably, despite the nearly identical positions of this group, there are differences in how this group interacts with the protein for the two inhibitors. These differences are due to significant conformational changes in the region spanning residues 26-31 of Eis (FIG. 18b,e), which uniquely adapts to bind the two structurally different $R_2$ groups. For inhibitor 13g (FIG. 18a,b,c), one of the sulfonyl oxygens forms a direct hydrogen bond with the main chain amide nitrogen of Phe84 and the ring nitrogen forms a water-mediated hydrogen bond with the main chain amide nitrogen of Ile28. In this case, the Eis conformation resembles that observed in a previously reported crystal structure with the aminoglycoside-binding pocket unoccupied[4]. Inhibitor 11c does not make any water-mediated contacts due to a small positional shift of the inhibitor and a conformational change of Eis. Instead, the two sulfonyl oxygens are at a distance of ~4 Å, consistent with the stabilizing van der Waals and electrostatic interactions. The isothiazole ring is sterically sandwiched between the side chains of Ile28 and Ser83 in one direction and between the side chains of Phe24 and Trp36 in the orthogonal direction. The $R_1$ groups of the two compounds are almost coplanar and fit neatly into a nearly fully nonpolar environment of side chains Leu63, Trp13, and Ala33, the aliphatic stem of Arg37, Met65, and Phe84, explaining the nonpolar phenyl ring with small substitutions as effective $R_1$ groups (FIG. 16). Such environment, devoid of hydrogen bond donors or acceptors is appropriate for accommodating halogen substituents, as is the case with 11c and 13g. The halogens can be accommodated in the para and/or one, but not both meta positions. Substitutions at both meta positions would not be accommodated, as reflected in the list of potent inhibitors (FIG. 16), since one of them would clash sterically with the side chain of Met65. In contrast with $R_1$, the conformations of the $R_2$ groups of the two inhibitors are drastically different with one exception— the positively charged ring nitrogen of $R_2$ occupies nearly the same location where it forms a salt bridge with the carboxyl group of Glu401 in both structures. Besides this interaction, $R_2$ group of compound 13g makes steric and weak electrostatic interactions with His119, Ser121, Glu401, and the C-terminal carboxyl group (weakly electrostatically interacting with the stem N) on one side and making water-mediated steric interactions with region 26-31 on the other side. In contrast, for the $R_2$ of the compound 11c: while the interactions with one face of this group are made with the same amino acid residues, the other face interacts directly through hydrophobic and steric interactions with the region 26-31, which is in a different conformation. Most prominently, the side chain of Asp26 is flipped to interact with the stem, and Phe24 orthogonally stacks against the double ring. Because the $R_1$ group abuts the hydrophobic wall, whereas $R_2$ group points towards the more extended end of the substrate binding channel, there is more variability in both the identity and the size of $R_2$ substituents, as exhibited in the list of effective $R_2$ groups (FIG. 17).

pool of compounds tested, we found agents that we validated as potent inhibitors of Eis both in the test tube and in the relevant Mtb cultures. Using a ~5-fold larger and more structurally diverse compound library than that used in our initial effort[25] yielded compounds that were 10-fold and more potent than those reported in that previous study. Potencies in mid-nM range appear to be achieved through binding of the compounds via steric complementarity, hydrophobic and hydrogen bonding interactions. While one substituent group ($R_1$) is relatively unchangeable in terms of its size and physico-chemical properties, the other group ($R_2$) can greatly vary. The crystal structures of Eis-inhibitor complexes demonstrate that binding to variable structures is accompanied by conformational plasticity of the aminoglycoside-binding site of Eis, which adapts to different $R_2$ groups, while the protein-$R_1$ interactions are rigid body-like. Binding of the two inhibitors of Eis investigated structurally differs not only in protein conformation, but also in the presence or absence of water-mediated contacts. Interestingly, the exquisite selectivity and potency of Gleevec towards its target Abl kinase have been recently elegantly

TABLE 7

X-ray diffraction data collection and refinement statistics for the EisC204A-CoA-inhibitor 11c and EisC204A-CoA-inhibitor 13g ternary complex structures.

|  | 11c | 13g |
| --- | --- | --- |
| Data collection |  |  |
| Space group | R3$_2$ | R3$_2$ |
| Number of monomers per asymmetric unit | 1 | 1 |
| Unit cell dimensions |  |  |
| a, b, c (Å) | 175.2, 175.2, 122.3 | 175.6, 175.6, 122.2 |
| □, □, □ (°) | 90, 90, 120 | 90, 90, 120 |
| Resolution (Å) | 50.0-2.2 (2.24-2.20)$^a$ | 50.0-2.2 (2.24-2.20)$^a$ |
| I/□ | 21 (2.9) | 24 (4.0) |
| Completeness (%) | 99.9 (100) | 99.8 (99.4) |
| Redundancy | 9.5 (9.4) | 7.3 (7.3) |
| R$_{merge}$ | 0.11 (0.62) | 0.10 (0.56) |
| Number of unique reflections | 34,661 | 34,541 |
| Structure refinement statistics |  |  |
| Resolution (Å) | 40.0-2.2 | 40.0-2.2 |
| R (%) | 19.4 | 20.0 |
| R$_{free}$ (%) | 21.5 | 23.8 |
| Bond length deviation (rmsd) from ideal (Å) | 0.006 | 0.007 |
| Bond angle deviation (rmsd) from ideal (°) | 1.34 | 1.46 |
| Ramachandran plot statistics$^b$ |  |  |
| % of residues in most allowed regions | 94.1 | 93.2 |
| % of residues in additional allowed regions | 5.9 | 6.8 |
| % of residues in generously allowed regions | 0.0 | 0.0 |
| % of residues in disallowed regions | 0.0 (0 residues) | 0.0 (0 residues) |

$^a$Numbers in parentheses indicate the values in the highest-resolution shell.
$^b$Indicates Procheck statistics.[8]

While it has been met with initial skepticism, target-based rational drug design is now gaining momentum and is widely used in industrial and academic drug discovery pipelines, due to advances in HTS technology, robust assay development practices and availability of large and diverse chemical libraries. Prominent examples of successful rational drug design are HIV protease inhibitors ritonavir and the anticancer drug Gleevec. Here, we report the discovery and initial preclinical development of novel first-in-class isothiazole S,S-dioxide heterocyclic inhibitors of a unique acetyl-transferase Eis from Mtb as an agent that overcomes one mechanism of resistance to KAN in Mtb. Among the diverse shown to be a consequence of an induced-fit mechanism, where Abl undergoes unique conformational changes that stabilize Gleevec in the binding site of this kinase and result in a nM affinity.[31] Our Eis inhibitors also appear to be selective in that they do not inhibit other AAC enzymes. This selectivity must be due to the structurally different substrate binding pocket of Eis from that of regiospecific AAC enzymes. Indeed, we demonstrated previously that even though Mtb Eis shares main catalytic residues with Eis homologues from different bacteria and even AAC(2')-Ic, their substrate binding pocket topographies and the surface charges differ dramatically.[12] For example, the C-terminal domain of Eis contributing to the shape of the substrate binding pocket (and containing inhibitor interacting residue Glu401 and the C-terminal carboxyl group) is absent in the single-domain AAC(2')-Ic and other AAC enzymes.[4]

Aminoglycosides are among the antibiotics of last resort for MDR and XDR-TB patients, and resistance to them strongly decreases the chances of a favorable treatment outcome. The strategy of using KAN in combination with an Eis inhibitor is meant not only to overcome KAN resistance due to Eis upregulation, but also to curb emergence of new resistant strains by mutagenesis of the eis promoter, as such mutation would not have survival benefit in the face of combination therapy. This study not only validates AAC's as drug targets, but has set an important precedent for HTS-driven discovery for AACs that cause resistance in clinically useful non-TB pathogens, such as AAC(3) and AAC(6') in *Klebsiella pneumoniae*.[32-34] As with TB, such inhibitory agents could play an important role in both overcoming existing resistance and curbing the acquisition of resistance.

We identified potent inhibitors of Eis enzymatic activity with resulting sensitization of KAN-resistant Mtb cells, in which the resistance to KAN is caused by Eis upregulation. The inhibitors bind in the aminoglycoside binding pocket blocking the access of aminoglycosides to the active site of the enzyme. The inhibitor binding is accompanied by conformational changes of the protein. These compounds have a great potential for further development as KAN adjuvants in Mtb.

Example 5

This example relates to development of inhibitors of Eis. The following compounds were prepared:

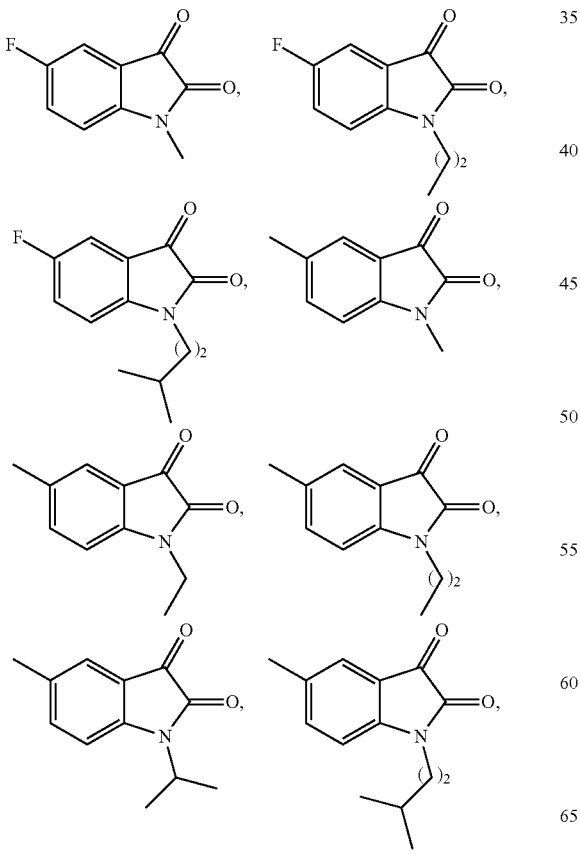

-continued

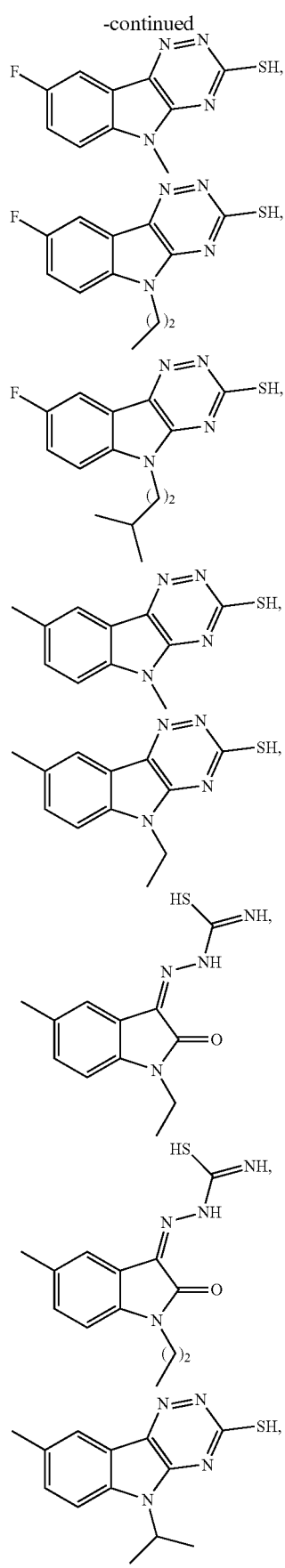

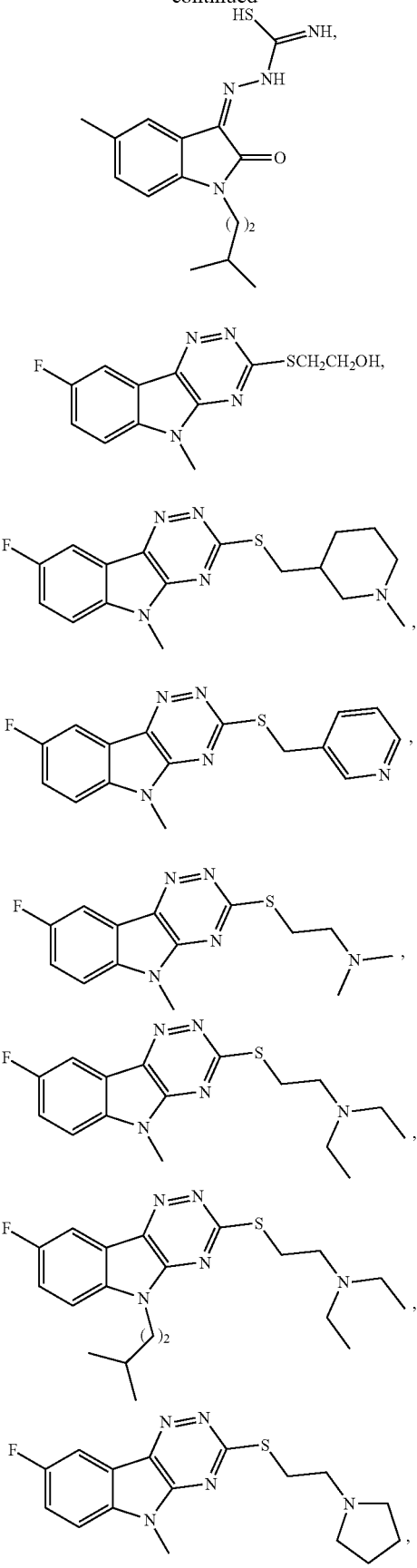
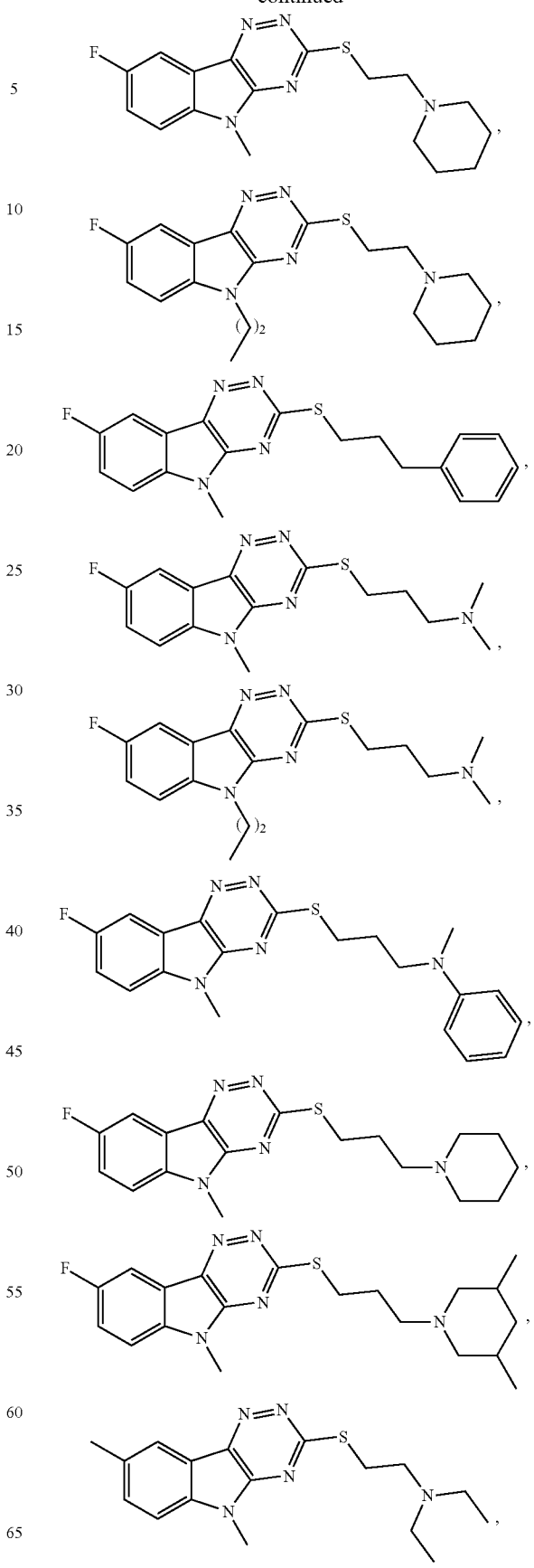

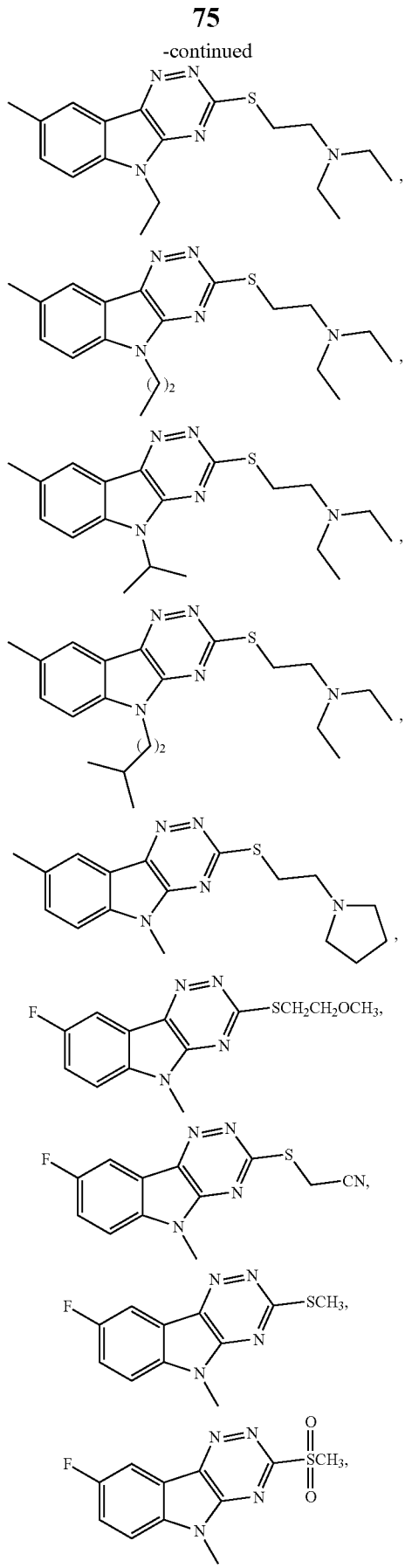

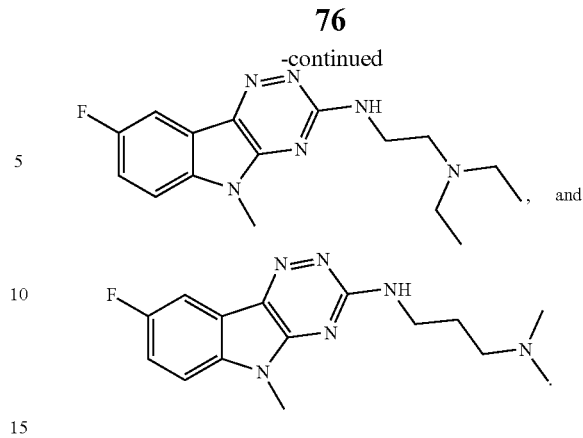

Figure 21:
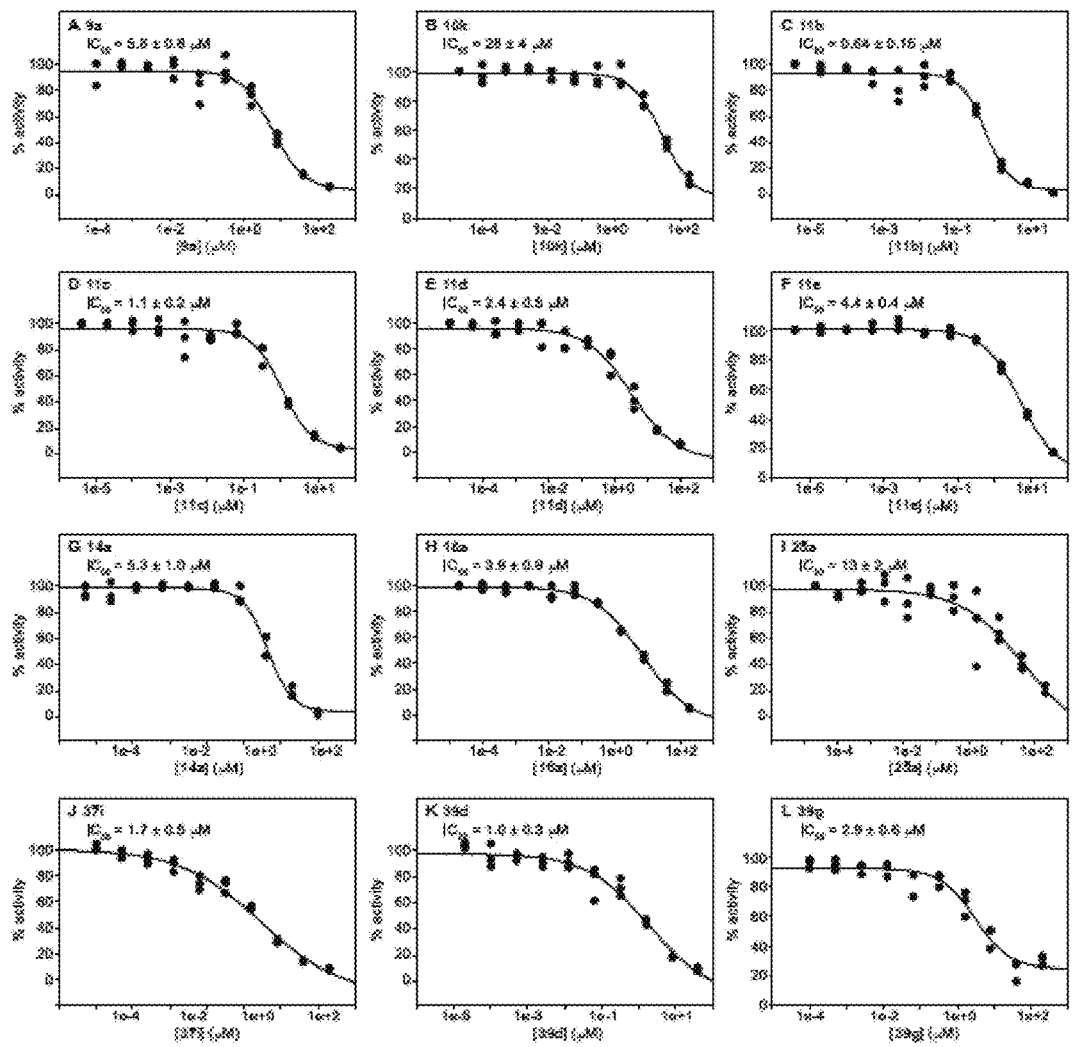
FIG. 21 includes representative $IC_{50}$ curves for exemplary compounds described in Example 5.

Inhibition kinetics. IC50 values were determined on a multimode SpectraMax M5 plate reader using 96-well plates (Thermo Fisher Scientific) by using the UV-Vis assay as above taking measurements every 30 s for 20 min. Compounds were dissolved in Tris (50 mM, pH 8.0 adjusted at rt containing 10% v/v DMSO) (100 1&L) and a 5-fold dilution was performed. To the solution of inhibitors, a mixture (50 1&L) of Eis (1 mM), NEO or KAN (400 1&M), and Tris (50 mM, pH 8.0 adjusted at rt) was added and incubated for 10 min, to allow for competitive binding. Reactions were initiated by addition of a mixture (50 1&L) containing AcCoA (2 mM), DTNB (2 mM), and Tris-HCl (50 mM, pH 8.0 adjusted at rt). Initial rates (first 2-5 min of reaction) were calculated, normalized and zeroed to appropriate controls. All assays were performed at least in triplicate. Data was fit to a Hill-plot fit using KaleidaGraph 4.1 software and $IC_{50}$ values were calculated, and results are set forth in FIG. 21.

Figure 22:
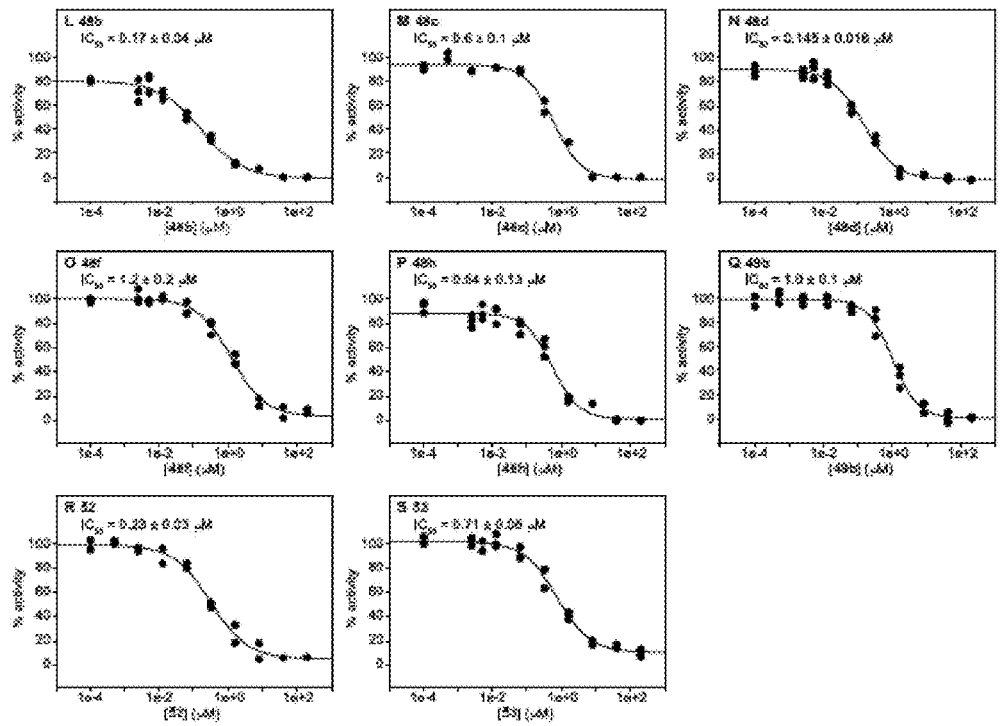
FIG. 22 includes results of a study showing cytotoxicity of KAN against A549, HEK-293, and J774A.1 mammalian cell lines for exemplary compounds described in Example 5.
Figure 22:
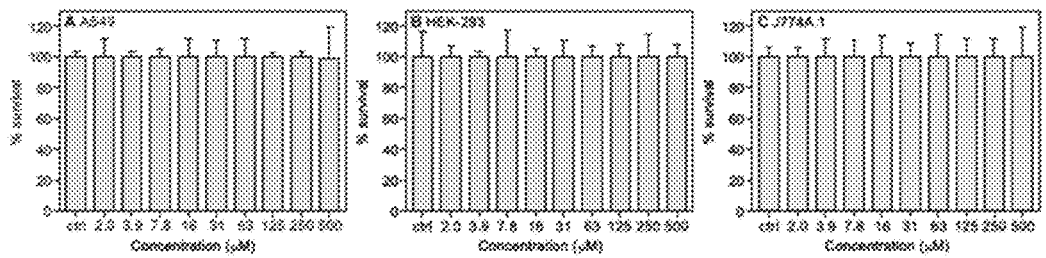

In order to assess the potential cytotoxicity of our inhibitors to mammalian cells, we selected our best Eis inhibitors and tested their cytotoxicity alone or in the presence of KAN against A549, HEK-293, and J774A.1 cells. The percent cell survival was summarized and presented in FIG. 22.

500 $^\alpha$M (FIG. SX), we decided to perform the above toxicity experiments with Eis inhibitors in the presence of 50 $^\alpha$g/mL KAN (equivalent of 86 $^\alpha$(M), which is 10-40× MIC of KAN against Mtb H37Rv in order to better assess the combined toxicity of Eis inhibitors and KAN (FIG. X). Experiments were done in quadruplicate.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

Example 1 References

1. Zaunbrecher, M. A.; Sikes, R. D., Jr.; Metchock, B.; Shinnick, T. M.; Posey, J. E. Overexpression of the chromosomally encoded aminoglycoside acetyltransferase eis confers kanamycin resistance in *Mycobacterium tuberculosis*. Proc. Natl. Acad. Sci., U.S. A. 2009, 106, 20004-20009.
2. Chen, W.; Green, K. D.; Tsodikov, O. V.; Garneau-Tsodikova, S. Aminoglycoside multiacetylating activity of the enhanced intracellular survival protein from *Mycobacterium smegmatis* and its inhibition. Biochemistry 2012, 51, 4959-4967.

3. Houghton, J. L.; Green, K. D.; Pricer, R. E.; Mayhoub, A. S.; Garneau-Tsodikova, S. Unexpected N-acetylation of capreomycin by mycobacterial Eis enzymes. J. Antimicrob. Chemother. 2013, 68, 800-805.
4. Tsodikov, O. V.; Green, K. D.; Garneau-Tsodikova, S. A random sequential mechanism of aminoglycoside acetylation by *Mycobacterium tuberculosis* Eis protein. PloS one 2014, 9, e92370.
5. Chen, W.; Biswas, T.; Porter, V. R.; Tsodikov, O. V.; Garneau-Tsodikova, S. Unusual regioversatility of acetyltransferase Eis, a cause of drug resistance in XDR-TB. Proc. Natl. Acad. Sci., U.S.A. 2011, 108, 9804-9808.
6. Chen, W.; Green, K. D.; Garneau-Tsodikova, S. Cosubstrate tolerance of the aminoglycoside resistance enzyme Eis from *Mycobacterium tuberculosis*. Antimicrob. Agents Chemother. 2012, 56, 5831-5838.
7. Pricer, R. E.; Houghton, J. L.; Green, K. D.; Mayhoub, A. S.; Garneau-Tsodikova, S. Biochemical and structural analysis of aminoglycoside acetyltransferase Eis from *Anabaena variabilis*. Mol. BioSyst. 2012, 8, 3305-3313.
8. Green, K. D.; Pricer, R. E.; Stewart, M. N.; Garneau-Tsodikova, S. Comparative study of Eis-like enzymes from pathogenic and non-pagthogenic bacteria. ACS Infect. Dis. 2015, 1, 272-283.
9. Green, K. D.; Biswas, T.; Chang, C.; Wu, R.; Chen, W.; Janes, B. K.; Chalupska, D.; Gornicki, P.; Hanna, P. C.; Tsodikov, O. V.; Joachimiak, A.; Garneau-Tsodikova, S. Biochemical and structural analysis of an Eis family aminoglycoside acetyltransferase from *Bacillus anthracis*. Biochemistry 2015, 54, 3197-3206.
10. Houghton, J. L.; Biswas, T.; Chen, W.; Tsodikov, O. V.; Garneau-Tsodikova, S. Chemical and structural insights into the regioversatility of the aminoglycoside acetyltransferase Eis. ChemBioChem 2013, 14, 2127-2135.
11. Green, K. D.; Chen, W.; Garneau-Tsodikova, S. Identification and characterization of inhibitors of the aminoglycoside resistance acetyltransferase Eis from *Mycobacterium tuberculosis*. ChemMedChem 2012, 7, 73-77.
12. Green, K. D.; Chen, W.; Houghton, J. L.; Fridman, M.; Garneau-Tsodikova, S. Exploring the substrate promiscuity of drug-modifying enzymes for the chemoenzymatic generation of N-acylated aminoglycosides. ChemBioChem 2010, 11, 119-126.
13. Boehr, D. D.; Daigle, D. M.; Wright, G. D. Domain-domain interactions in the aminoglycoside antibiotic resistance enzyme AAC(6')-APH(2"). Biochemistry 2004, 43, 9846-9855.
14. Willby, M. J.; Green, K. D.; Gajadeera, C. S.; Hou, C.; Tsodikov, O. V.; Posey, J. E.; Garneau-Tsodikova, S. Potent inhibitors of acetyltransferase Eis overcome kanamycin resistance in *Mycobacterium tuberculosis*. ACS Chem. Biol. 2016, 11, 1639-1646.

Example 2 References

1. World Health Organization. Global tuberculosis report 2016. Geneva. Switzerland.
2. Gandhi, N. R.; Nunn, P.; Dheda, K.; Schaaf, H. S.; Zignol, M.; van Soolingen, D.; Jensen, P.; Bayona, J. Multidrug-resistant and extensively drug-resistant tuberculosis: a threat to global control of tuberculosis. Lancet 2010, 375, 1830-1843.
3. Yew, W. W.; Lange, C.; Leung, C. C. Treatment of tuberculosis: update 2010. Eur. Respir. J. 2011, 37, 441-462.
4. Zaunbrecher, M. A.; Sikes, R. D., Jr.; Metchock, B.; Shinnick, T. M.; Posey, J. E. Overexpression of the chromosomally encoded aminoglycoside acetyltransferase eis confers kanamycin resistance in *Mycobacterium tuberculosis*. Proc. Natl. Acad. Sci., U.S.A. 2009, 106, 20004-20009.
5. Campbell, P. J.; Morlock, G. P.; Sikes, R. D.; Dalton, T. L.; Metchock, B.; Starks, A. M.; Hooks, D. P.; Cowan, L. S.; Plikaytis, B. B.; Posey, J. E. Molecular detection of mutations associated with first- and second-line drug resistance compared with conventional drug susceptibility testing of *Mycobacterium tuberculosis*. Antimicrob. Agents Chemother. 2011, 55, 2032-2041.
6. Chen, W.; Biswas, T.; Porter, V. R.; Tsodikov, O. V.; Garneau-Tsodikova, S. Unusual regioversatility of acetyltransferase Eis, a cause of drug resistance in XDR-TB. Proc. Natl. Acad. Sci., U.S.A. 2011, 108, 9804-9808.
7. Tsodikov, O. V.; Green, K. D.; Garneau-Tsodikova, S. A random sequential mechanism of aminoglycoside acetylation by *Mycobacterium tuberculosis* Eis protein. PLoS One 2014, 9, e92370.
8. Green, K. D.; Pricer, R. E.; Stewart, M. N.; Garneau-Tsodikova, S. Comparative study of Eis-like enzymes from pathogenic and non-pathogenic bacteria. ACS Infect. Dis. 2015, 1, 272-283.
9. Chen, W.; Green, K. D.; Tsodikov, O. V.; Garneau-Tsodikova, S. Aminoglycoside multiacetylating activity of the enhanced intracellular survival protein from *Mycobacterium smegmatis* and its inhibition. Biochemistry 2012, 51, 4959-4967.
10. Green, K. D.; Biswas, T.; Chang, C.; Wu, R.; Chen, W.; Janes, B. K.; Chalupska, D.; Gornicki, P.; Hanna, P. C.; Tsodikov, O. V.; Joachimiak, A.; Garneau-Tsodikova, S. Biochemical and structural analysis of an Eis family aminoglycoside acetyltransferase from *Bacillus anthracis*. Biochemistry 2015, 54, 3197-3206.
11. Pricer, R. E.; Houghton, J. L.; Green, K. D.; Mayhoub, A. S.; Garneau-Tsodikova, S. Biochemical and structural analysis of aminoglycoside acetyltransferase Eis from *Anabaena variabilis*. Mol. BioSyst. 2012, 8, 3305-3313.
12. Houghton, J. L.; Green, K. D.; Pricer, R. E.; Mayhoub, A. S.; Garneau-Tsodikova, S. Unexpected N-acetylation of capreomycin by mycobacterial Eis enzymes. J. Antimicrob. Chemother. 2013, 68, 800-805.
13. Kim, K. H.; An, D. R.; Song, J.; Yoon, J. Y.; Kim, H. S.; Yoon, H. J.; Im, H. N.; Kim, J.; Kim, D. J.; Lee, S. J.; Kim, K. H.; Lee, H. M.; Kim, H. J.; Jo, E. K.; Lee, J. Y.; Suh, S. W. *Mycobacterium tuberculosis* Eis protein initiates suppression of host immune responses by acetylation of DUSP16/MKP-7. Proc. Natl. Acad. Sci., U.S.A. 2012, 109, 7729-7734.
14. Li, Y.; Green, K. D.; Johnson, B. R.; Garneau-Tsodikova, S. Inhibition of aminoglycoside acetyltransferase resistance enzymes by metal salts. Antimicrob. Agents Chemother. 2015, 59, 4148-4156.
15. Willby, M. J.; Green, K. D.; Gajadeera, C. S.; Hou, C.; Tsodikov, O. V.; Posey, J. E.; Garneau-Tsodikova, S. Potent inhibitors of acetyltransferase Eis overcome kanamycin resistance in *Mycobacterium tuberculosis*. ACS Chem. Biol. 2016, 11, 1639-1646.
16. Garzan, A.; Willby, M. J.; Green, K. D.; Gajadeera, C. S.; Hou, C.; Tsodikov, O. V.; Posey, J. E.; Garneau-Tsodikova, S. Sulfonamide-based inhibitors of aminoglycoside acetyltransferase Eis abolish resistance to kanamycin in *Mycobacterium tuberculosis*. J. Med. Chem. 2016, 59, 10619-10628.
17. Garzan, A.; Willby, M. J.; Green, K. D.; Tsodikov, O. V.; Posey, J. E.; Garneau-Tsodikova, S. Discovery and optimization of two Eis inhibitor families as kanamycin 18. Green, K. D.; Chen, W.; Garneau-Tsodikova, S. Identification and characterization of inhibitors of the aminoglycoside resistance acetyltransferase Eis from *Mycobacterium tuberculosis*. ChemMedChem 2012, 7, 73-77.
19. Kawashita, Y.; Hayashi, M. Synthesis of heteroaromatic compounds by oxidative aromatization using an activated carbon/molecular oxygen system. Molecules 2009, 14, 3073-3093.
20. Houghton, J. L.; Biswas, T.; Chen, W.; Tsodikov, O. V.; Garneau-Tsodikova, S. Chemical and structural insights into the regioversatility of the aminoglycoside acetyltransferase Eis. ChemBioChem 2013, 14, 2127-2135.
21. Quave, C. L.; Estevez-Carmona, M.; Compadre, C. M.; Hobby, G.; Hendrickson, H.; Beenken, K. E.; Smeltzer, M. S. Ellagic acid derivatives from *Rubus ulmifolius* inhibit *Staphylococcus aureus* biofilm formation and improve response to antibiotics. PLoS One 2012, 7, e28737.
22. Hall, B. S.; Bot, C.; Wilkinson, S. R. Nifurtimox activation by trypanosomal type I nitroreductases generates cytotoxic nitrile metabolites. J. Biol. Chem. 2011, 286, 13088-13095.
23. Xu, W.; Zhu, X.; Tan, T.; Li, W.; Shan, A. Design of embedded-hybrid antimicrobial peptides with enhanced cell selectivity and anti-biofilm activity. PLoS One 2014, 9, e98935.
24. Shrestha, S. K.; Fosso, M. Y.; Green, K. D.; Garneau-Tsodikova, S. Amphiphilic tobramycin analogues as antibacterial and antifungal agents. Antimicrob. Agents Chemother. 2015, 59, 4861-4869.
25. Fosso, M. Y.; Shrestha, S. K.; Green, K. D.; Garneau-Tsodikova, S. Synthesis and bioactivities of kanamycin B-derived cationic amphiphiles. J. Med. Chem. 2015, 58, 9124-9132.

Example 3 References

1. World Health Organization. *Global Tuberculosis Report 2014*. Geneva. 2014.
2. Zaunbrecher, M. A.; Sikes, R. D., Jr.; Metchock, B.; Shinnick, T. M.; Posey, J. E. Overexpression of the chromosomally encoded aminoglycoside acetyltransferase eis confers kanamycin resistance in *Mycobacterium tuberculosis*. Proc. Natl. Acad. Sci. U.S.A. 2009, 106, 20004-20009.
3. Campbell, P. J.; Morlock, G. P.; Sikes, R. D.; Dalton, T. L.; Metchock, B.; Starks, A. M.; Hooks, D. P.; Cowan, L. S.; Plikaytis, B. B.; Posey, J. E. Molecular detection of mutations associated with first- and second-line drug resistance compared with conventional drug susceptibility testing of *Mycobacterium tuberculosis*. Antimicrob. Agents Chemother. 2011, 55, 2032-2041.
4. Jnawali, H. N.; Yoo, H.; Ryoo, S.; Lee, K. J.; Kim, B. J.; Koh, W. J.; Kim, C. K.; Kim, H. J.; Park, Y. K. Molecular genetics of *Mycobacterium tuberculosis* resistant to aminoglycosides and cyclic peptide capreomycin antibiotics in Korea. World J. Microbiol. Biotechnol. 2013, 29, 975-982.
5. Chen, W.; Biswas, T.; Porter, V. R.; Tsodikov, O. V.; Garneau-Tsodikova, S. Unusual regioversatility of acetyltransferase Eis, a cause of drug resistance in XDR-TB. Proc. Natl. Acad. Sci. U.S.A. 2011, 108, 9804-9808.
6. Tsodikov, O. V.; Green, K. D.; Garneau-Tsodikova, S. A random sequential mechanism of aminoglycoside acetylation by *Mycobacterium tuberculosis* Eis protein. PLoS One 2014, 9, e92370.
7. Houghton, J. L.; Biswas, T.; Chen, W.; Tsodikov, O. V.; Garneau-Tsodikova, S. Chemical and structural insights into the regioversatility of the aminoglycoside acetyltransferase Eis. ChemBioChem 2013, 14, 2127-2135.
8. Chen, W.; Green, K. D.; Tsodikov, O. V.; Garneau-Tsodikova, S. Aminoglycoside multiacetylating activity of the enhanced intracellular survival protein from *Mycobacterium smegmatis* and its inhibition. Biochemistry 2012, 51, 4959-4967.
9. Green, K. D.; Pricer, R. E.; Stewart, M. N.; Garneau-Tsodikova, S. Comparative study of Eis-like enzymes from pathogenic and non-pagthogenic bacteria. ACS Infect. Dis. 2015, 1, 272-283.
10. Pricer, R. E.; Houghton, J. L.; Green, K. D.; Mayhoub, A. S.; Garneau-Tsodikova, S. Biochemical and structural analysis of aminoglycoside acetyltransferase Eis from *Anabaena variabilis*. Mol. BioSyst. 2012, 8, 3305-3313.
11. Green, K. D.; Biswas, T.; Chang, C.; Wu, R.; Chen, W.; Janes, B. K.; Chalupska, D.; Gornicki, P.; Hanna, P. C.; Tsodikov, O. V.; Joachimiak, A.; Garneau-Tsodikova, S. Biochemical and structural analysis of an Eis family aminoglycoside acetyltransferase from *Bacillus anthracis*. Biochemistry 2015, 54, 3197-3206.
12. Green, K. D.; Chen, W.; Garneau-Tsodikova, S. Identification and characterization of inhibitors of the aminoglycoside resistance acetyltransferase Eis from *Mycobacterium tuberculosis*. ChemMedChem 2012, 7, 73-77.
13. Chen, W.; Green, K. D.; Garneau-Tsodikova, S. Cosubstrate tolerance of the aminoglycoside resistance enzyme Eis from *Mycobacterium tuberculosis*. Antimicrob. Agents Chemother. 2012, 56, 5831-5838.
14. Houghton, J. L.; Green, K. D.; Pricer, R. E.; Mayhoub, A. S.; Garneau-Tsodikova, S. Unexpected N-acetylation of capreomycin by mycobacterial Eis enzymes. J. Antimicrob. Chemother. 2013, 68, 800-805.
15. Yoon, H. J.; Kim, K. H.; Yang, J. K.; Suh, S. W.; Kim, H.; Jang, S. A docking study of enhanced intracellular survival protein from *Mycobacterium tuberculosis* with human DUSP16/MKP-7. J. Synchrotron Radiat. 2013, 20, 929-932.
16. Hugonnet, J. E.; Tremblay, L. W.; Boshoff, H. I.; Barry, C. E., 3rd; Blanchard, J. S. Meropenem-clavulanate is effective against extensively drug-resistant *Mycobacterium tuberculosis*. Science 2009, 323, 1215-1218.
17. Willby, M. J.; Green, K. D.; Gajadeera, C. S.; Hou, C.; Tsodikov, O. V.; Posey, J. E.; Garneau-Tsodikova, S. Potent inhibitors of acetyltransferase Eis overcome kanamycin resistance in *Mycobacterium tuberculosis*. ACS Chem. Biol. 2016, 11, 1639-1646.
18. Garzan, A.; Willby, M. J.; Green, K. D.; Tsodikov, O. V.; Posey, J. E.; Garneau-Tsodikova, S. Discovery and optimization of two Eis inhibitor families as kanamycin adjuvants against drug-resistant *M. tuberculosis*. ACS Med. Chem. Lett. 2016, DOI: 10.1021/acsmedchemlett.6b00261.
19. Ainsa, J. A.; Perez, E.; Pelicic, V.; Berthet, F. X.; Gicquel, B.; Martin, C. Aminoglycoside 2'-N-acetyltransferase genes are universally present in mycobacteria: characterization of the aac(2')-Ic gene from *Mycobacterium tuberculosis* and the aac(2')-Id gene from *Mycobacterium smegmatis*. Mol. Microbiol. 1997, 24, 431-441.
20. Vetting, M. W.; Hegde, S. S.; Javid-Majd, F.; Blanchard, J. S.; Roderick, S. L. Aminoglycoside 2'-N-acetyltransferase from *Mycobacterium tuberculosis* in complex with coenzyme A and aminoglycoside substrates. *Nat. Struct. Biol.* 2002, 9, 653-658.
21. Green, K. D.; Chen, W.; Houghton, J. L.; Fridman, M.; Garneau-Tsodikova, S. Exploring the substrate promiscuity of drug-modifying enzymes for the chemoenzymatic generation of N-acylated aminoglycosides. *ChemBioChem* 2010, 11, 119-126.
22. Magalhaes, M. L.; Blanchard, J. S. The kinetic mechanism of AAC3-IV aminoglycoside acetyltransferase from *Escherichia coli*. *Biochemistry* 2005, 44, 16275-16283.
23. Boehr, D. D.; Daigle, D. M.; Wright, G. D. Domain-domain interactions in the aminoglycoside antibiotic resistance enzyme AAC(6')-APH(2"). *Biochemistry* 2004, 43, 9846-9855.
24. Caldwell, S. J.; Berghuis, A. M. Small-angle X-ray scattering analysis of the bifunctional antibiotic resistance enzyme aminoglycoside (6') acetyltransferase-Ie/aminoglycoside (2") phosphotransferase-Ia reveals a rigid solution structure. *Antimicrob. Agents Chemother.* 2012, 56, 1899-1906.
25. Obamefi, C.; Akinpelu, D. Synthesis and antimicrobial activity of some 2(1H)-quinoxaline-6-sulfonyl derivatives. *Phosphorus, Sulfur Silicon Relat. Elem.* 2005, 180, 1795-1807.
26. Otwinowski, Z.; Minor, W. Processing of X-ray diffraction data collected in oscillation mode. *Methods Enzymol.* 1997, 276, 307-326.
27. Murshudov, G. N.; Vagin, A. A.; Dodson, E. J. Refinement of macromolecular structures by the maximum-likelihood method. *Acta Crystallogr. D* 1997, 53, 240-55.
28. Emsley, P.; Cowtan, K. Coot: model-building tools for molecular graphics. *Acta Crystallogr. D* 2004, 60, 2126-32.
29. Laskowski, R. A.; Macarthur, M. W.; Moss, D. S.; Thornton, J. M. Procheck—a program to check the stereochemical quality of protein structures. *J. Appl. Cryst.* 1993, 26, 283-291.

Example 4 References (1) World Health Organization (2014) Global tuberculosis report 2014. ISBM 978 992 974 156580 156589.
(2) Green, K. D.; Garneau-Tsodikova, S. Front. Microbiol. 2013, 4, 208.
(3) Campbell, P. J.; Morlock, G. P.; Sikes, R. D.; Dalton, T. L.; Metchock, B.; Starks, A. M.; Hooks, D. P.; Cowan, L. S.; Plikaytis, B. B.; Posey, J. E. Molecular detection of mutations associated with first- and second-line drug resistance compared with conventional drug susceptibility testing of *Mycobacterium tuberculosis*. Antimicrob. Agents Chemother. 2011, 55, 2032-2041.
(4) Chen, W.; Biswas, T.; Porter, V. R.; Tsodikov, O. V.; Garneau-Tsodikova, S. Unusual regioversatility of acetyltransferase Eis, a cause of drug resistance in XDR-TB. Proc. Acad. Natl. Sci., U.S.A. 2011, 108, 9804-9808.
(5) Chen, W.; Green, K. D.; Tsodikov, O. V.; Garneau-Tsodikova, S. Aminoglycoside multiacetylating activity of the enhanced in-tracellular survival protein from *Mycobacterium smegmatis* and its inhibition. Biochemistry 2012, 51, 4959-4967.
(6) Chen, W.; Green, K. D.; Garneau-Tsodikova, S. Cosubstrate tolerance of the aminoglycoside resistance enzyme Eis from *Mycobacterium tuberculosis*. Antimicrob. Agents Chemother. 2012, 56, 5831-5838.
(7) Houghton, J. L.; Green, K. D.; Pricer, R. E.; Mayhoub, A. S.; Garneau-Tsodikova, S. Unexpected N-acetylation of capreo-mycin by mycobacterial Eis enzymes. J. Antimicrob. Chemother. 2013, 68, 800-805.
(8) Jennings, B. C.; Labby, K. J.; Green, K. D.; Garneau-Tsodikova, S. Redesign of substrate specificity and identification of the aminoglycoside binding residues of Eis from *Mycobacterium tuberculosis*. Biochemistry 2013, 52, 5125-5132.
(9) Tsodikov, O. V.; Green, K. D.; Garneau-Tsodikova, S. A random sequential mechanism of aminoglycoside acetylation by *Mycobacterium tuberculosis* Eis protein. PloS one 2014, 9, e92370.
(10) Houghton, J. L.; Biswas, T.; Chen, W.; Tsodikov, O. V.; Garneau-Tsodikova, S. Chemical and structural insights into the regioversatility of the aminoglycoside acetyltransferase Eis. ChemBioChem 2013, 14, 2127-2135.
(11) Pricer, R. E.; Houghton, J. L.; Green, K. D.; Mayhoub, A. S.; Garneau-Tsodikova, S. Biochemical and structural analysis of aminoglycoside acetyltransferase Eis from *Anabaena variabilis*. Mol. BioSyst. 2012, 8, 3305-3313.
(12) Green, K. D.; Biswas, T.; Chang, C.; Wu, R.; Chen, W.; Janes, B. K.; Chalupska, D.; Gornicki, P.; Hanna, P. C.; Tsodikov, O. V.; Joachimiak, A.; Garneau-Tsodikova, S. Biochemical and structural analysis of an Eis family aminoglycoside acetyltransferase from *Bacillus anthracis*. Biochemistry 2015, 54, 3197-3206.
(13) Green, K. D.; Pricer, R. E.; Stewart, M. N.; Garneau-Tsodikova, S. Comparative study of Eis-like enzymes from pathogenic and non-pathogenic bacteria. ACS Infect. Dis. 2015, 1, 272-283.
(14) Hugonnet, J. E.; Tremblay, L. W.; Boshoff, H. I.; Barry, C. E., 3rd; Blanchard, J. S. Meropenem-clavulanate is effective against extensively drug-resistant *Mycobacterium tuberculosis*. Science 2009, 323, 1215-1218.
(15) Zhang, J.; Sun, Y.; Wang, Y.; Lu, M.; He, J.; Liu, J.; Chen, Q.; Zhang, X.; Zhou, F.; Wang, G.; Sun, X. Non-antibiotic agent ginsenoside 20(S)-Rh2 enhanced the antibacterial effects of ciprofloxacin in vitro and in vivo as a potential NorA inhibitor. Eur. J. Pharmacol. 2014, 740, 277-284.
(16) Shlaes, D. M. New beta-lactam-beta-lactamase inhibitor combi-nations in clinical development. Ann. New York Acad. Sci. 2013, 1277, 105-114.
(17) Zhanel, G. G.; Lawson, C. D.; Adam, H.; Schweizer, F.; Zelenitsky, S.; Lagace-Wiens, P. R.; Denisuik, A.; Rubinstein, E.; Gin, A. S.; Hoban, D. J.; Lynch, J. P., 3rd; Karlowsky, J. A. Ceftazidime-avibactam: a novel cephalosporin/beta-lactamase inhibitor combination. Drugs 2013, 73, 159-177.
(18) Sader, H. S.; Castanheira, M.; Flamm, R. K.; Farrell, D. J.; Jones, R. N. Antimicrobial activity of ceftazidime-avibactam against Gram-negative organisms collected from U.S. medical centers in 2012. Antimicrob. Agents Chemother. 2014, 58, 1684-1692.
(19) Gao, F.; Yan, X.; Auclair, K. Synthesis of a phosphonate-linked aminoglycoside-coenzyme a bisubstrate and use in mechanistic studies of an enzyme involved in aminoglycoside resistance. Chemistry 2009, 15, 2064-2070.
(20) Gao, F.; Yan, X.; Baettig, O. M.; Berghuis, A. M.; Auclair, K. Regio- and chemoselective 6'-N-derivatization of aminoglyco-sides: bisubstrate inhibitors as probes to study aminoglycoside 6'-N-acetyltransferases. Angew. Chem. 2005, 44, 6859-6862.
(21) Gao, F.; Yan, X.; Shakya, T.; Baettig, O. M.; Ait-Mohand-Brunet, S.; Berghuis, A. M.; Wright, G. D.; Auclair, K. Synthe-sis and structure-activity relationships of truncated bisubstrate inhibitors of aminoglycoside 6'-N-acetyltransferases. J. Med. Chem. 2006, 49, 5273-5281.
(22) Gao, F.; Yan, X.; Zahr, O.; Larsen, A.; Vong, K.; Auclair, K. Synthesis and use of sulfonamide-, sulfoxide-, or sulfone-containing aminoglycoside-CoA bisubstrates as mechanistic probes for aminoglycoside N-6'-acetyltransferase. Bioorg. Med. Chem. Lett. 2008, 18, 5518-5522.
(23) Boehr, D. D.; Draker, K. A.; Koteva, K.; Bains, M.; Hancock, R. E.; Wright, G. D. Broad-spectrum peptide inhibitors of aminoglycoside antibiotic resistance enzymes. Chem. Biol. 2003, 10, 189-196.
(24) Suga, T.; Ishii, T.; Iwatsuki, M.; Yamamoto, T.; Nonaka, K.; Masuma, R.; Matsui, H.; Hanaki, H.; Omura, S.; Shiomi, K. Aranorosin circumvents arbekacin-resistance in MRSA by inhibiting the bifunctional enzyme AAC(6')/APH(2"). J. Antibiot. 2012, 65, 527-529.
(25) Green, K. D.; Chen, W.; Garneau-Tsodikova, S. Identification and characterization of inhibitors of the aminoglycoside resistance acetyltransferase Eis from *Mycobacterium tuberculosis*. ChemMedChem 2012, 7, 73-77.
(26) Boehr, D. D.; Daigle, D. M.; Wright, G. D. Domain-domain interactions in the aminoglycoside antibiotic resistance enzyme AAC(6')-APH(2"). Biochemistry 2004, 43, 9846-9855.
(27) Caldwell, S. J.; Berghuis, A. M. Small-angle X-ray scattering analysis of the bifunctional antibiotic resistance enzyme aminoglycoside (6') acetyltransferase-ie/aminoglycoside (2") phosphotransferase-ia reveals a rigid solution structure. Antimicrob. Agents Chemother. 2012, 56, 1899-1906.
(28) Magalhaes, M. L.; Blanchard, J. S. The kinetic mechanism of AAC3-IV aminoglycoside acetyltransferase from *Escherichia coli*. Biochemistry 2005, 44, 16275-16283.
(29) Ainsa, J. A.; Perez, E.; Pelicic, V.; Berthet, F. X.; Gicquel, B.; Martin, C. Aminoglycoside 2'-N-acetyltransferase genes are universally present in mycobacteria: characterization of the aac(2')-Ic gene from *Mycobacterium tuberculosis* and the aac(2')-Id gene from *Mycobacterium smegmatis*. Mol. Microbiol. 1997, 24, 431-441.
(30) Vetting, M. W.; Hegde, S. S.; Javid-Majd, F.; Blanchard, J. S.; Roderick, S. L. Aminoglycoside 2'-N-acetyltransferase from *Mycobacterium tuberculosis* in complex with coenzyme A and aminoglycoside substrates. Nat. Struct. Biol. 2002, 9, 653-658.
(31) Agafonov, R. V.; Wilson, C.; Otten, R.; Buosi, V.; Kern, D. Energetic dissection of Gleevec's selectivity toward human tyrosine kinases. Nat. Struct. Mol. Biol. 2014, 21, 848-853.
(32) Mainardi, J. L.; Zhou, X. Y.; Goldstein, F.; Mohler, J.; Farinotti, R.; Gutmann, L.; Carbon, C. Activity of isepamicin and selection of permeability mutants to beta-lactams during aminoglycoside therapy of experimental endocarditis due to *Klebsiella pneumoniae*-Cf104 producing an aminoglycoside acetyltransferase 6' modifying enzyme and a Tem-3 beta-lactamase. J. Infect. Dis. 1994, 169, 1318-1324.
(33) Stoesser, N.; Batty, E. M.; Eyre, D. W.; Morgan, M.; Wyllie, D. H.; Elias, C. D.; Johnson, J. R.; Walker, A. S.; Peto, T. E. A.; Crook, D. W. Predicting antimicrobial susceptibilities for *Escherichia coli* and *Klebsiella pneumoniae* isolates using whole genomic sequence data. J. Antimicrob. Chemother. 2013, 68, 2234-2244.
(34) Filippa, N.; Carricajo, A.; Grattard, F.; Fascia, P.; El Sayed, F.; Defilippis, J. P.; Berthelot, P.; Aubert, G. Outbreak of multi-drug-resistant *Klebsiella pneumoniae* carrying qnrB1 and bla(CTX-M15) in a French intensive care unit. Ann. Intensive Care 2013, 3, 18.
(35) Green, K. D.; Chen, W.; Houghton, J. L.; Fridman, M.; Garneau-Tsodikova, S. Exploring the substrate promiscuity of drug-modifying enzymes for the chemoenzymatic generation of N-acylated aminoglycosides. ChemBioChem 2010, 11, 119-126.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound selected from the group consisting of:

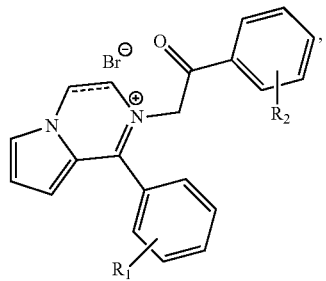

wherein $R_1$ is selected from the group consisting of H, p-F, m,p-di-F; and $R_2$ is selected from the group consisting of H, o-F, m-F, m-Cl, m-Br, m-OH, m-OMe, p-F, p-Cl, p-Br, and p-Me.

2. A pharmaceutical composition comprising the compound of claim 1, and a suitable pharmaceutical carrier.

3. A method of treating aminoglycoside-resistant *Mycobacterium tuberculosis* (Mtb), comprising administering an effective amount of the compound of claim 1.

4. The method of claim 3, and further comprising administering an aminoglycoside.

5. The method of claim 4, wherein the aminoglycoside is kanamycin (KAN).

6. The method of claim 4, wherein the aminoglycoside is administered to a subject in need of treatment for aminoglycoside-resistant Mtb.

7. A composition comprising the compound of claim 1 and an aminoglycoside.

8. The composition of claim 7, wherein the aminoglycoside is kanamycin (KAN).

\* \* \* \* \*